US008178522B2

(12) United States Patent
Jakob-Roetne et al.

(10) Patent No.: US 8,178,522 B2
(45) Date of Patent: May 15, 2012

(54) THIAZOLES

(75) Inventors: Roland Jakob-Roetne, Inzlingen (DE);
Matthew C. Lucas, Verona, NJ (US);
Andrew Thomas, Binningen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 107 days.

(21) Appl. No.: 12/768,779

(22) Filed: Apr. 28, 2010

(65) Prior Publication Data

US 2010/0286116 A1  Nov. 11, 2010

(30) Foreign Application Priority Data

May 5, 2009  (EP) .................................... 09159411

(51) Int. Cl.
*A61K 31/397* (2006.01)
*A61K 31/427* (2006.01)
*A61K 31/4439* (2006.01)
*A61K 31/541* (2006.01)
*A61K 31/5377* (2006.01)
*C07D 417/06* (2006.01)
*C07D 417/14* (2006.01)

(52) U.S. Cl. ............. 514/210.18; 514/227.8; 514/236.8; 514/342; 514/365; 544/58.4; 544/133; 546/269.7; 548/200

(58) Field of Classification Search .......................... None
See application file for complete search history.

(56) References Cited

U.S. PATENT DOCUMENTS

| 4,639,266 | A | 1/1987 | Heubach et al. |
| 2003/0055085 | A1 | 3/2003 | Wagener et al. |
| 2004/0006226 | A1 | 1/2004 | Ladduwahetty et al. |
| 2009/0143371 | A1 | 6/2009 | Buettelmann et al. |
| 2009/0143385 | A1 | 6/2009 | Buettelmann et al. |
| 2009/0143407 | A1 | 6/2009 | Buettelmann et al. |

FOREIGN PATENT DOCUMENTS

| DE | 3525205 | 3/1986 |
| EP | 1894924 | 3/2008 |
| GB | 2336589 | 10/1999 |
| JP | 2007230909 | 9/2007 |
| WO | 0129015 | 4/2001 |
| WO | 0134603 | 5/2001 |
| WO | 0250062 | 6/2002 |
| WO | 02081474 | 10/2002 |
| WO | 03004027 | 1/2003 |
| WO | 03015771 | 2/2003 |
| WO | 03044017 | 5/2003 |
| WO | 2004048349 | 6/2004 |
| WO | 2005014553 | 2/2005 |
| WO | 2005118568 | 12/2005 |
| WO | 2005123672 | 12/2005 |
| WO | 2006037480 | 4/2006 |
| WO | 2006044617 | 4/2006 |
| WO | 2006069155 | 6/2006 |
| WO | 2007009275 | 1/2007 |
| WO | 2007039389 | 4/2007 |
| WO | 2007052843 | 5/2007 |
| WO | 2007076260 | 7/2007 |
| WO | 2007092751 | 8/2007 |
| WO | 2007/137954 | 12/2007 |
| WO | 2008025539 | 3/2008 |
| WO | 2008025540 | 3/2008 |

OTHER PUBLICATIONS

McNamara et al., Psychobiology (1993), vol. 21, pp. 101-108.
Goodman et al., Tetrahedron (1999) vol. 55 pp. 15067-15070.
Abstract corresponding to JP 2007/230909.
Roy et al., Synthesis, 2003 pp. 1347-1356.
White, et al., Journal of Organic Chemistry (1981), vol. 46(11) pp. 2273-2280.
Shi Shun et al., J. Org. Chem. vol. 68 (2003) pp. 6810-6813.
Lam et al., Bioorganic & Medicinal Chemistry Letters (2003) vol. 13(10) pp. 1795-1799.
Wang et al., Journal of Fluorine Chemistry, vol. 111(2) pp. 241-246 (2001).
Hamper et al., J. Agric. Food Chem. (1995), vol. 43, pp. 219-228.
Kumar, et al., Tetrahedron Letters, vol. 47, (2006), p. 1457-1460.
Burke, et al., Journal of Natural Products, 1986, vol. 49, pp. 522-523.
Hormi, Organic Syntheses, vol. 8, p. 247 (1993) & vol. 66, (1988), p. 173.
Andosova et al., Pharmaceutical Chemistry Journal (English Translation), vol. 12, No. 8, 1978, pp. 1019-1022.
Doyle, et al., Journal of the Chem. Society, 1963, pp. 5838-5845.
Anderson, et al., Journal of Organic Chem. vol. 51(6), 1986, pp. 945-947.
Bourbeau et al., Organic Letters, vol. 8(17), 2006, pp. 3679-3680.
Waldo et al., Org. Lett. vol. (7) pp. 5203-5205 (2005).
Seydel et al., J. Med. Chem. vol. (19) pp. 483-492 (1976).
Kirk, K. L., J. Org. Chem. vol. (43) pp. 4381-4383 (1978).
Ley et al., Angew Chem, 2003 vol. 115 p. 5558-5606.
Hüttel et al., Liebigs, Ann. Chem. vol. 593, pp. 200-207 (1955) (English translation).
Austin et al., J. Org. Chem. vol. 46, pp. 2280-2286 (1981).
Schlosser et al., Eur. J. Org. Chem. vol. (24), p. 4181-4184 (2002).
Félix et al., J. Org. Chem. 1995, vol. 60 p. 3907-3909.
Otani et al., Neuroscience Letters, 2005, vol. 381 pp. 108-113.
Papadimitriou et al., Neuropsychobiology, 2001, vol. 43(3) pp. 141-144.

(Continued)

*Primary Examiner* — Kamal Saeed
(74) *Attorney, Agent, or Firm* — George Johnston; Patricia S. Rocha-Tramaloni; Kimberly J. Prior

(57) ABSTRACT

The present invention is concerned with isoxazole-thiazole derivatives of formula I, having affinity and selectivity for GABA A α5 receptor, their manufacture, pharmaceutical compositions containing them and their use as therapeutically active substances. The active compounds of the present invention are useful as cognitive enhancer or for the therapeutic and/or prophylactic treatment of cognitive disorders like Alzheimer's disease.

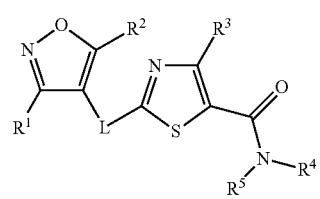

33 Claims, No Drawings

OTHER PUBLICATIONS

McCauley et al., American J. Med. Genetics, 2004, 131B, pp. 51-59.
DeLong et al., Autism, 2007, vol. 11(2) pp. 135-147.
Solis Anez et al., Investigacion Clinica, 2007 vol. 28, pp. 529-541.
Fernandez et al., Nature, Neuroscience, 2007, vol. 10 pp. 411-413.
Rueda et al., Neuroscience Letters, 2008, vol. 433 pp. 22-27.
Cui et al., Cell. 2008, vol. 135, pp. 549-560.
Deshayes et al., Synthesis, 1984, pp. 868-870.
International Search Report by EPO for case 25117, International Appl. PCT/EP2010/055693, mailed Jul. 28, 2010.

THIAZOLES

PRIORITY TO RELATED APPLICATION(S)

This application claims the benefit of European Patent Application No. 09159411.9, filed May 5, 2009, which is hereby incorporated by reference in its entirety.

FIELD OF THE INVENTION

The present invention provides isoxazole-thiazoles having affinity and selectivity for GABA A α5 receptors, their manufacture, pharmaceutical compositions containing them and their use as therapeutically active substances.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of α, β and γ subunits. Presently a total number of 21 subunits of the GABA A receptor have been cloned and sequenced. Three types of subunits (α, β and γ) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the α and γ subunits. Among the recombinant GABA A receptors, α1β2γ2 mimics many effects of the classical type-I BzR subtypes, whereas α2β2γ2, α3β2γ2 and α5β2γ2 ion channels are termed type-II BzR.

It has been shown by McNamara and Skelton in Psychobiology, 1993, 21:101-108 that the benzodiazepine receptor inverse agonist β-CCM enhance spatial learning in the Morris watermaze. However, β-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A α5 receptor partial or full inverse agonist which is relatively free of activity at GABA A α1 and/or α2 and/or α3 receptor can be used to provide a therapeutically active substance which is useful for enhancing cognition with reduced or without proconvulsant activity. It is also possible to use GABA A α5 inverse agonists which are not free of activity at GABA A α1 and/or α2 and/or α3 receptor but which are functionally selective for α5 containing subunits. However, inverse agonists which are selective for GABA A α5 subunits and are relatively free of activity at GABA A α1, α2 and α3 receptor are preferred.

Literature has been published to establish the link between GABA A α5 subunits and the therapeutic and/or prophylactic treatment of various diseases and disorders of the Central Nervous System, like Neuroscience Letts., 2005, 381, 108-13, Neuropsychobiology, 2001, 43(3), 141-44, Amer. J. Med. Genetics, 2004, 131B, 51-9, Autism 2007, 11(2): 135-47, Investigacion Clinica, 2007, 48, 529-41, Nature Neuroscience, 2007, 10, 411-13, Neuroscience Letts., 2008, 433, 22-7 and Cell 2008, 135, 549-60.

SUMMARY OF THE INVENTION

In particular, the present invention provides isoxazole-thiazoles of formula I,

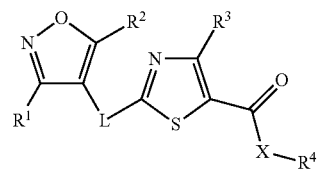

wherein
$R^1$ is selected from the group consisting of
  i) lower alkyl,
  ii) lower alkyl substituted by 1-5 halogen atoms,
  iii) aryl,
  iv) aryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl, H)N—, N(lower alkyl, lower alkyl)-lower alkyl, N(lower alkyl, H)-lower alkyl, nitro, lower alkyl-S(O)$_2$—, carboxy, carboxy-lower alkyl, lower alkyl-COO-lower alkyl, COO-lower alkyl, CO—N(lower alkyl, H)-lower alkyl, CO—N(lower alkyl, lower alkyl)-lower alkyl, CO—NH$_2$-lower alkyl and lower alkyl-CO—,
  v) heteroaryl, and
  vi) heteroaryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl, H)N—, N(lower alkyl, lower alkyl)-lower alkyl, N(lower alkyl, H)-lower alkyl, nitro, lower alkyl-S(O)$_2$—, carboxy, carboxy-lower alkyl, lower alkyl-COO-lower alkyl, lower alkyl-COO—, CO—N(lower alkyl, H)-lower alkyl, CO—N(lower alkyl, lower alkyl)-lower alkyl, CO—NH$_2$-lower alkyl and lower alkyl-CO—,
$R^2$ is H, lower alkyl or lower alkyl substituted by 1-5 substituents individually selected from halogen and hydroxy;
$R^3$ is H, lower alkyl or lower alkyl substituted by 1-5 halogen atoms;
$R^4$ is selected from the group consisting of
  i) H,
  ii) lower alkyl,
  iii) lower alkyl substituted by 1-5 substituents individually selected from acetamidyl, acetyl, acetylamino, amido, amino, carboxy, cyano, cycloalkyl, halogen, halogen-lower alkoxy, heterocyclyl, hydroxy, lower alkoxy, (lower alkyl, lower alkyl)N—, (lower alkyl, H)N—, nitro and lower alkyl-S(O)$_2$—,
  iv) aryl,
  v) heteroaryl,
  vi) heteroaryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl, H)N—, N(lower alkyl, lower alkyl)-lower alkyl, N(lower alkyl, H)-lower alkyl, nitro, lower alkyl-S(O)$_2$—, carboxy, carboxy-lower alkyl, lower alkyl-COO-lower alkyl, lower alkyl-COO—, CO—N(lower alkyl, H)-lower alkyl, CO—N(lower alkyl, lower alkyl)-lower alkyl, CO—NH$_2$-lower alkyl, and lower alkyl-CO—,
vii) cycloalkyl,
viii) cycloalkyl substituted by 1-4 substituents individually selected from halogen and hydroxy,
ix) heterocyclyl, and
x) —NR$^6$R$^7$;

R$^5$ is H, lower alkyl or lower alkyl substituted by 1-5 halogen atoms;

or R$^4$ and R$^5$ together with the nitrogen to which they are attached form a heterocyclyl or a heterocyclyl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl, H)N—, N(lower alkyl, lower alkyl)-lower alkyl, N(lower alkyl, H)-lower alkyl, nitro, lower alkyl-S(O)$_2$—, carboxy, carboxy-lower alkyl, lower alkyl-COO-lower alkyl, lower alkyl-COO—, CO—N(lower alkyl, H)-lower alkyl, CO—N(lower alkyl, lower alkyl)-lower alkyl, CO—NH$_2$-lower alkyl and lower alkyl-CO—;

R$^6$ is H or lower alkyl;
R$^7$ is H or lower alkyl; and
L is —CH$_2$—CH$_2$—, —CH$_2$—O—, —CH$_2$—NH— or —CH═CH—,
or a pharmaceutically acceptable salt or ester thereof.

DETAILED DESCRIPTION OF THE INVENTION

The present invention provides compounds of formula I and their pharmaceutically acceptable salts and esters and pharmaceutical compositions containing them. The invention also provides methods for the manufacture of such compounds and compositions. The invention further provides methods for the therapeutic and/or prophylactic treatment of diseases and disorders related to the GABA A α5 receptor. The compounds of present invention are preferably inverse agonists of GABA A α5.

The compounds of present invention and their pharmaceutically acceptable salts and esters can be used, alone or in combination with other drugs, as cognitive enhancers or for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders.

The following definitions of the general terms used in the present description apply irrespective of whether the terms in question appear alone or in combination.

The term "lower alkyl", alone or in combination with other groups, stands for a hydrocarbon radical that is linear or branched, with single or multiple branching, whereby the alkyl group in comprises 1 to 6 carbon atoms, for example, methyl (Me), ethyl (Et), propyl, isopropyl, n-butyl, i-butyl (iso-butyl), 2-butyl (sec-butyl), t-butyl (tert-butyl) and the like. Preferred "lower alkyl" are groups with 1 to 4 carbon atoms. Most preferred are methyl, ethyl, isopropyl and n-butyl.

The phrase "lower alkyl substituted by", alone or in combination with other groups, refers to lower alkyl, which is substituted by one or multiple substituents, preferably 1-5 substituents, individually selected from the group consisting of acetamidyl, acetyl, acetylamino, amido, amino, carboxy, cyano, cycloalkyl, halogen, halogen-lower alkoxy, heterocyclyl, hydroxy, lower alkoxy, (lower alkyl, lower alkyl)N—, (lower alkyl, H)N—, nitro, lower alkyl-S(O)$_2$— and the like. Preferred substituents are hydroxy, fluoro and cyclopropyl. Preferred "lower alkyl substituted by" are 1-hydroxymethyl-propyl, 2,2,2-trifluoro-1-methyl-ethyl, 2,2,2-trifluoro-ethyl, 2-hydroxy-1,1-dimethyl-ethyl, 2-hydroxy-1-hydroxymethyl-ethyl, 2-hydroxy-1-methyl-ethyl, 2-hydroxy-2-methyl-propyl, 2-hydroxy-ethyl, 2-hydroxy-propyl, cyclopropyl-methyl, cyclopropyl-methyl.

The term "halogen", alone or in combination with other groups, denotes chlorine (Cl), iodine (I), fluorine (F) and bromine (Br). Preferred halogen is fluorine.

The term "aryl", alone or in combination with other groups, refers to an aromatic carbocyclic group comprising 6 to 14, preferably 6 to 10, carbon atoms and having at least one aromatic ring or multiple condensed rings in which at least one ring is aromatic, for example phenyl (Ph), benzyl, naphthyl, biphenyl or indanyl. Preferred "aryl" is phenyl.

The phrase "aryl substituted by", alone or in combination with other groups, refers to an aryl which is substituted by one or multiple substituents, preferably 1-4 substituents, whereby substitution at each ring atom individually is possible, with a substituent individually selected from the group consisting of amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl, H)N—, N(lower alkyl, lower alkyl)-lower alkyl, N(lower alkyl, H)-lower alkyl, nitro and lower alkyl-S(O)$_2$—, carboxy, carboxy-lower alkyl, lower alkyl-COO-lower alkyl, COO-lower alkyl, CO—N(lower alkyl, H)-lower alkyl, CO—N(lower alkyl, lower alkyl)-lower alkyl, CO—NH$_2$-lower alkyl, lower alkyl-CO— and the like.

The term "heteroaryl", alone or in combination with other groups, refers to a cyclic aromatic group of having a single 4 to 8 membered ring or multiple condensed rings comprising 6 to 14, more preferably 6 to 10, ring atoms and containing 1, 2 or 3 heteroatoms, in which group at least one heterocyclic ring is aromatic. Examples of such groups include pyrrolyl, thienyl, furyl, pyrazolyl, imidazolyl, triazolyl, tetrazolyl, thiazolyl, isothiazolyl, oxazolyl, isoxazolyl, pyridinyl, pyrimidinyl, pyrazinyl, pyridazinyl, indolyl, indazolyl, quinolinyl, isoquinolinyl, benzofuryl, benzothiazolyl, benzotriazolyl, benzoimidazolyl, benzooxazinyl, benzothiazinyl, benzothienyl and the like. Preferred "heteroaryl" are pyridinyl and pyrazolyl.

The phrase "heteroaryl substituted by", alone or in combination with other groups, refers to a heteroaryl which is substituted by one or multiple substituents, preferably 1-4 substituents, whereby substitution at each ring atom individually is possible, individually selected from the group consisting of amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl, H)N—, N(lower alkyl, lower alkyl)-lower alkyl, N(lower alkyl, H)-lower alkyl, nitro and lower alkyl-S(O)$_2$—, carboxy, carboxy-lower alkyl, lower alkyl-COO-lower alkyl, COO-lower alkyl, CO—N(lower alkyl, H)-lower alkyl, CO—N(lower alkyl, lower alkyl)-lower alkyl, CO—NH$_2$-lower alkyl, lower alkyl-CO— and the like. Preferred substituents are H, F and Me. Preferred "heteroaryl substituted by" are methyl-heteroaryl, lower alkyl-heteroaryl, lower-alkyl-pyrazolyl, fluoro-heteroaryl, halogen-heteroaryl and halogen-pyridinyl. Most preferred are 1-methyl-pyrazolyl and 5-fluoro-pyridinyl.

The term "heterocyclyl", alone or in combination with other groups, refers to a 4 to 8 membered ring containing 1, 2 or 3 ring heteroatoms individually selected from N, O and S. 1 or 2 ring heteroatoms are preferred. The heterocyclyl can be part of a bicyclic spiro ring. Preferred are 4 to 6 membered heterocyclyl, more preferred 5 to 6 membered heterocyclyl, each containing 1 or 2 ring heteroatoms selected from N, O and S. Examples of such "heterocyclyl" include pyrrolidinyl (pyrrolidinyl), tetrahydrofuranyl (tetrahydrofuryl), tetrahydrothienyl, tetrahydropyridyl (tetrahydropyridinyl), tetrahydropyranyl (tetrahydropyryl), azetidyl (azetidinyl), thiazolidyl (thiazolidinyl), oxazolidyl (oxazolidinyl), piperidyl (piperidinyl), morpholinyl, thiomorpholinyl, piperazinyl, azepanyl, diazepanyl, oxazepanyl and the like. Preferred "heterocyclyl" are 2-oxa-6-aza-spiro[3.3]heptyl, tetrahydrofuryl, tetrahydropyryl, 1,1-dioxo-tetrahydrothiophenyl, 1,1-dioxo-thiomorpholinyl, morpholinyl, thiomorpholinyl and azetidinyl.

The phrase "heterocyclyl substituted by", alone or in combination with other groups, refers to a heterocyclyl, which is substituted by one or multiple substituents, preferably 1-4 substituents, whereby substitution at each ring atom individually is possible, with a substituent individually selected from the group consisting of amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl, H)N—, N(lower alkyl, lower alkyl)-lower alkyl, N(lower alkyl, H)-lower alkyl, nitro and lower alkyl-S(O)$_2$—, carboxy, carboxy-lower alkyl, lower alkyl-COO-lower alkyl, lower alkyl-COO—, CO—N(lower alkyl, H)-lower alkyl, CO—N(lower alkyl, lower alkyl)-lower alkyl, CO—NH$_2$-lower alkyl, lower alkyl-CO— and the like. Preferred substituents are hydroxy, fluoro and methyl. Preferred "heterocyclyl substituted by" are methoxy-heterocyclyl, lower-alkoxy-heterocyclyl, lower-alkoxy-azetidinyl, fluoro-heterocyclyl, halogen-heterocyclyl and halogen-azetidinyl. Most preferred are 3-methoxy-azetidinyl and 3,3-difluoro-azetidinyl.

The term "cycloalkyl", alone or in combination with other groups, refers to a 3 to 8 membered carbon ring, for example cyclopropyl, cyclobutyl, cyclopentyl, cyclohexyl, cycloheptyl or cyclooctyl. Preferred "cycloalkyl" are cyclopropyl, cyclobutyl and cyclopentyl.

The phrase "cycloalkyl substituted by", alone or in combination with other groups, refers to a cycloalkyl which is substituted by one or multiple substituents, preferably 1-4 substituents, whereby substitution at each ring atom individually is possible, with a substituent individually selected from the group consisting of halogen, halogen-lower alkoxy, halogen-lower alkyl, hydroxy, hydroxy-lower alkyl, lower alkoxy, lower alkoxy-lower alkyl, lower alkyl, (lower alkyl, lower alkyl)N—, (lower alkyl, H)N—, nitro, lower alkyl-S(O)$_2$— and the like. Preferred substituent is hydroxy. Preferred "cycloalkyl substituted by" are hydroxy-cycloalkyl and hydroxy-cyclopentyl. Most preferred is 2-hydroxy-cyclopentyl.

The term "lower alkoxy", alone or in combination with other groups, stands for a "—O-lower alkyl" radical which is linear or branched, with single or multiple branching, whereby the alkyl group in comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Preferred "lower alkoxy" are groups with 1 to 4 carbon atoms.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salts" refers to salts that are suitable for use in contact with the tissues of humans and animals without undue toxicity, irritation, allergic response, and the like. Examples of suitable salts with inorganic and organic acids are, but are not limited to, hydrochloric acid, nitric acid, sulfuric acid, phosphoric acid, sulphuric acid, citric acid, formic acid, fumaric acid, maleic acid, lactic acid, malic acid, acetic acid, succinic acid, tartaric acid, methane-sulfonic acid, p-toluenesulphonic acid, trifluoroacetic acid and the like.

The term "pharmaceutically acceptable esters" refers to a conventionally esterified compound having a carboxyl group. Examples of ester groups which are cleaved in vivo to the corresponding carboxylic acids are those in which the cleaved hydrogen is replaced with-lower alkyl which is optionally substituted with heterocyclyl, cycloalkyl, etc. Examples of substituted lower alkyl esters are those in which-lower alkyl is substituted with pyrrolidine, piperidine, morpholine, N-methylpiperazine, etc. Furthermore, the term "pharmaceutically acceptable esters" refers to a conventionally esterified compound having a hydroxy group. The hydroxy compounds can be converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which acids are non-toxic to living organisms.

The terms "pharmaceutically acceptable carrier" and "pharmaceutically acceptable auxiliary substance" refer to carriers and auxiliary substances such as diluents or excipients that are compatible with the other ingredients of the formulation and not deleterious to the recipient thereof.

"Therapeutically effective amount" means an amount that is effective to prevent, alleviate or ameliorate symptoms of disease or prolong the survival of the subject being treated.

The compounds of formula I can contain one or more asymmetric centres and can therefore occur as racemates, racemic mixtures, single enantiomers, diastereomeric mixtures and individual diastereomers. Additional asymmetric centres can be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to comprehend all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

Substituents at a double bond or a ring can be present in cis (=Z-) or trans (=E-) form, unless the stereochemistry is explicitly depicted in the corresponding compound formula I.

The term "pharmaceutical composition" encompasses a product comprising specified ingredients in pre-determined amounts or proportions, as well as any product that results, directly or indirectly, from combining specified ingredients in specified amounts. Preferably it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The following table lists abbreviations used within the present document.

TABLE 1

| abbreviations | |
|---|---|
| brine | water saturated with sodium chloride |
| BuLi | butyl lithium |
| DCM | dichloromethane |
| DMF | N,N-dimethylformamide |
| DMP | dimethyl phthalate |
| HCl | hydrochloride |
| KCl, CaCl$_2$, MgCl$_2$ | potassium chloride, calcium chloride, magnesium chloride |
| LDA | lithium diisopropylamide |
| LiOH, NaOH | lithium hydroxide, sodium hydroxide |
| Me$_3$Al | trimethylaluminium |
| MeOH, EtOH | methanol, ethanol |
| MS | mass spectrum |
| on | overnight |
| rt | room temperature |
| Seignette's salt | potassium sodium tartrate |
| TBD | 1,5,7-triazabicyclo[4.4.0]dec-5-ene |
| THF | tetrahydrofuran |

The invention also provides pharmaceutical compositions, methods of using, and methods of preparing the aforementioned compounds.

While the present invention has been described with reference to the specific embodiments thereof, it should be understood by those skilled in the art that various changes can be made and equivalents can be substituted without departing from the true spirit and scope of the invention. In addition, many modifications can be made to adapt a particular situation, material, composition of matter, process, process step or steps, to the objective spirit and scope of the present invention. All such modifications are intended to be within the scope of the claims appended hereto. All separate embodiments can be combined.

The invention therefore also relates to pharmaceutical compositions comprising a compound as defined herein and a pharmaceutically acceptable carrier and/or adjuvant.

One embodiment of the invention is a compound of formula I,

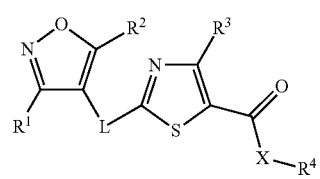

wherein
$R^1$ is selected from the group consisting of
  i) lower alkyl,
  ii) lower alkyl substituted by 1-5 halogen atoms,
  iii) aryl,
  iv) aryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl, H)N—, N(lower alkyl, lower alkyl)-lower alkyl, N(lower alkyl, H)-lower alkyl, nitro, lower alkyl-S(O)$_2$—, carboxy, carboxy-lower alkyl, lower alkyl-COO-lower alkyl, COO-lower alkyl, CO—N(lower alkyl, H)-lower alkyl, CO—N(lower alkyl, lower alkyl)-lower alkyl, CO—NH$_2$-lower alkyl and lower alkyl-CO—,
  v) heteroaryl, and
  vi) heteroaryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl, H)N—, N(lower alkyl, lower alkyl)-lower alkyl, N(lower alkyl, H)-lower alkyl, nitro, lower alkyl-S(O)$_2$—, carboxy, carboxy-lower alkyl, lower alkyl-COO-lower alkyl, lower alkyl-COO—, CO—N(lower alkyl, H)-lower alkyl, CO—N(lower alkyl, lower alkyl)-lower alkyl, CO—NH$_2$-lower alkyl and lower alkyl-CO—,
$R^2$ is H, lower alkyl or lower alkyl substituted by 1-5 substituents individually selected from halogen and hydroxy;
$R^3$ is H, lower alkyl or lower alkyl substituted by 1-5 halogen atoms;
$R^4$ is selected from the group consisting of
  i) H,
  ii) lower alkyl,
  iii) lower alkyl substituted by 1-5 substituents individually selected from acetamidyl, acetyl, acetylamino, amido, amino, carboxy, cyano, cycloalkyl, halogen, halogen-lower alkoxy, heterocyclyl, hydroxy, lower alkoxy, (lower alkyl, lower alkyl)N—, (lower alkyl, H)N—, nitro and lower alkyl-S(O)$_2$—,
  iv) aryl,
  v) heteroaryl,
  vi) heteroaryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl, H)N—, N(lower alkyl, lower alkyl)-lower alkyl, N(lower alkyl, H)-lower alkyl, nitro, lower alkyl-S(O)$_2$—, carboxy, carboxy-lower alkyl, lower alkyl-COO-lower alkyl, lower alkyl- COO—, CO—N(lower alkyl, H)-lower alkyl, CO—N(lower alkyl, lower alkyl)-lower alkyl, CO—NH$_2$-lower alkyl, and lower alkyl-CO—,
vii) cycloalkyl,
viii) cycloalkyl substituted by 1-4 substituents individually selected from halogen and hydroxy,
ix) heterocyclyl, and
x) —NR$^6$R$^7$;

R$^5$ is H, lower alkyl or lower alkyl substituted by 1-5 halogen atoms;

or R$^4$ and R$^5$ together with the nitrogen to which they are attached form a heterocyclyl or a heterocyclyl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl, H)N—, N(lower alkyl, lower alkyl)-lower alkyl, N(lower alkyl, H)-lower alkyl, nitro, lower alkyl-S(O)$_2$—, carboxy, carboxy-lower alkyl, lower alkyl-COO-lower alkyl, lower alkyl-COO—, CO—N(lower alkyl, H)-lower alkyl, CO—N(lower alkyl, lower alkyl)-lower alkyl, CO—NH$_2$-lower alkyl and lower alkyl-CO—;

R$^6$ is H or lower alkyl;
R$^7$ is H or lower alkyl; and
L is —CH$_2$—CH$_2$—, —CH$_2$—O—, —CH$_2$—NH— or —CH═CH—,
or pharmaceutically acceptable salts or esters thereof.

One certain embodiment of the invention is a compound, wherein L is —CH$_2$—CH$_2$—.

One certain embodiment of the invention is a compound, wherein L is —CH$_2$—O—.

One certain embodiment of the invention is a compound, wherein L attached to the isoxazole moiety is "-isoxazole-CH$_2$—O—".

One certain embodiment of the invention is a compound, wherein L is —CH$_2$—NH—.

One certain embodiment of the invention is a compound, wherein L attached to the isoxazole moiety is "-isoxazole-CH$_2$—NH-".

One certain embodiment of the invention is a compound, wherein L is —CH═CH—.

One certain embodiment of the invention is a compound, wherein L is —CH═CH— in cis configuration.

One certain embodiment of the invention is a compound, wherein L is —CH═CH— in trans configuration.

One certain embodiment of the invention is a compound, wherein R$^5$ is H.

One certain embodiment of the invention is a compound, wherein R$^5$ is lower alkyl.

One certain embodiment of the invention is a compound, wherein R$^5$ is lower alkyl substituted by 1-5 halogen atoms.

One certain embodiment of the invention is a compound, wherein R$^2$ is H or lower alkyl.

One certain embodiment of the invention is a compound, wherein R$^2$ is H or methyl.

One certain embodiment of the invention is a compound, wherein R$^2$ is H.

One certain embodiment of the invention is a compound, wherein R$^2$ is lower alkyl.

One certain embodiment of the invention is a compound, wherein R$^2$ is methyl.

One certain embodiment of the invention is a compound, wherein R$^3$ is H or lower alkyl.

One certain embodiment of the invention is a compound, wherein R$^3$ is H or methyl.

One certain embodiment of the invention is a compound, wherein R$^3$ is H.

One certain embodiment of the invention is a compound, wherein R$^3$ is lower alkyl.

One certain embodiment of the invention is a compound, wherein R$^3$ is methyl.

One certain embodiment of the invention is a compound, wherein R$^4$ is selected from the group consisting of
i) H,
ii) lower alkyl,
iii) lower alkyl substituted by 1-2 substituents selected from cycloalkyl, halogen and hydroxy,
iv) heteroaryl substituted by 1-2 lower alkyl groups,
v) cycloalkyl,
vi) cycloalkyl substituted by 1-2 hydroxy groups,
vii) heterocyclyl, and
viii) —NR$^6$R$^7$, wherein R$^6$ and R$^7$ are each individually selected from lower alkyl.

One certain embodiment of the invention is a compound, wherein R$^4$ is selected from the group consisting of
i) lower alkyl,
ii) lower alkyl substituted by 1-2 substituents individually selected from cycloalkyl and hydroxy,
iii) cycloalkyl, and
iv) heterocyclyl.

One certain embodiment of the invention is a compound, wherein R$^4$ is isopropyl, 2-hydroxy-ethyl, 2-hydroxy-1-hydroxymethyl-ethyl, 2-hydroxy-1-methyl-ethyl, 2-hydroxy-ethyl, cyclopropyl-methyl, cyclobutyl or 1,1-dioxo-tetrahydrothiophenyl.

One certain embodiment of the invention is a compound, wherein R$^4$ is H.

One certain embodiment of the invention is a compound, wherein R$^4$ is lower alkyl.

One certain embodiment of the invention is a compound, wherein R$^4$ is methyl.

One certain embodiment of the invention is a compound, wherein R$^4$ is ethyl.

One certain embodiment of the invention is a compound, wherein R$^4$ is isopropyl.

One certain embodiment of the invention is a compound, wherein R$^4$ is lower alkyl substituted by 1-2 substituents individually selected from cycloalkyl, halogen and hydroxy.

One certain embodiment of the invention is a compound, wherein R$^4$ is 1-hydroxymethyl-propyl.

One certain embodiment of the invention is a compound, wherein R$^4$ is 2,2,2-trifluoro-1-methyl-ethyl.

One certain embodiment of the invention is a compound, wherein R$^4$ is 2-hydroxy-1-methyl-ethyl.

One certain embodiment of the invention is a compound, wherein R$^4$ is 2,2,2-trifluoro-ethyl.

One certain embodiment of the invention is a compound, wherein R$^4$ is 2-hydroxy-1,1-dimethyl-ethyl.

One certain embodiment of the invention is a compound, wherein R$^4$ is 2-hydroxy-1-hydroxymethyl-ethyl.

One certain embodiment of the invention is a compound, wherein R$^4$ is 2-hydroxy-2-methyl-propyl.

One certain embodiment of the invention is a compound, wherein R$^4$ is 2-hydroxy-ethyl.

One certain embodiment of the invention is a compound, wherein R$^4$ is 2-hydroxy-propyl.

One certain embodiment of the invention is a compound, wherein R$^4$ is cyclopropyl-methyl.

One certain embodiment of the invention is a compound, wherein R$^4$ is H, 2-hydroxy-cyclopentyl, 1-hydroxymethyl-propyl, 2,2,2-trifluoro-1-methyl-ethyl, 2-hydroxy-1-methyl-ethyl, 1,1-dioxo-tetrahydrothiophenyl, 1-methyl-1-pyrazolyl, 2,2,2-trifluoro-ethyl, 2-hydroxy-1,1-dimethyl-ethyl, 2-hydroxy-1-hydroxymethyl-ethyl, 2-hydroxy-2-methyl-propyl, 2-hydroxy-ethyl, 2-hydroxy-propyl, cyclobutyl, cyclopropyl, cyclopropyl-methyl, ethyl, H, isopropyl, methyl, morpholinyl, —N(CH$_3$)$_2$, tetrahydrofuranyl or tetrahydropyranyl.

One certain embodiment of the invention is a compound, wherein $R^4$ is heteroaryl substituted by one or multiple lower alkyl.

One certain embodiment of the invention is a compound, wherein $R^4$ is 1-methyl-1-pyrazolyl.

One certain embodiment of the invention is a compound, wherein $R^4$ is cycloalkyl.

One certain embodiment of the invention is a compound, wherein $R^4$ is cyclobutyl.

One certain embodiment of the invention is a compound, wherein $R^4$ is cyclopropyl.

One certain embodiment of the invention is a compound, wherein $R^4$ is cycloalkyl substituted by 1-4 hydroxy groups.

One certain embodiment of the invention is a compound, wherein $R^4$ is 2-hydroxy-cyclopentyl.

One certain embodiment of the invention is a compound, wherein $R^4$ is heterocyclyl.

One certain embodiment of the invention is a compound, wherein $R^4$ is 1,1-dioxo-tetrahydrothiophenyl.

One certain embodiment of the invention is a compound, wherein $R^4$ is morpholinyl.

One certain embodiment of the invention is a compound, wherein $R^4$ is tetrahydrofuranyl.

One certain embodiment of the invention is a compound, wherein $R^4$ is tetrahydropyranyl.

One certain embodiment of the invention is a compound, wherein $R^4$ is —$NR^6R^7$, wherein $R^6$ and $R^7$ are each individually selected from lower alkyl.

One certain embodiment of the invention is a compound, wherein $R^4$ is —N(CH$_3$)$_2$.

One certain embodiment of the invention is a compound, wherein $R^4$ and $R^5$ together with the nitrogen to which they are attached form a heterocyclyl or a heterocyclyl substituted by 1-4 substituents individually selected from halogen and lower alkoxy.

One certain embodiment of the invention is a compound, wherein $R^4$ and $R^5$ together with the nitrogen to which they are attached form a thiomorpholinyl, 1,1-dioxo-thiomorpholinyl, morpholinyl, 3,3-difluoro-azetidinyl, 3-methoxy-azetidinyl, azetidinyl or 2-oxa-6-aza-spiro[3.3]heptyl.

One certain embodiment of the invention is a compound, wherein $R^4$ and $R^5$ together with the nitrogen to which they are attached form a heterocyclyl.

One certain embodiment of the invention is a compound, wherein $R^4$ and $R^5$ together with the nitrogen to which they are attached form a thiomorpholinyl, morpholinyl, azetidinyl or 2-oxa-6-aza-spiro[3.3]heptyl.

One certain embodiment of the invention is a compound, wherein $R^4$ and $R^5$ together with the nitrogen to which they are attached form a thiomorpholinyl.

One certain embodiment of the invention is a compound, wherein $R^4$ and $R^5$ together with the nitrogen to which they are attached form a morpholinyl.

One certain embodiment of the invention is a compound, wherein $R^4$ and $R^5$ together with the nitrogen to which they are attached form a azetidinyl.

One certain embodiment of the invention is a compound, wherein $R^4$ and $R^5$ together with the nitrogen to which they are attached form a 2-oxa-6-aza-spiro[3.3]heptyl.

One certain embodiment of the invention is a compound, wherein $R^4$ and $R^5$ together with the nitrogen to which they are attached form a 1,1-dioxo-thiomorpholinyl.

One certain embodiment of the invention is a compound, wherein $R^4$ and $R^5$ together with the nitrogen to which they are attached form a heterocyclyl substituted by 1-4 substituents individually selected from halogen and lower alkoxy.

One certain embodiment of the invention is a compound, wherein $R^4$ and $R^5$ together with the nitrogen to which they are attached form a 1,1-dioxo-thiomorpholinyl, 3,3-difluoro-azetidinyl, or 3-methoxy-azetidinyl.

One certain embodiment of the invention is a compound, wherein $R^4$ and $R^5$ together with the nitrogen to which they are attached form a 3,3-difluoro-azetidinyl.

One certain embodiment of the invention is a compound, wherein $R^4$ and $R^5$ together with the nitrogen to which they are attached form a 3-methoxy-azetidinyl.

One certain embodiment of the invention is a compound, wherein $R^6$ is methyl.

One certain embodiment of the invention is a compound, wherein $R^7$ is methyl.

One certain embodiment of the invention is a compound, selected from the group consisting of
(1,1-Dioxothiomorpholin-4-yl)-(2-{(E)-2-[3-(5-fluoro-pyridin-2-yl)-5-methyl-isoxazol-4-yl]-vinyl}-thiazol-5-yl)-methanone,
(2-{(E)-2-[3-(5-Fluoro-pyridin-2-yl)-5-methyl-isoxazol-4-yl]-vinyl}-thiazol-5-yl)-morpholin-4-yl-methanone,
(2-{(E)-2-[3-(5-Fluoro-pyridin-2-yl)-5-methyl-isoxazol-4-yl]-vinyl}-thiazol-5-yl)-thiomorpholin-4-yl-methanone,
(2-{2-[3-(5-Fluoro-pyridin-2-yl)-5-methyl-isoxazol-4-yl]-ethyl}-4-methyl-thiazol-5-yl)-thiomorpholin-4-yl-methanone,
{2-[(E)-2-(3-Butyl-5-methyl-isoxazol-4-yl)-vinyl]-4-methyl-thiazol-5-yl}-(3,3-difluoro-azetidin-1-yl)-methanone,
{2-[(E)-2-(3-Butyl-5-methyl-isoxazol-4-yl)-vinyl]-4-methyl-thiazol-5-yl}-(3-methoxy-azetidin-1-yl)-methanone,
{2-[(E)-2-(3-Butyl-5-methyl-isoxazol-4-yl)-vinyl]-4-methyl-thiazol-5-yl}-morpholin-4-yl-methanone,
{2-[(E)-2-(3-Butyl-5-methyl-isoxazol-4-yl)-vinyl]-4-methyl-thiazol-5-yl}-(2-oxa-6-aza-spiro[3.3]hept-6-yl)-methanone,
{4-Methyl-2-[2-(5-methyl-3-pyridin-2-yl-isoxazol-4-yl)-ethyl]-thiazol-5-yl}-thiomorpholin-4-yl-methanone,
2-(3-Butyl-5-methyl-isoxazol-4-ylmethoxy)-thiazole-5-carboxylic acid isopropylamide,
2-(3-Butyl-5-methyl-isoxazol-4-ylmethoxy)-thiazole-5-carboxylic acid (2-hydroxy-1-methyl-ethyl)-amide,
2-(3-Butyl-5-methyl-isoxazol-4-ylmethoxy)-thiazole-5-carboxylic acid (2-hydroxy-ethyl)-amide,
2-(5-Methyl-3-phenyl-isoxazol-4-ylmethoxy)-thiazole-5-carboxylic acid isopropylamide,
2-(5-Methyl-3-phenyl-isoxazol-4-ylmethoxy)-thiazole-5-carboxylic acid (tetrahydro-pyran-4-yl)-amide,
2-(5-Methyl-3-phenyl-isoxazol-4-ylmethoxy)-thiazole-5-carboxylic acid (2-hydroxy-1-methyl-ethyl)-amide,
2-(5-Methyl-3-phenyl-isoxazol-4-ylmethoxy)-thiazole-5-carboxylic acid (2-hydroxy-ethyl)-amide,
2-(5-Methyl-3-phenyl-isoxazol-4-ylmethoxy)-thiazole-5-carboxylic acid (2-hydroxy-1,1-dimethyl-ethyl)-amide,
2-[(5-Methyl-3-phenyl-isoxazol-4-ylmethyl)-amino]-thiazole-5-carboxylic acid isopropylamide,
2-[(5-Methyl-3-phenyl-isoxazol-4-ylmethyl)-amino]-thiazole-5-carboxylic acid (tetrahydro-pyran-4-yl)-amide,
2-[(E)-2-(3-Butyl-5-methyl-isoxazol-4-yl)-vinyl]-4-methyl-thiazole-5-carboxylic acid isopropylamide, 2-[(E)-2-(3-Butyl-5-methyl-isoxazol-4-yl)-vinyl]-4-methyl-thiazole-5-carboxylic acid (tetrahydro-furan-3-yl)-amide,
2-[(E)-2-(3-Butyl-5-methyl-isoxazol-4-yl)-vinyl]-4-methyl-thiazole-5-carboxylic acid (2-hydroxy-ethyl)-amide,
2-[(E)-2-(3-Butyl-5-methyl-isoxazol-4-yl)-vinyl]-4-methyl-thiazole-5-carboxylic acid (tetrahydro-pyran-4-yl)-amide,
2-[(E)-2-(3-Butyl-5-methyl-isoxazol-4-yl)-vinyl]-4-methyl-thiazole-5-carboxylic acid (2-hydroxy-1-methyl-ethyl)-amide,
2-[(E)-2-(3-Butyl-5-methyl-isoxazol-4-yl)-vinyl]-4-methyl-thiazole-5-carboxylic acid (2-hydroxy-1-hydroxymethyl-ethyl)-amide,
2-[(E)-2-(3-Butyl-5-methyl-isoxazol-4-yl)-vinyl]-4-methyl-thiazole-5-carboxylic acid amide,
2-[(E)-2-(3-Butyl-5-methyl-isoxazol-4-yl)-vinyl]-4-methyl-thiazole-5-carboxylic acid N',N'-dimethyl-hydrazide,
2-[(E)-2-(3-Butyl-5-methyl-isoxazol-4-yl)-vinyl]-4-methyl-thiazole-5-carboxylic acid morpholin-4-ylamide,
2-[(E)-2-(3-Butyl-5-methyl-isoxazol-4-yl)-vinyl]-4-methyl-thiazole-5-carboxylic acid (1-hydroxymethyl-propyl)-amide,
2-[(E)-2-(3-Butyl-5-methyl-isoxazol-4-yl)-vinyl]-4-methyl-thiazole-5-carboxylic acid ((R)-1-hydroxymethyl-propyl)-amide,
2-[(E)-2-(3-Butyl-5-methyl-isoxazol-4-yl)-vinyl]-4-methyl-thiazole-5-carboxylic acid ((S)-1-hydroxymethyl-propyl)-amide,
2-[(E)-2-(3-Butyl-5-methyl-isoxazol-4-yl)-vinyl]-4-methyl-thiazole-5-carboxylic acid ((R)-2,2,2-trifluoro-1-methyl-ethyl)-amide,
2-[(E)-2-(3-Butyl-5-methyl-isoxazol-4-yl)-vinyl]-4-methyl-thiazole-5-carboxylic acid ((1S,2S)-2-hydroxy-cyclopentyl)-amide,
2-[(E)-2-(3-Butyl-5-methyl-isoxazol-4-yl)-vinyl]-4-methyl-thiazole-5-carboxylic acid (1-methyl-1-pyrazol-4-yl)-amide,
2-[(E)-2-(3-Butyl-5-methyl-isoxazol-4-yl)-vinyl]-4-methyl-thiazole-5-carboxylic acid cyclopropylamide,
2-[(E)-2-(3-Butyl-5-methyl-isoxazol-4-yl)-vinyl]-4-methyl-thiazole-5-carboxylic acid ((1SR,2SR)-2-hydroxy-cyclopentyl)-amide,
2-[(E)-2-(3-Butyl-5-methyl-isoxazol-4-yl)-vinyl]-4-methyl-thiazole-5-carboxylic acid cyclobutylamide,
2-[(E)-2-(3-Butyl-5-methyl-isoxazol-4-yl)-vinyl]-4-methyl-thiazole-5-carboxylic acid cyclopropylmethyl-amide,
2-[(E)-2-(3-Butyl-5-methyl-isoxazol-4-yl)-vinyl]-4-methyl-thiazole-5-carboxylic acid (2-hydroxy-1,1-dimethyl-ethyl)-amide,
2-[(E)-2-(3-Butyl-5-methyl-isoxazol-4-yl)-vinyl]-4-methyl-thiazole-5-carboxylic acid (1,1-dioxo-tetrahydrothiophen-3-yl)-amide,
2-[(E)-2-(3-Butyl-5-methyl-isoxazol-4-yl)-vinyl]-4-methyl-thiazole-5-carboxylic acid (2,2,2-trifluoro-ethyl)-amide,
2-[(E)-2-(3-Butyl-5-methyl-isoxazol-4-yl)-vinyl]-4-methyl-thiazole-5-carboxylic acid ethylamide,
2-[(E)-2-(3-Butyl-5-methyl-isoxazol-4-yl)-vinyl]-4-methyl-thiazole-5-carboxylic acid methylamide,
2-[(E)-2-(3-Butyl-5-methyl-isoxazol-4-yl)-vinyl]-thiazole-5-carboxylic acid isopropylamide,
2-[(E)-2-(3-Butyl-5-methyl-isoxazol-4-yl)-vinyl]-thiazole-5-carboxylic acid (2-hydroxy-ethyl)-amide,
2-[(E)-2-(5-Methyl-3-phenyl-isoxazol-4-yl)-vinyl]-thiazole-5-carboxylic acid (tetrahydro-pyran-4-yl)-amide,
2-[(E)-2-(5-Methyl-3-phenyl-isoxazol-4-yl)-vinyl]-thiazole-5-carboxylic acid ((R)-tetrahydro-furan-3-yl)-amide,
2-[(E)-2-(5-Methyl-3-phenyl-isoxazol-4-yl)-vinyl]-thiazole-5-carboxylic acid ((S)-tetrahydro-furan-3-yl)-amide,
2-[(E)-2-(5-Methyl-3-phenyl-isoxazol-4-yl)-vinyl]-thiazole-5-carboxylic acid isopropylamide,
2-[(E)-2-(5-Methyl-3-phenyl-isoxazol-4-yl)-vinyl]-thiazole-5-carboxylic acid (2-hydroxy-1-methyl-ethyl)-amide,
2-[(E)-2-(5-Methyl-3-phenyl-isoxazol-4-yl)-vinyl]-thiazole-5-carboxylic acid (2-hydroxy-ethyl)-amide,
2-[(Z)-2-(3-Butyl-5-methyl-isoxazol-4-yl)-vinyl]-4-methyl-thiazole-5-carboxylic acid (2-hydroxy-ethyl)-amide,
2-[2-(3-Butyl-5-methyl-isoxazol-4-yl)-ethyl]-4-methyl-thiazole-5-carboxylic acid isopropylamide,
2-[2-(3-Butyl-5-methyl-isoxazol-4-yl)-ethyl]-4-methyl-thiazole-5-carboxylic acid (2-hydroxy-2-methyl-propyl)-amide,
2-[2-(3-Butyl-5-methyl-isoxazol-4-yl)-ethyl]-4-methyl-thiazole-5-carboxylic acid (2-hydroxy-1-methyl-ethyl)-amide,
2-[2-(3-Butyl-5-methyl-isoxazol-4-yl)-ethyl]-4-methyl-thiazole-5-carboxylic acid (tetrahydro-pyran-4-yl)-amide,
2-[2-(3-Butyl-5-methyl-isoxazol-4-yl)-ethyl]-4-methyl-thiazole-5-carboxylic acid (tetrahydro-furan-3-yl)-amide,
2-[2-(3-Butyl-5-methyl-isoxazol-4-yl)-ethyl]-4-methyl-thiazole-5-carboxylic acid (2-hydroxy-1-hydroxymethyl-ethyl)-amide,
2-[2-(3-Butyl-5-methyl-isoxazol-4-yl)-ethyl]-4-methyl-thiazole-5-carboxylic acid (S-2-hydroxy-1-methyl-ethyl)-amide,
2-[2-(3-Butyl-5-methyl-isoxazol-4-yl)-ethyl]-4-methyl-thiazole-5-carboxylic acid ((R)-2-hydroxy-1-methyl-ethyl)-amide,
2-[2-(3-Butyl-5-methyl-isoxazol-4-yl)-ethyl]-4-methyl-thiazole-5-carboxylic acid (2-hydroxy-propyl)-amide,
2-[2-(3-Butyl-5-methyl-isoxazol-4-yl)-ethyl]-thiazole-5-carboxylic acid isopropylamide,
2-[2-(3-Butyl-5-methyl-isoxazol-4-yl)-ethyl]-thiazole-5-carboxylic acid (2-hydroxy-1-methyl-ethyl)-amide,
2-[2-(3-Butyl-5-methyl-isoxazol-4-yl)-ethyl]-thiazole-5-carboxylic acid (tetrahydro-pyran-4-yl)-amide,
2-[2-(3-Butyl-5-methyl-isoxazol-4-yl)-ethyl]-thiazole-5-carboxylic acid (tetrahydro-furan-3-yl)-amide,
2-[2-(3-Butyl-5-methyl-isoxazol-4-yl)-ethyl]-thiazole-5-carboxylic acid ((S)-2-hydroxy-1-methyl-ethyl)-amide,
2-[2-(3-Butyl-5-methyl-isoxazol-4-yl)-ethyl]-thiazole-5-carboxylic acid (2-hydroxy-propyl)-amide,
4-Methyl-2-[2-(5-methyl-3-phenyl-isoxazol-4-yl)-ethyl]-thiazole-5-carboxylic acid isopropylamide,
2-[2-(5-Methyl-3-phenyl-isoxazol-4-yl)-ethyl]-thiazole-5-carboxylic acid isopropylamide,
2-[2-(5-Methyl-3-pyridin-2-yl-isoxazol-4-yl)-ethyl]-thiazole-5-carboxylic acid isopropylamide,
2-[2-(5-Methyl-3-pyridin-2-yl-isoxazol-4-yl)-ethyl]-thiazole-5-carboxylic acid cyclopropylamide,
2-[2-(5-Methyl-3-pyridin-2-yl-isoxazol-4-yl)-ethyl]-thiazole-5-carboxylic acid (tetrahydro-pyran-4-yl)-amide,
2-[2-(5-Methyl-3-pyridin-2-yl-isoxazol-4-yl)-ethyl]-thiazole-5-carboxylic acid amide,
2-[2-(5-Methyl-3-pyridin-2-yl-isoxazol-4-yl)-ethyl]-thiazole-5-carboxylic acid cyclopropylmethyl-amide,
2-[2-(5-Methyl-3-pyridin-2-yl-isoxazol-4-yl)-ethyl]-thiazole-5-carboxylic acid (1,1-dioxo-tetrahydrothiophen-3-yl)-amide,
2-[2-(5-Methyl-3-pyridin-2-yl-isoxazol-4-yl)-ethyl]-thiazole-5-carboxylic acid (2,2,2-trifluoro-ethyl)-amide,
2-[2-(5-Methyl-3-pyridin-2-yl-isoxazol-4-yl)-ethyl]-thiazole-5-carboxylic acid (2-hydroxy-ethyl)-amide,
2-{(E)-2-[3-(5-Fluoro-pyridin-2-yl)-5-methyl-isoxazol-4-yl]-vinyl}-4-methyl-thiazole-5-carboxylic acid isopropylamide, 2-{(E)-2-[3-(5-Fluoro-pyridin-2-yl)-5-methyl-isoxazol-4-yl]-vinyl}-4-methyl-thiazole-5-carboxylic acid (tetrahydro-pyran-4-yl)-amide,
2-{(E)-2-[3-(5-Fluoro-pyridin-2-yl)-5-methyl-isoxazol-4-yl]-vinyl}-4-methyl-thiazole-5-carboxylic acid cyclopropylamide,
2-{(E)-2-[3-(5-Fluoro-pyridin-2-yl)-5-methyl-isoxazol-4-yl]-vinyl}-4-methyl-thiazole-5-carboxylic acid (2-hydroxy-1,1-dimethyl-ethyl)-amide,
2-{(E)-2-[3-(5-Fluoro-pyridin-2-yl)-5-methyl-isoxazol-4-yl]-vinyl}-4-methyl-thiazole-5-carboxylic acid cyclopropylmethyl-amide,
2-{(E)-2-[3-(5-Fluoro-pyridin-2-yl)-5-methyl-isoxazol-4-yl]-vinyl}-4-methyl-thiazole-5-carboxylic acid amide,
2-{(E)-2-[3-(5-Fluoro-pyridin-2-yl)-5-methyl-isoxazol-4-yl]-vinyl}-thiazole-5-carboxylic acid (tetrahydro-pyran-4-yl)-amide,
2-{(E)-2-[3-(5-Fluoro-pyridin-2-yl)-5-methyl-isoxazol-4-yl]-vinyl}-thiazole-5-carboxylic acid isopropylamide,
2-{(E)-2-[3-(5-Fluoro-pyridin-2-yl)-5-methyl-isoxazol-4-yl]-vinyl}-thiazole-5-carboxylic acid cyclopropylamide,
2-{(E)-2-[3-(5-Fluoro-pyridin-2-yl)-5-methyl-isoxazol-4-yl]-vinyl}-thiazole-5-carboxylic acid (2-hydroxy-1,1-dimethyl-ethyl)-amide,
2-{(E)-2-[3-(5-Fluoro-pyridin-2-yl)-5-methyl-isoxazol-4-yl]-vinyl}-thiazole-5-carboxylic acid amide,
2-{(E)-2-[3-(5-Fluoro-pyridin-2-yl)-5-methyl-isoxazol-4-yl]-vinyl}-thiazole-5-carboxylic acid cyclopropylmethyl-amide,
2-{(E)-2-[3-(5-Fluoro-pyridin-2-yl)-5-methyl-isoxazol-4-yl]-vinyl}-thiazole-5-carboxylic acid (2,2,2-trifluoro-ethyl)-amide,
2-{(E)-2-[3-(5-Fluoro-pyridin-2-yl)-5-methyl-isoxazol-4-yl]-vinyl}-thiazole-5-carboxylic acid (2-hydroxy-ethyl)-amide,
2-{(E)-2-[3-(5-Fluoro-pyridin-2-yl)-5-methyl-isoxazol-4-yl]-vinyl}-thiazole-5-carboxylic acid ethylamide,
2-{(E)-2-[3-(5-Fluoro-pyridin-2-yl)-5-methyl-isoxazol-4-yl]-vinyl}-thiazole-5-carboxylic acid methylamide,
2-{(E)-2-[3-(5-Fluoro-pyridin-2-yl)-isoxazol-4-yl]-vinyl}-4-methyl-thiazole-5-carboxylic acid (tetrahydro-pyran-4-yl)-amide,
2-{(E)-2-[3-(5-Fluoro-pyridin-2-yl)-isoxazol-4-yl]-vinyl}-4-methyl-thiazole-5-carboxylic acid cyclopropylamide,
2-{(E)-2-[3-(5-Fluoro-pyridin-2-yl)-isoxazol-4-yl]-vinyl}-4-methyl-thiazole-5-carboxylic acid cyclopropylmethyl-amide,
2-{2-[3-(5-Fluoro-pyridin-2-yl)-5-methyl-isoxazol-4-yl]-ethyl}-4-methyl-thiazole-5-carboxylic acid (tetrahydro-pyran-4-yl)-amide,
2-{2-[3-(5-Fluoro-pyridin-2-yl)-5-methyl-isoxazol-4-yl]-ethyl}-4-methyl-thiazole-5-carboxylic acid isopropylamide,
2-{2-[3-(5-Fluoro-pyridin-2-yl)-5-methyl-isoxazol-4-yl]-ethyl}-4-methyl-thiazole-5-carboxylic acid cyclopropylamide,
2-{2-[3-(5-Fluoro-pyridin-2-yl)-5-methyl-isoxazol-4-yl]-ethyl}-4-methyl-thiazole-5-carboxylic acid cyclopropylmethyl-amide,
2-{2-[3-(5-Fluoro-pyridin-2-yl)-5-methyl-isoxazol-4-yl]-ethyl}-4-methyl-thiazole-5-carboxylic acid (2,2,2-trifluoro-ethyl)-amide,
2-{2-[3-(5-Fluoro-pyridin-2-yl)-5-methyl-isoxazol-4-yl]-ethyl}-4-methyl-thiazole-5-carboxylic acid (2-hydroxy-ethyl)-amide,
2-{2-[3-(5-Fluoro-pyridin-2-yl)-5-methyl-isoxazol-4-yl]-ethyl}-4-methyl-thiazole-5-carboxylic acid ethylamide,
2-{2-[3-(5-Fluoro-pyridin-2-yl)-5-methyl-isoxazol-4-yl]-ethyl}-4-methyl-thiazole-5-carboxylic acid methylamide,
2-{2-[3-(5-Fluoro-pyridin-2-yl)-5-methyl-isoxazol-4-yl]-ethyl}-thiazole-5-carboxylic acid (tetrahydro-pyran-4-yl)-amide,
2-{2-[3-(5-Fluoro-pyridin-2-yl)-5-methyl-isoxazol-4-yl]-ethyl}-thiazole-5-carboxylic acid isopropylamide,
2-{2-[3-(5-Fluoro-pyridin-2-yl)-5-methyl-isoxazol-4-yl]-ethyl}-thiazole-5-carboxylic acid cyclopropylamide,
2-{2-[3-(5-Fluoro-pyridin-2-yl)-5-methyl-isoxazol-4-yl]-ethyl}-thiazole-5-carboxylic acid cyclopropylmethyl-amide,
2-{2-[3-(5-Fluoro-pyridin-2-yl)-5-methyl-isoxazol-4-yl]-ethyl}-thiazole-5-carboxylic acid (2,2,2-trifluoro-ethyl)-amide,
2-{2-[3-(5-Fluoro-pyridin-2-yl)-5-methyl-isoxazol-4-yl]-ethyl}-thiazole-5-carboxylic acid (2-hydroxy-ethyl)-amide,
2-{2-[3-(5-Fluoro-pyridin-2-yl)-5-methyl-isoxazol-4-yl]-ethyl}-thiazole-5-carboxylic acid ethylamide,
2-{2-[3-(5-Fluoro-pyridin-2-yl)-5-methyl-isoxazol-4-yl]-ethyl}-thiazole-5-carboxylic acid methylamide,
4-Methyl-2-[(E)-2-(5-methyl-3-phenyl-isoxazol-4-yl)-vinyl]-thiazole-5-carboxylic acid isopropylamide,
4-Methyl-2-[(E)-2-(5-methyl-3-phenyl-isoxazol-4-yl)-vinyl]-thiazole-5-carboxylic acid (tetrahydro-furan-3-yl)-amide,
4-Methyl-2-[(E)-2-(5-methyl-3-phenyl-isoxazol-4-yl)-vinyl]-thiazole-5-carboxylic acid (2-hydroxy-ethyl)-amide,
4-Methyl-2-[2-(3-pyridin-2-yl-isoxazol-4-yl)-ethyl]-thiazole-5-carboxylic acid (tetrahydro-pyran-4-yl)-amide,
4-Methyl-2-[2-(3-pyridin-2-yl-isoxazol-4-yl)-ethyl]-thiazole-5-carboxylic acid (2,2,2-trifluoro-ethyl)-amide,
4-Methyl-2-[2-(5-methyl-3-phenyl-isoxazol-4-yl)-ethyl]-thiazole-5-carboxylic acid (tetrahydro-furan-3(R)-yl)-amide,
4-Methyl-2-[2-(5-methyl-3-phenyl-isoxazol-4-yl)-ethyl]-thiazole-5-carboxylic acid (tetrahydro-furan-3(S)-yl)-amide,
4-Methyl-2-[2-(5-methyl-3-phenyl-isoxazol-4-yl)-ethyl]-thiazole-5-carboxylic acid (2-hydroxy-1-methyl-ethyl)-amide,
4-Methyl-2-[2-(5-methyl-3-phenyl-isoxazol-4-yl)-ethyl]-thiazole-5-carboxylic acid (2-hydroxy-2-methyl-propyl)-amide,
4-Methyl-2-[2-(5-methyl-3-phenyl-isoxazol-4-yl)-ethyl]-thiazole-5-carboxylic acid (tetrahydro-pyran-4-yl)-amide,
4-Methyl-2-[2-(5-methyl-3-phenyl-isoxazol-4-yl)-ethyl]-thiazole-5-carboxylic acid amide,
4-Methyl-2-[2-(5-methyl-3-pyridin-2-yl-isoxazol-4-yl)-ethyl]-thiazole-5-carboxylic acid (tetrahydro-pyran-4-yl)-amide,
4-Methyl-2-[2-(5-methyl-3-pyridin-2-yl-isoxazol-4-yl)-ethyl]-thiazole-5-carboxylic acid isopropylamide,
4-Methyl-2-[2-(5-methyl-3-pyridin-2-yl-isoxazol-4-yl)-ethyl]-thiazole-5-carboxylic acid cyclopropylamide,
4-Methyl-2-[2-(5-methyl-3-pyridin-2-yl-isoxazol-4-yl)-ethyl]-thiazole-5-carboxylic acid cyclopropylmethyl-amide,
4-Methyl-2-[2-(5-methyl-3-pyridin-2-yl-isoxazol-4-yl)-ethyl]-thiazole-5-carboxylic acid (2,2,2-trifluoro-ethyl)-amide,
4-Methyl-2-[2-(5-methyl-3-pyridin-2-yl-isoxazol-4-yl)-ethyl]-thiazole-5-carboxylic acid (2-hydroxy-ethyl)-amide,
4-Methyl-2-[2-(5-methyl-3-pyridin-2-yl-isoxazol-4-yl)-ethyl]-thiazole-5-carboxylic acid ethylamide, 4-Methyl-2-[2-(5-methyl-3-pyridin-2-yl-isoxazol-4-yl)-ethyl]-thiazole-5-carboxylic acid methylamide, 4-Methyl-2-[2-(5-methyl-3-pyridin-2-yl-isoxazol-4-yl)-ethyl]-thiazole-5-carboxylic acid amide, and Azetidin-1-yl-{2-[(E)-2-(3-butyl-5-methyl-isoxazol-4-yl)-vinyl]-4-methyl-thiazol-5-yl}-methanone, or pharmaceutically acceptable salts or esters thereof.

One certain embodiment of the invention is a compound selected from the group consisting of 2-[(E)-2-(3-Butyl-5-methyl-isoxazol-4-yl)-vinyl]-4-methyl-thiazole-5-carboxylic acid (2-hydroxy-ethyl)-amide, 2-[(E)-2-(3-Butyl-5-methyl-isoxazol-4-yl)-vinyl]-4-methyl-thiazole-5-carboxylic acid cyclobutylamide, 2-[(E)-2-(3-Butyl-5-methyl-isoxazol-4-yl)-vinyl]-4-methyl-thiazole-5-carboxylic acid cyclopropylmethyl-amide, 2-[(E)-2-(3-Butyl-5-methyl-isoxazol-4-yl)-vinyl]-4-methyl-thiazole-5-carboxylic acid (1,1-dioxo-tetrahydrothiophen-3-yl)-amide, 2-[(E)-2-(5-Methyl-3-phenyl-isoxazol-4-yl)-vinyl]-thiazole-5-carboxylic acid (2-hydroxy-1-methyl-ethyl)-amide, 2-[2-(3-Butyl-5-methyl-isoxazol-4-yl)-ethyl]-4-methyl-thiazole-5-carboxylic acid (2-hydroxy-1-hydroxymethyl-ethyl)-amide, 4-Methyl-2-[2-(5-methyl-3-phenyl-isoxazol-4-yl)-ethyl]-thiazole-5-carboxylic acid isopropylamide, 2-[2-(5-Methyl-3-phenyl-isoxazol-4-yl)-ethyl]-thiazole-5-carboxylic acid isopropylamide, 2-{(E)-2-[3-(5-Fluoro-pyridin-2-yl)-5-methyl-isoxazol-4-yl]-vinyl}-4-methyl-thiazole-5-carboxylic acid isopropylamide, 2-{(E)-2-[3-(5-Fluoro-pyridin-2-yl)-5-methyl-isoxazol-4-yl]-vinyl}-thiazole-5-carboxylic acid isopropylamide, 4-Methyl-2-[2-(5-methyl-3-pyridin-2-yl-isoxazol-4-yl)-ethyl]-thiazole-5-carboxylic acid isopropylamide, and 4-Methyl-2-[2-(5-methyl-3-pyridin-2-yl-isoxazol-4-yl)-ethyl]-thiazole-5-carboxylic acid (2-hydroxy-ethyl)-amide, or pharmaceutically acceptable salts or esters thereof.

One certain embodiment of the invention is 2-[(E)-2-(3-Butyl-5-methyl-isoxazol-4-yl)-vinyl]-4-methyl-thiazole-5-carboxylic acid (2-hydroxy-ethyl)-amide, or pharmaceutically acceptable salts or esters thereof.

One certain embodiment of the invention is a compound of formula II,

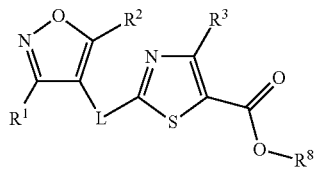

wherein R', $R^2$, $R^3$ are as defined herein and
$R^8$ is selected from the group consisting of
  i) H,
  ii) lower alkyl,
  iii) lower alkyl substituted by 1-5 substituents individually selected from acetamidyl, acetyl, acetylamino, amido, amino, carboxy, cyano, cycloalkyl, halogen, halogen-lower alkoxy, heterocyclyl, hydroxy, lower alkoxy, (lower alkyl, lower alkyl)N—, (lower alkyl, H)N—, nitro and lower alkyl-S(O)$_2$—; and L is —CH$_2$—CH$_2$—, —CH$_2$—O—, —CH$_2$—NH—, or —CH═CH—, or pharmaceutically acceptable salts or esters thereof.

One certain embodiment of the invention is a compound of formula II, wherein $R^1$ is selected from the group consisting of lower alkyl, aryl, heteroaryl and heteroaryl substituted by 1-2 halogen; $R^2$ is lower alkyl; $R^3$ is H or lower alkyl; $R^8$ is selected from the group consisting of H and lower alkyl; and L is —CH$_2$—CH$_2$—, —CH$_2$—O—, —CH$_2$—NH—, or —CH═CH—, or pharmaceutically acceptable salts or esters thereof.

One certain embodiment of the invention is a compound selected from the group consisting of 2-(5-Methyl-3-phenyl-isoxazol-4-ylmethoxy)-thiazole-5-carboxylic acid ethyl ester, 2-[(E)-2-(3-Butyl-5-methyl-isoxazol-4-yl)-vinyl]-4-methyl-thiazole-5-carboxylic acid, 2-[2-(5-Methyl-3-pyridin-2-yl-isoxazol-4-yl)-ethyl]-thiazole-5-carboxylic acid methyl ester, 2-{2-[3-(5-Fluoro-pyridin-2-yl)-5-methyl-isoxazol-4-yl]-ethyl}-4-methyl-thiazole-5-carboxylic acid methyl ester, and 4-Methyl-2-[2-(5-methyl-3-pyridin-2-yl-isoxazol-4-yl)-ethyl]-thiazole-5-carboxylic acid methyl ester.

One certain embodiment of the invention is a process for preparing a compound of formula I, which process comprises reacting a compound of formula $R^4R^5NH$ (III) with a compound of formula II, wherein $R^1, R^2, R^3, R^4, R^5, R^6, R^7, R^8$ are as defined herein and L is CH$_2$—CH$_2$—, —CH$_2$—O— or —CH═CH—, under standard reaction conditions such as TBTU and Hüning's Base in DMF.

One certain embodiment of the invention is a compound as described herein, whenever prepared by a process as defined above.

One certain embodiment of the invention is a compound as described herein for the use as a therapeutically active substance.

One certain embodiment of the invention is a compound as described herein for the use as therapeutically active substance.

One certain embodiment of the invention is a compound as described herein for the use for the therapeutic and/or prophylactic treatment of a disorder or condition mediated by the GABA A α5 receptor, or that can be treated via modulation of the GABA A α5 receptor.

One certain embodiment of the invention is a compound as described herein for the use as therapeutically active substance for the therapeutic and/or prophylactic treatment of diseases and disorders related to the GABA A α5 receptor.

One certain embodiment of the invention is a compound as described herein for the use for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

One certain embodiment of the invention is a therapeutically active substance, comprising a compound as described herein.

One certain embodiment of the invention is a pharmaceutical composition comprising a compound as described herein as an active ingredient and a pharmaceutically acceptable carrier and/or a pharmaceutically acceptable auxiliary substance.

One certain embodiment of the invention is a pharmaceutical composition, comprising a compound as described herein for the therapeutic and/or prophylactic treatment of a disorder or condition mediated by the GABA A α5 receptor, or that can be treated via modulation of the GABA A α5 receptor.

One certain embodiment of the invention is a pharmaceutical composition, comprising a compound as described herein for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

One certain embodiment of the invention is the use of a compound as described herein for the manufacture of a medicament for the therapeutic and/or prophylactic treatment of a disorder or condition mediated by the GABA A α5 receptor, or that can be treated via modulation of the GABA A α5 receptor.

One certain embodiment of the invention is the use of a compound as described herein for the manufacture of a medicament for the therapeutic and/or prophylactic treatment of diseases and disorders which are related to the GABA A α5 receptor.

One certain embodiment of the invention is the use of a compound as described herein for the manufacture of a medicament for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

One certain embodiment of the invention is the use of a compound as described herein for the manufacture of a medicament for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for the preparation of cognitive enhancers.

One certain embodiment of the invention is the use of a compound as described herein for the therapeutic and/or prophylactic treatment of a disorder or condition mediated by the GABA A α5 receptor, or that can be treated via modulation of the GABA A α5 receptor.

One certain embodiment of the invention is the use of a compound as described herein for the therapeutic and/or prophylactic treatment of diseases and disorders which are related to the GABA A α5 receptor.

One certain embodiment of the invention is the use of a compound as described herein for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

One certain embodiment of the invention is the use of a compound as described herein for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers.

One certain embodiment of the invention is a method for the therapeutic and/or prophylactic treatment of a disorder or condition mediated by the GABA A α5 receptor, or that can be treated via modulation of the GABA A α5 receptor, particularly for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers, which method comprises administering a compound as described herein to a human being or animal.

One certain embodiment of the invention is a method for the therapeutic and/or prophylactic treatment of a disorder or condition mediated by the GABA A α5 receptor binding site, or that can be treated via modulation of the GABA A α5 receptor binding site, particularly for the therapeutic and/or prophylactic treatment of acute neurological disorders, chronic neurological disorders, cognitive disorders, Alzheimer's disease, memory deficits, schizophrenia, positive, negative and/or cognitive symptoms associated with schizophrenia, bipolar disorders, autism, Down syndrome, neurofibromatosis type I, sleep disorders, disorders of circadian rhythms, amyotrophic lateral sclerosis (ALS), dementia caused by AIDS, psychotic disorders, substance-induced psychotic disorder, anxiety disorders, generalized anxiety disorder, panic disorder, delusional disorder, obsessive/compulsive disorders, acute stress disorder, drug addictions, movement disorders, Parkinson's disease, restless leg syndrome, cognition deficiency disorders, multi-infarct dementia, mood disorders, depression, neuropsychiatric conditions, psychosis, attention-deficit/hyperactivity disorder, neuropathic pain, stroke and attentional disorders or for use as cognitive enhancers, which method comprises administering a compound as described herein to a human being or animal.

One certain embodiment of the invention is a method for the therapeutic and/or prophylactic treatment of diseases and disorders which are related to the GABA A α5 receptor The preferred indications using the compounds of the present invention are cognitive disorders, schizophrenia, positive, negative and/or cognitive symptoms associated with schizophrenia and Alzheimer's disease. Most preferred indications are schizophrenia and Alzheimer's disease. Particularly preferred indication is Alzheimer's disease.

The compounds of formula I can be prepared in accordance with the following schemes. The starting material is commercially available or can be prepared in accordance with known methods. Any previously defined residues and variables will continue to have the previously defined meaning unless otherwise indicated.

Reaction Schemes

The compounds of formula I can be prepared in accordance with the following schemes. The starting material is commercially available or can be prepared in accordance with known methods. Any previously defined residues and variables will continue to have the previously defined meaning unless otherwise indicated.

The present compounds of formula I and their pharmaceutically acceptable salts can be prepared by a process comprising the steps of:

A) Reacting a compound of formula 1 with hydroxylamine hydrochloride in a suitable solvent, such as ethanol and water in the presence of a base, such as aqueous sodium hydroxide to give a compound of formula 2, followed by reacting the compound of formula 2 with a chlorinating agent such as N-chlorosuccinimide in a suitable solvent, such as DMF to give a compound of formula 3.

Scheme 1: Synthesis of intermediates 3

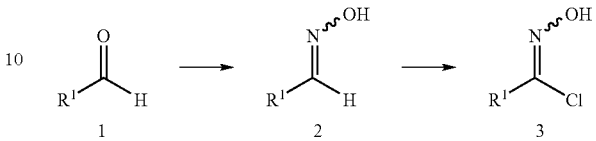

B) A compound of formula 3 is then reacted further to a compound of formula 6 by reacting
   i) with a compound of formula 4 in the presence of a suitable base, such as triethylamine, in a suitable solvent, such as chloroform, or
   ii) with a compound of formula 5 in the presence of a suitable base, such as triethylamine, in a suitable solvent, such as diethylether.

Scheme 2: Synthesis of intermediates 6

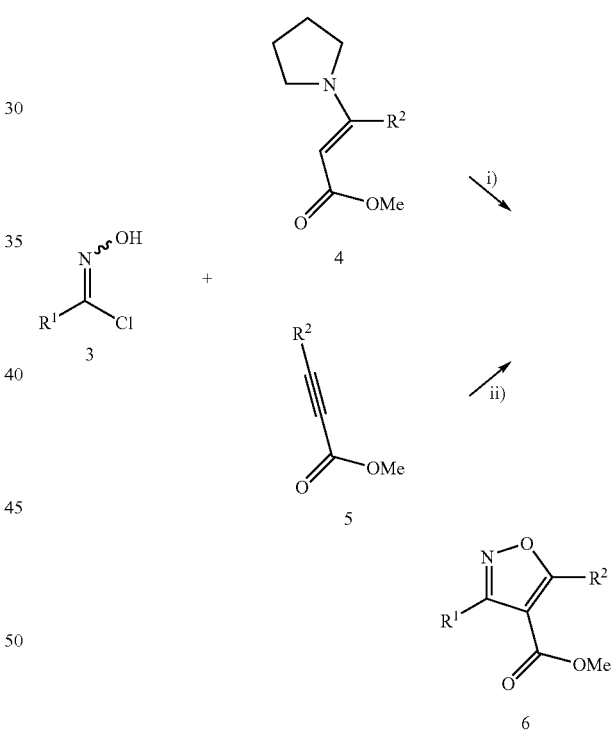

C) A compound of formula 6 is then reacted to a compound of formula 8 with
   i) a reducing agent, such as lithium aluminium hydride, in a suitable solvent, such as THF to give a compound of formula 8, or
   ii-1) a hydrolytic agent such as NaOH or LiOH in a suitable solvent such as THF, MeOH or EtOH, water to give a compound of formula 7,
   ii-2) followed by reacting a compound of formula 7 with a reducing agent, such as lithium aluminium hydride or ethylchloroformate in the presence of sodiumborohydride in a suitable solvent such as THF or water.

Scheme 3: Synthesis of intermediates 8

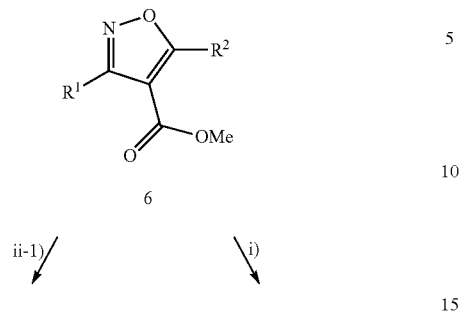

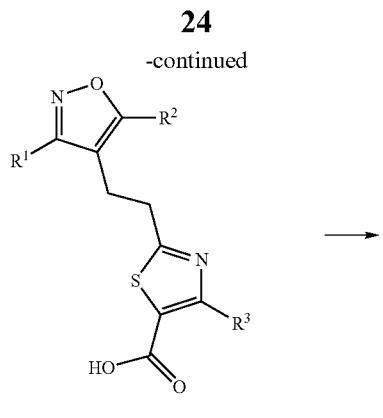

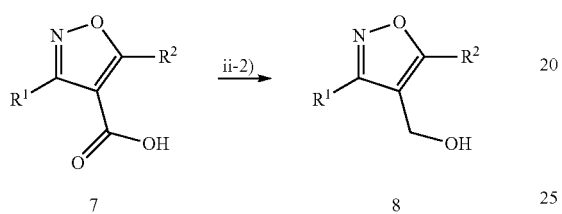

D) A compound of formula 8 is then treated with a chlorinating agent such as thionylchloride in a suitable solvent such as DCM to give a compound of formula 9.

Scheme 4: Synthesis of intermediates 9

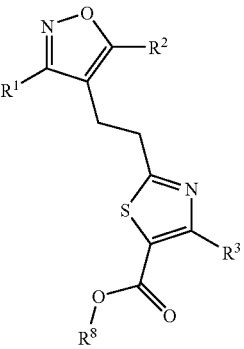

E) A compound of formula 9 is further reacted with a compound of formula 10 in the presence of a suitable base such as LDA or BuLi at reduced temperatures in the presence of a suitable solvent such as THF to give a compound of formula 11 or a compound of formula 12 upon further reaction of compound 11 with trimethylsilyldiazomethane in a suitable solvent such as diethyl ether and methanol. Compounds of formula 12 can be converted to compounds of formula 11 upon treatment with a suitable base such as sodium hydroxide or lithium hydroxide in a suitable solvent, such as dioxane, water, THF or methanol.

Scheme 5: Synthesis of intermediates 11 and 12

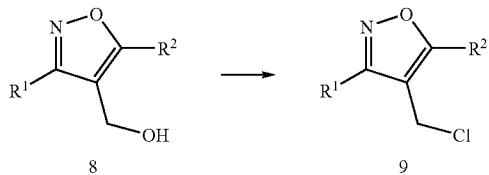

F) A compound of formula 8 can treated with an oxidizing agent such as manganese(IV) oxide or DMP in a suitable solvent such as DCM.

Scheme 6: Synthesis of intermediates 13

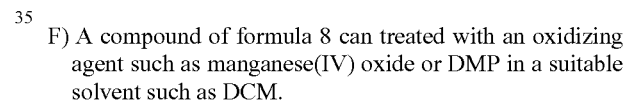

G) A compound of formula 13 can be reacted with a compound of formula 14 in the presence of acetic anhydride in a solvent such as acetic acid at elevated temperatures such as 150° C. for prolonged times to give a compound of formula 15.

Scheme 7: Synthesis of intermediates 15

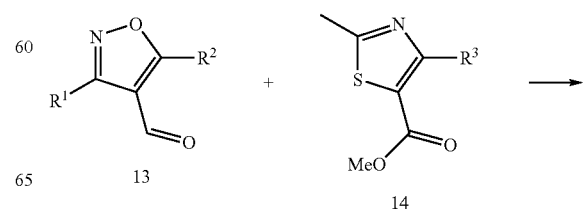

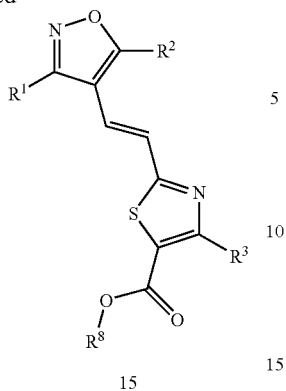

H) A compound of formula 13 can be reacted with a compound of formula 10 in the presence of a base such as LDA or BuLi in a suitable solvent such as THF at reduced temperatures which upon further reaction with trimethylsilyldiazomethane in a suitable solvent such as diethyl ether and methanol gives a compound of formula 16. Further treatment of compound 16 with an acid, such as sulfuric acid at elevated temperatures such as 90° C. to give a compound of formula 15.

I) A compound of formula 17 can be reacted with an amine ($R^4R^5NH$) in the presence of trimethylaluminium in a suitable solvent such as dioxane at elevated temperature to give a compound of formula 18.

Scheme 9: Synthesis of intermediates 18

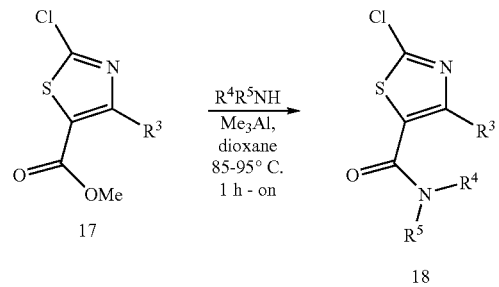

J) A compound of formula 8 can then be treated with a suitable base such as NaH in a suitable solvent such as THF and then reacted with a compound of formula 18 to give a compound of formula 19 (also formula I).

Scheme 8: Synthesis of intermediates 15 and 16

Scheme 10: Synthesis of intermediates 19

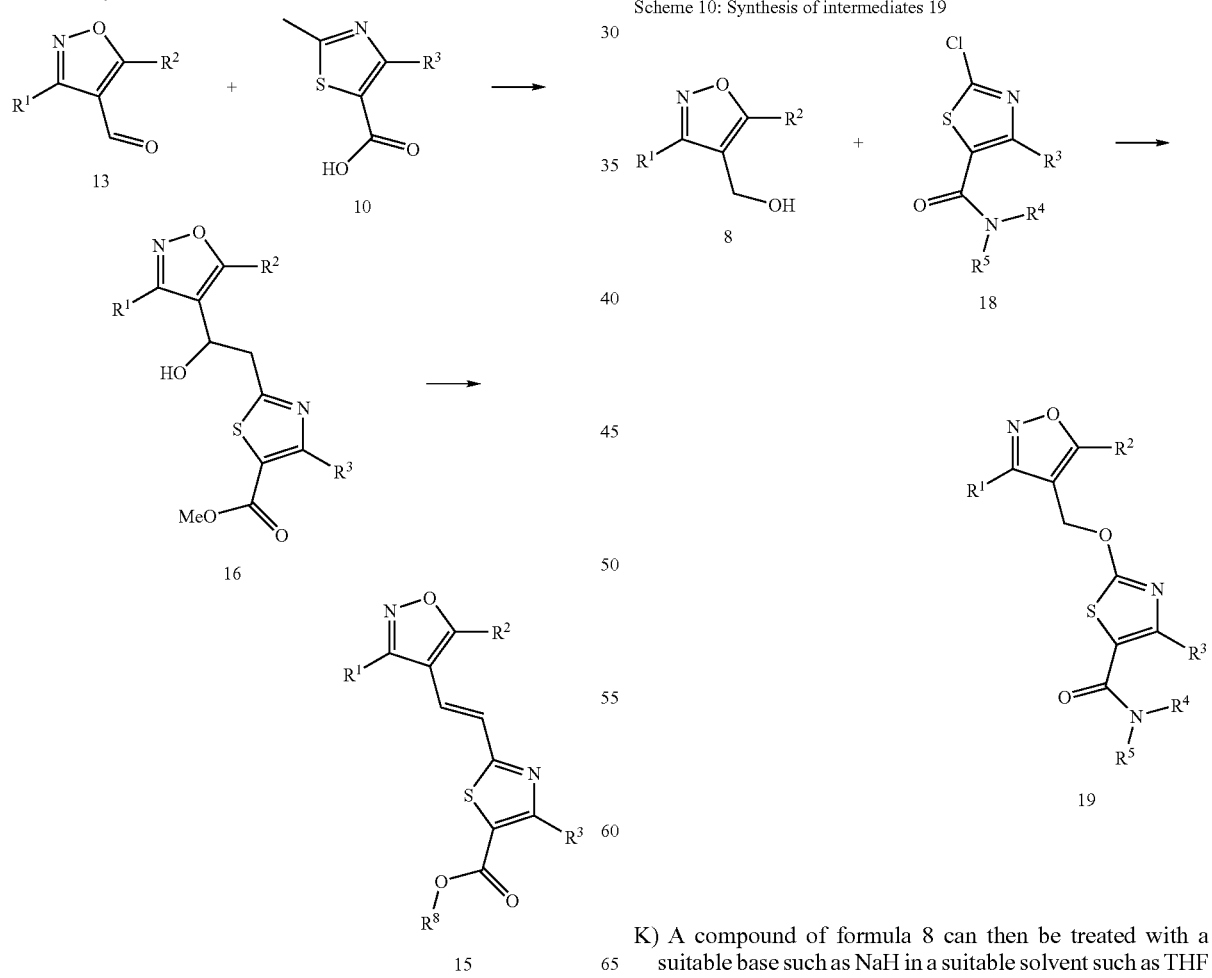

K) A compound of formula 8 can then be treated with a suitable base such as NaH in a suitable solvent such as THF and then reacted with a compound of formula 17 to give a compound of formula 20.

Scheme 11: Synthesis of intermediates 20

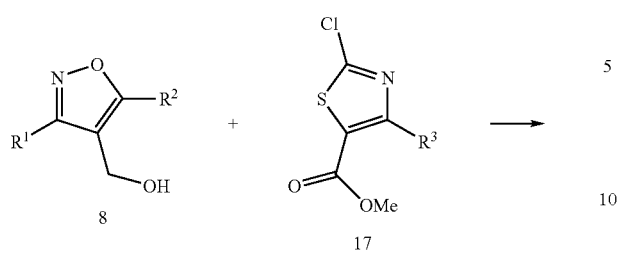

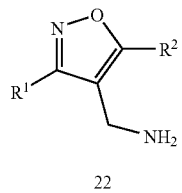

L) A compound of formula 8 can be reacted with phthalimide in the presence of triphenylphosphine and diethylazodicarboxylate, in a suitable solvent, such as THF to give a compound of formula 21 then reacting the compound of formula 18 with hydrazine, to give a compound of formula 22.

Scheme 12: Synthesis of intermediates 21 and 22

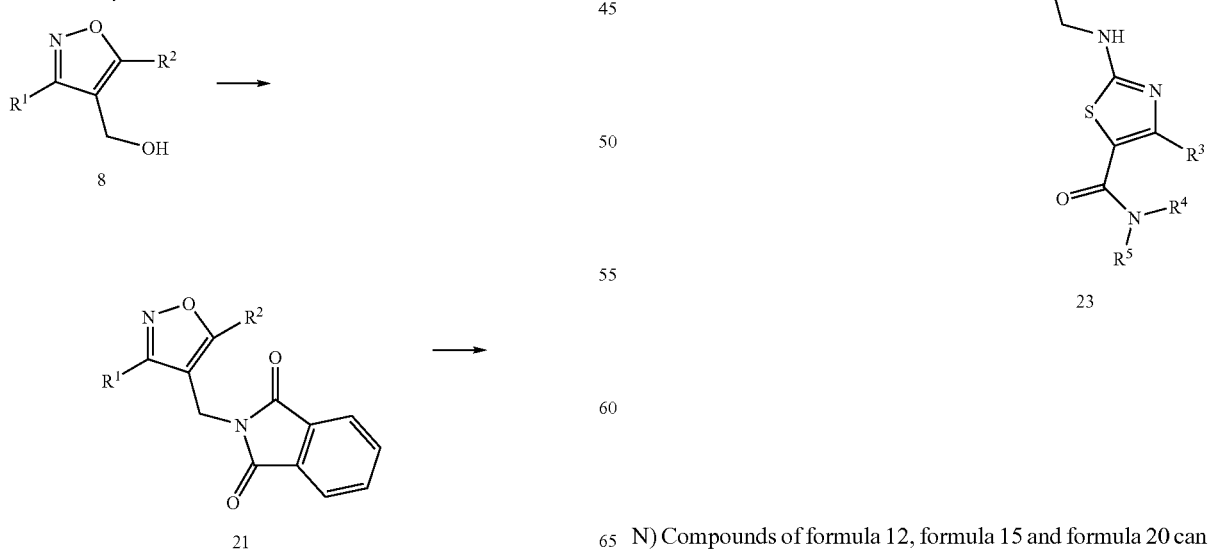

M) A compound of formula 22 can be reacted with a compound of formula 18 at elevated temperatures such as 100° C. for prolonged times, (or at 150° C. with microwave irradiation for 1 h) in a suitable solvent such as DMF to give a compound of formula 23 (also formula I).

N) Compounds of formula 12, formula 15 and formula 20 can further react according to standard methods to give compounds of formula I.

Scheme 13: Synthesis of compounds of formula I, with L = CH$_2$—CH$_2$—, —CH$_2$—O— or —CH=CH—

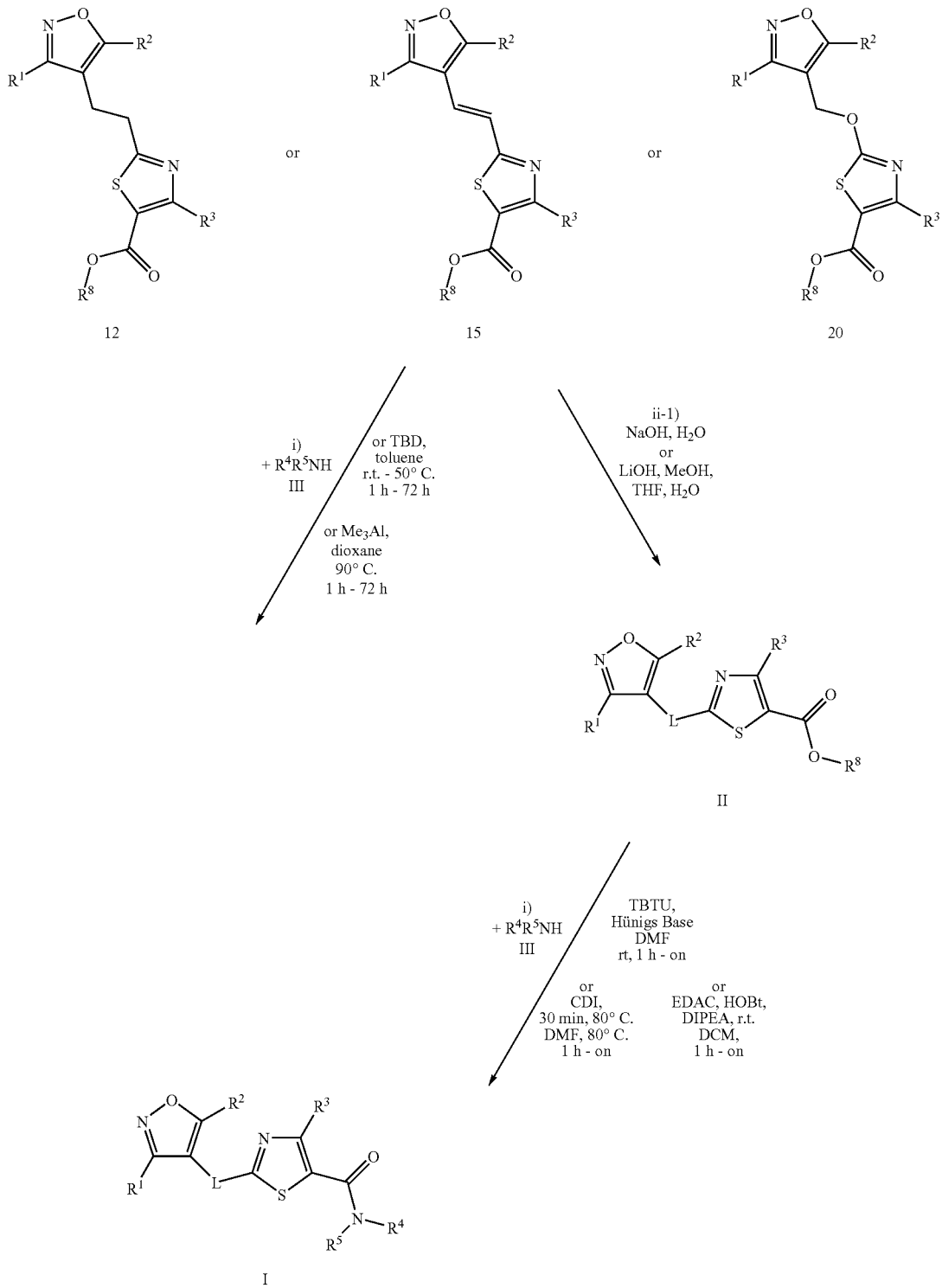

The corresponding salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. M(OH)$_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilization.

The corresponding pharmaceutically acceptable salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilization.

The conversion into pharmaceutically acceptable esters of compounds of formula I bearing a carboxy group can be carried out e.g. by treatment of a suitable carboxy group with a suitable alcohol using e.g. a condensating reagent such as benzotriazol-1-yloxytris(dimethylamino)-phosphonium hexafluorophosphate (BOP), N,N-dicylohexyl-carbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluoro-borate (TPTU), or by direct reaction with a suitable alcohol under acidic conditions, as for example in the presence of a strong mineral acid like hydrochloric acid, sulfuric acid and the like. The conversion into pharmaceutically acceptable esters of compounds of formula I bearing a hydroxy group can be carried out with suitable acids by analogous methods.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of general formula I in this invention can be derivatized at functional groups to provide derivatives which are capable of conversion back to the parent compound in vivo.

Pharmacological Tests

The compounds of formula I and their pharmaceutically acceptable salts and esters possess valuable pharmacological properties. The compounds of the present invention are ligands for GABA A receptors containing the α5 subunit and are therefore useful in the therapy where cognition enhancement is required.

The compounds were investigated in accordance with the test given hereinafter:

Membrane Preparation and Binding Assay

The affinity of compounds at GABA A receptor subtypes was measured by competition for [3H]flumazenil (85 Ci/mmol; Roche) binding to HEK293 cells expressing rat (stably transfected) or human (transiently transfected) receptors of compositional α1β3γ2, α2β3γ2, α3β3γ2 and α5β3γ2.

Cell pellets were suspended in Krebs-tris buffer (4.8 mM KCl, 1.2 mM $CaCl_2$, 1.2 mM $MgCl_2$, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were re-suspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 mL (96-well plates) which contained 100 mL of cell membranes, [3H]flumazenil at a concentration of 1 nM for α1, α2 and α3 subunits and 0.5 nM for α5 subunits and the test compound in the range of $10\text{-}10^{-3} \times 10^{-6}$ M. Nonspecific binding was defined by $10^{-5}$ M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and the preferred compounds were found to possess a Ki value for displacement of [3H]flumazenil from α5 subunits of the rat GABA A receptor of 100 nM or less. Most preferred is a compound with a Ki (nM)<35. In a preferred embodiment the compounds of the invention are binding selective for the α5 subunit relative to the α1, α2 and α3 subunit.

Representative test results are listed below.

TABLE 2

| human Ki (hKi) values | |
|---|---|
| Ex. | hKi GABA A α5 (nM) |
| 1 | 5.7 |
| 2 | 10.9 |
| 3 | 7.9 |
| 4 | 37.8 |
| 5 | 8.2 |
| 6 | 33.7 |
| 7 | 13.8 |
| 8 | 20.3 |
| 9 | 5.7 |
| 10 | 4.3 |
| 11 | 7.7 |
| 12 | 13.4 |
| 13 | 4.2 |
| 14 | 14.1 |
| 15 | 12 |
| 16 | 21.3 |
| 17 | 42.8 |
| 18 | 32.3 |
| 19 | 87.6 |
| 20 | 90.5 |
| 21 | 40.2 |
| 22 | 18.1 |
| 23 | 26.1 |
| 24 | 18.8 |
| 25 | 33.6 |
| 26 | 34.7 |
| 27 | 14 |
| 28 | 17.8 |
| 29 | 32.4 |
| 30 | 23.6 |
| 31 | 5.2 |
| 32 | 7 |
| 33 | 9 |
| 34 | 16 |
| 35 | 6.6 |
| 36 | 14 |
| 37 | 55.9 |
| 38 | 10.8 |
| 39 | 25.3 |
| 40 | 13.3 |
| 41 | 10.8 |

TABLE 2-continued human Ki (hKi) values

| Ex. | hKi GABA A α5 (nM) |
|---|---|
| 42 | 12.7 |
| 43 | 18.6 |
| 44 | 15.7 |
| 45 | 26.3 |
| 46 | 18.1 |
| 47 | 26.3 |
| 48 | 23.1 |
| 49 | 43.3 |
| 50 | 16.8 |
| 51 | 11.1 |
| 52 | 15.2 |
| 53 | 18.7 |
| 54 | 15.9 |
| 55 | 35.6 |
| 56 | 16.9 |
| 57 | 39.2 |
| 58 | 50.9 |
| 59 | 32.5 |
| 60 | 35.5 |
| 61 | 43.6 |
| 62 | 45 |
| 63 | 1.2 |
| 64 | 1.7 |
| 65 | 1.3 |
| 66 | 1.8 |
| 67 | 2.8 |
| 68 | 0.4 |
| 69 | 0.3 |
| 70 | 0.5 |
| 71 | 1.5 |
| 72 | 0.6 |
| 73 | 1.6 |
| 74 | 8.4 |
| 75 | 1.8 |
| 76 | 4.1 |
| 77 | 3.5 |
| 78 | 2.9 |
| 79 | 4.1 |
| 80 | 17.4 |
| 81 | 5.5 |
| 82 | 4.7 |
| 83 | 27.4 |
| 84 | 4.1 |
| 85 | 5.1 |
| 86 | 31.2 |
| 87 | 4 |
| 88 | 6.2 |
| 89 | 22.8 |
| 90 | 24.8 |
| 91 | 35.3 |
| 92 | 40.4 |
| 93 | 1.9 |
| 94 | 1.2 |
| 95 | 2.2 |
| 96 | 1.5 |
| 97 | 4.7 |
| 98 | 1.9 |
| 99 | 27.6 |
| 100 | 2 |
| 101 | 28.8 |
| 102 | 4.4 |
| 103 | 1.8 |
| 104 | 3.1 |
| 105 | 7.9 |
| 106 | 2.1 |
| 107 | 2.6 |
| 108 | 24.5 |
| 109 | 33.2 |
| 110 | 30.8 |
| 111 | 5.5 |
| 112 | 1.3 |
| 113 | 5.1 |
| 114 | 6.4 |
| 115 | 4.7 |
| 116 | 4.4 |
| 117 | 21 |
| 118 | 2.5 |
| 119 | 2.4 |
| 120 | 57.8 |
| 121 | 5 |
| 122 | 5.7 |
| 123 | 1.1 |
| 124 | 5.5 |
| 125 | 6.6 |
| 126 | 16.8 |
| 127 | 2.2 |
| 128 | 1.8 |
| 129 | 4.2 |
| 130 | 5.4 |
| 131 | 12.7 |
| 132 | 10.2 |
| 133 | 19.2 |
| 134 | 21.5 |
| 135 | 9 |
| 136 | 27.5 |

Pharmaceutical Compositions

The compounds of formula I or II as well as their pharmaceutically acceptable salts and esters can be used as therapeutically active substances, e.g. in the form of pharmaceutical compositions. The pharmaceutical compositions of the invention can be formulated for any route of administration, such as oral, sub-lingual, buccal, parenteral (subcutaneous, intramuscular, intravenous), rectal, topical, intranasal and trough inhalation or insufflation, and comprise at least one compound of formula I or pharmaceutically acceptable salts or esters thereof, with any pharmaceutically suitable ingredient, excipient, carrier, adjuvant or vehicle. Oral pharmaceutical compositions are e.g. tablets, coated tablets, dragées, hard gelatin capsules, soft gelatin capsules, solutions, emulsions or suspensions. Rectal pharmaceutical compositions are e.g. in the form of suppositories.

The invention provides pharmaceutical compositions containing compounds of formula I or II and their pharmaceutically acceptable salts and esters and a pharmaceutically acceptable carrier. Suitable pharmaceutically acceptable carriers are pharmaceutically inert, inorganic or organic excipients that can be used the production of tablets, coated tablets, dragées and hard gelatin capsules. Examples are lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semisolid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

The pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt or ester thereof. The daily dosage can be administered as single dose or in divided doses and, in addition, the upper limit can also be exceeded when necessary.

Examples of compositions according to the invention are, but are not limited to:

EXAMPLE A

Tablets of the following composition are manufactured in the usual manner:

TABLE 3

| possible tablet composition | |
|---|---|
| ingredient | mg/tablet |
| Compound of formula I or II | 5 |
| Lactose | 45 |
| Corn starch | 15 |
| Microcrystalline cellulose | 34 |
| Magnesium stearate | 1 |
| Tablet weight | 100 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

EXAMPLE B

Capsules of the following composition are manufactured:

TABLE 4

| possible capsule composition | |
|---|---|
| ingredient | mg/capsule |
| Compound of formula I or II | 10 |
| Lactose | 155 |
| Corn starch | 30 |
| Talc | 5 |
| Capsule fill weight | 200 |

Manufacturing Procedure
1. Mix items 1, 2 and 3 in a suitable mixer for 30 minutes.
2. Add item 4 and mix for 3 minutes.
3. Fill into a suitable capsule.

Items 1, 2 and 3 are firstly mixed in a mixer and then in a comminuting machine. The mixture is returned to the mixer, item 4 is added thereto and mixed thoroughly. The mixture is filled by machine into hard gelatin capsules.

EXAMPLE C

Suppositories of the following composition are manufactured:

TABLE 5

| possible suppository composition | |
|---|---|
| ingredient | mg/supp. |
| Compound of formula I or II | 15 |
| Suppository mass | 1285 |
| Total | 1300 |

Manufacturing Procedure
Item 2 is melted in a glass or steel vessel, mixed thoroughly and cooled to 45° C. Thereupon, the finely powdered item 1 is added thereto and stirred until it has dispersed completely. The mixture is poured into suppository moulds of suitable size, left to cool, the suppositories are then removed from the moulds and packed individually in wax paper or metal foil.

EXPERIMENTAL PART

The following examples 1-136 are provided for illustration of the invention. They should not be considered as limiting the scope of the invention, but merely as being representative thereof.

Example 1

4-Methyl-2-[2-(5-methyl-3-phenyl-isoxazol-4-yl)-ethyl]-thiazole-5-carboxylic acid iso-propylamide

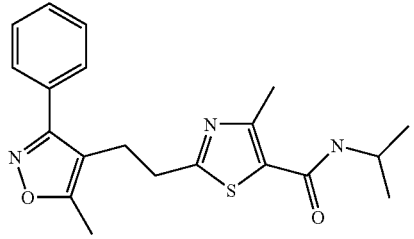

a) 2-[2-(5-Methyl-3-phenyl-isoxazol-4-yl)-ethyl]-thiazole-5-carboxylic acid

To a stirred solution of 2,4-dimethyl-thiazole-5-carboxylic acid (250 mg, 1.59 mmol) in THF (16 mL) at −78° C. and under argon was added LDA (1.6 mL of a 2M solution in THF, 3.2 mmol) dropwise. After 1.5 h a solution of 4-chloromethyl-5-methyl-3-phenyl-isoxazole (330 mg, 1.59 mmol) in THF (4 mL) was added dropwise. After 1 h the reaction mixture was quenched with HCl (1N, 10 mL) then warmed to room temperature and extracted with ethyl acetate. The combined extracts were dried, filtered and concentrated. Purification by chromatography (silica, 0 to 10% methanol in dichloromethane) gave the title compound (315 mg, 60%) as a light yellow gum. MS: m/e=329.1 [M+H]$^+$.

b) 4-Methyl-2-[2-(5-methyl-3-phenyl-isoxazol-4-yl)-ethyl]-thiazole-5-carboxylic acid iso-propylamide To a stirred solution of isopropylamine (216 mg, 3.65 mmol) in dioxane (4 mL) under argon and at room temperature was added trimethylaluminium (1.83 mL of a 2M solution in toluene, 3.7 mmol). After 1 h, a solution of 4-methyl-2-[2-(5-methyl-3-phenyl-isoxazol-4-yl)-ethyl]-thiazole-5-carboxylic acid (300 mg, 0.91 mmol) in dioxane (4 mL) was added and the reaction mixture warmed to 90° C. After 4 h, the reaction mixture was cooled, quenched with ice water and extracted with dichloromethane. The combined extracts were washed with Seignette's salt solution then dried, filtered, and concentrated. Purification by chromatography (silica, 0 to 10% methanol in dichloromethane) gave the title compound (182 mg, 54%) as a light yellow gum. MS: m/e=370.1 [M+H]$^+$.

Example 2

(S)-4-Methyl-2-[2-(5-methyl-3-phenyl-isoxazol-4-yl)-ethyl]-thiazole-5-carboxylic acid (tetrahydro-furan-3-yl)-amide

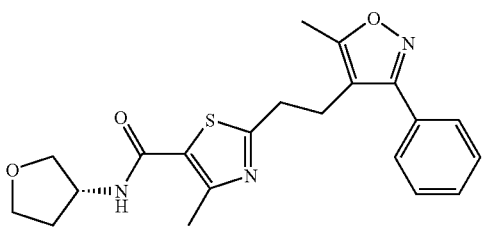

To a stirred suspension of (S)-tetrahydrofuran-3-amine HCl (127 mg, 1.0 mmol) in toluene (2 mL) under argon at room temperature was added trimethylaluminium (1 mL of a 2M solution in toluene, 2.0 mmol). After 2 h, a solution of 4-methyl-2-[2-(5-methyl-3-phenyl-isoxazol-4-yl)-ethyl]-thiazole-5-carboxylic acid (130 mg, 0.39 mmol) in toluene (4 mL) was added and the reaction mixture warmed to 90° C. After 2 h, the reaction mixture was cooled, quenched with ice water and extracted with dichloromethane. The combined extracts were washed with Seignette's salt solution then dried, filtered, and concentrated. Purification by chromatography (silica, 0 to 10% methanol in dichloromethane) gave the title compound (71 mg, 45%) as a colourless oil. MS: m/e=398.1 [M+H]$^+$.

Example 3

Rac-4-Methyl-2-[2-(5-methyl-3-phenyl-isoxazol-4-yl)-ethyl]-thiazole-5-carboxylic acid (2-hydroxy-1-methyl-ethyl)-amide

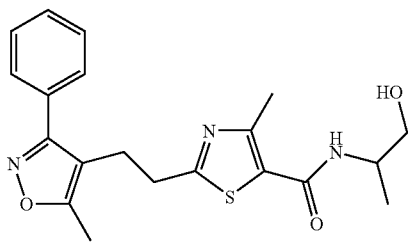

To a solution of 4-methyl-2-[2-(5-methyl-3-phenyl-isoxazol-4-yl)-ethyl]-thiazole-5-carboxylic acid (100 mg, 0.31 mmol) in DMF (3 mL) were added 2-(1H-benzotriazole-1-yl)-1,1,3,3-tetramethyluronium tetrafluoroborate (108 mg, 0.33 mmol), N,N-diisopropyl ethyl amine (197 μL, 1.67 mmol) and rac-2-amino-1-propanol (30 mg, 0.40 mmol). The resulting reaction mixture was stirred for 2 h. The reaction mixture was extracted with ethyl acetate. The combined organic layers were then dried over sodium sulfate, filtered and evaporated. Concentration and purification by chromatography (silica, 0 to 2.5% methanol in dichlormethane) afforded the title compound (59 mg, 50%) as a colourless oil. MS: m/e=386.2 [M+H]$^+$.

Example 4

4-Methyl-2-[2-(5-methyl-3-phenyl-isoxazol-4-yl)-ethyl]-thiazole-5-carboxylic acid (2-hydroxy-2-methyl-propyl)-amide

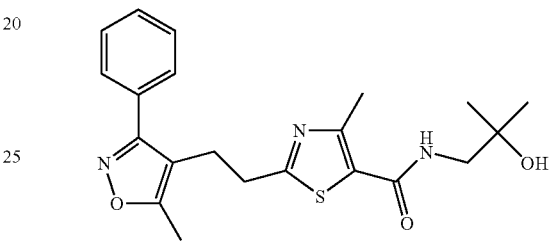

As described for example 3,4-methyl-2-[2-(5-methyl-3-phenyl-isoxazol-4-yl)-ethyl]-thiazole-5-carboxylic acid (100 mg, 0.31 mmol) was converted, using 1-amino-2-methyl-propan-2-ol instead of rac-2-amino-1-propanol, to the title compound (44 mg, 36%) which was obtained as a colourless oil after purification by chromatography (silica, 0 to 1.5% methanol in dichloromethane). MS: m/e=400.3 [M+H]$^+$.

Example 5

4-Methyl-2-[2-(5-methyl-3-phenyl-isoxazol-4-yl)-ethyl]-thiazole-5-carboxylic acid (tetrahydro-pyran-4-yl)-amide

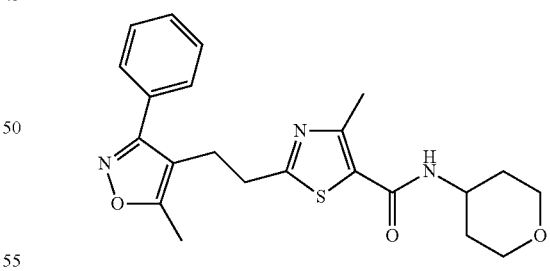

To a stirred suspension of 4-aminotetrahydropyran (123 mg, 1.2 mmol) in dioxane (5 mL) under argon at room temperature was added trimethylaluminium (0.6 mL of a 2M solution in toluene, 1.2 mmol). After 1 h, a solution of 4-methyl-2-[2-(5-methyl-3-phenyl-isoxazol-4-yl)-ethyl]-thiazole-5-carboxylic acid (100 mg, 0.3 mmol) in dioxane (5 mL) was added and the reaction mixture warmed to 90° C. After 3 h, the reaction mixture was cooled, quenched with ice water and extracted with dichloromethane. The combined extracts were washed with Seignette's salt solution then dried, filtered, and concentrated. Purification by chromatography (silica, 0 to 10% methanol in dichloromethane) gave the title compound (40 mg, 32%) as a colourless oil. MS: m/e=412.4 [M+H]⁺.

Example 6

4-Methyl-2-[2-(5-methyl-3-phenyl-isoxazol-4-yl)-ethyl]thiazole-5-carboxylic acid amide

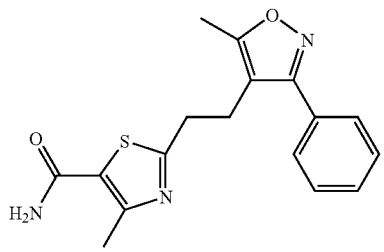

To a solution of 4-methyl-2-[2-(5-methyl-3-phenyl-isoxazol-4-yl)-ethyl]-thiazole-5-carboxylic acid (65 mg, 0.2 mmol) in DMF (82 mL) was added 1,1'-carbonyldiimidazole (39 mg, 0.24 mmol). The resulting reaction mixture was stirred for 1 h at 60° C. and then treated with an ammonium hydroxide solution (300 µL, 2.0 mmol) and stirred for 2 h at room temperature. The reaction mixture was then evaporated. Purification by chromatography (silica, dichloromethane:methanol=99:1 to 95:5) afforded the title compound (57 mg, 87%) as a white solid. MS: m/e=328.2 [M+H]⁺.

Example 7

2-[2-(5-Methyl-3-phenyl-isoxazol-4-yl)-ethyl]-thiazole-5-carboxylic acid isopropyl-amide

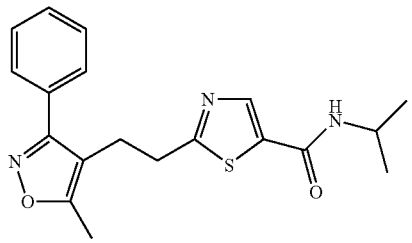

a) 2-Methyl-thiazole-5-carboxylic acid ethyl ester

To a stirred solution of ethyl 2-chloro-2-formyl acetate (5.0 g, 33 mmol) in benzene (50 mL) at reflux under argon was added thioamide (2.5 g, 33 mmol). After 4 h the reaction mixture was cooled, diluted with water (50 mL) and neutralized to pH 7 with a saturated solution of sodium hydrogencarbonate. The reaction mixture was extracted with ethyl acetate then the combined extracts were washed with water and brine, then dried, filtered and concentrated in vacuo. Purification by chromatography (silica, 0 to 50% ethyl acetate in heptane) gave the title compound (2.68 g, 47%) as a yellow liquid. MS: m/e=172.0 [M+H]⁺.

b) 2-Methyl-thiazole-5-carboxylic acid

To a stirred solution of 2-methyl-thiazole-5-carboxylic acid ethyl ester (1.3 g, 8.0 mmol) in dioxane (12 mL) at room temperature was added NaOH (2N, 12 mL). After 1 h the reaction mixture was neutralized with HCl (1N, 12 mL), then filtered and the collected solid dried in vacuo to give the title compound (758 mg, 70%) as an off white solid. MS: m/e=142.0 [M−H]⁻.

c) 2-[2-(5-Methyl-3-phenyl-isoxazol-4-yl)-ethyl]-thiazole-5-carboxylic acid To a stirred solution of 2-methyl-thiazole-5-carboxylic acid (100 mg, 0.7 mmol) in THF (5 mL) at −72° C. and under argon was added LDA (0.7 mL of a 2M solution in THF, 1.40 mmol) dropwise. After 1.5 h a solution of 4-chloromethyl-5-methyl-3-phenyl-isoxazole (145 mg, 0.7 mmol) in THF (5 mL) was added dropwise. After 1 h the reaction mixture was quenched with HCl (1N, 10 mL) then warmed to room temperature and extracted with ethyl acetate. The combined extracts were dried, filtered and concentrated then triturated with diisopropyl ether to give the title compound (135 mg, 61%) as a light brown solid which was used directly in the next reaction.

d) 2-[2-(5-Methyl-3-phenyl-isoxazol-4-yl)-ethyl]-thiazole-5-carboxylic acid isopropyl amide To a stirred solution of isopropylamine (75 mg, 1.27 mmol) in dioxane (5 mL) under argon and at room temperature was added trimethylaluminium (0.6 mL of a 2M solution in toluene, 1.2 ml). After 1 h, a solution of 2-[2-(5-methyl-3-phenyl-isoxazol-4-yl)-ethyl]-thiazole-5-carboxylic acid (100 mg, 0.32 mmol) in dioxane (5 mL) was added and the reaction mixture warmed to 90° C. After 3 h, the reaction mixture was cooled, quenched with ice water and extracted with dichloromethane. The combined extracts were washed with Seignette's salt solution then dried, filtered, and concentrated. Purification by chromatography (silica, 0 to 3% methanol in dichloromethane) gave the title compound (78 mg, 69%) as a pale yellow oil. MS: m/e=356.1 [M+H]⁺.

Example 8

4-Methyl-2-[2-(5-methyl-3-pyridin-2-yl-isoxazol-4-yl)-ethyl]-thiazole-5-carboxylic acid methyl ester

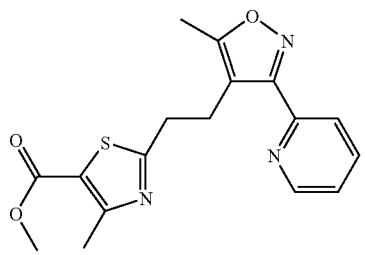

a) (E)- and/or (Z)-Pyridine-2-carbaldehyde oxime

To a suspension of 2-pyridinecarboxaldehyde (53.6 g, 500 mmol) and hydroxylamine hydrochloride (38.2 g, 544 mmol) in ethanol (36 mL) and water (69 mL) was added ice (205 g). Then an aqueous solution of sodium hydroxide (32%, 115 mL, 1.24 mol) was added dropwise within a 10 min period (temperature rises from −8° C. to +7° C.) whereupon most of the solid dissolves. After 1 h stirring at room temperature the resulting mixture was then acidified with HCl (5 N). The mixture was then extracted with dichloromethane to afford the title compound (47.7 g, 78%) which was obtained as an off white solid. MS: m/e=123.3 [M+H]$^+$.

b) 5-Methyl-3-pyridin-2-yl-isoxazole-4-carboxylic acid ethyl ester

To a suspension of N-chlorosuccinimide (6.0 g, 33 mmol) in chloroform (20 mL) was added pyridine (0.26 mL, 3.3 mmol) and a solution of (E)- and/or (Z)-pyridine-2-carbaldehyde oxime (4.0 g, 33 mmol) in chloroform (103 mL) during 15 min at ambient temperature. After stirring for 30 min at this temperature a solution of ethyl(E)-3-(1-pyrrolidino)-2-butenoate (6.0 g, 33 mmol) in chloroform (4 mL) was added. The resulting suspension was warmed to 50° C. and a solution of triethylamine (12 mL, 86 mmol) in chloroform (10 mL) was added dropwise over a period of 1 h. Stirring was continued for 0.5 h at 50° C. and for 30 h at room temperature. The dark brown solution was washed with water (100 mL) and the aqueous layers were extracted with dichloromethane (50 mL) and dried over sodium sulfate and evaporated. Purification by chromatography (silica, heptane:ethyl acetate 8:2 to 1:1) afforded the title compound (4.43 g, 58%) as a yellow oil. MS: m/e=233.3 [M+H]$^+$.

c) (5-Methyl-3-pyridin-2-yl-isoxazol-4-yl)-methanol

To a solution of 5-methyl-3-pyridin-2-yl-isoxazole-4-carboxylic acid ethyl ester (4.1 g, 18 mmol) in THF (229 mL) at 0° C. was added lithium aluminium hydride (367 mg, 10 mmol). And the resulting mixture stirred for 1 h at room temperature. Water (1.9 mL) was added carefully followed by aqueous sodium hydroxide (15%, 1.9 mL) and water (0.54 mL). The resulting suspension was stirred for 15 min at ambient temperature and filtered over Hyflo®. Concentration and trituration with heptane afforded the title compound (2.88 g, 86%) as a light yellow solid. MS: m/e=191.3 [M+H]$^+$.

d) 2-(4-Chloromethyl-5-methyl-isoxazol-3-yl)-pyridine

To a solution of (5-methyl-3-pyridin-2-yl-isoxazol-4-yl)-methanol (3.0 g, 16 mmol) in DCM (30 mL) at 0° C. was added thionyl chloride (3.75 g, 32 mmol) and the resulting mixture stirred for 1 h and then evaporated. After 1 h the reaction mixture was quenched with a solution of sodium hydrogen carbonate (1N, 15 mL) and extracted with ethyl acetate. The combined extracts were washed with water, dried over sodium sulfate, filtered and concentrated to give the title compound (3.2 g, 96%) as a light brown solid. MS: m/e=209.1 [M+H]$^+$.

e) 4-Methyl-2-[2-(5-methyl-3-pyridin-2-yl-isoxazol-4-yl)-ethyl]-thiazol-5-carboxylic acid methyl ester To a stirred solution of 2,4-dimethyl-thiazole-5-carboxylic acid (1.13 g, 7.0 mmol) in THF (61 mL) at −70° C. and under argon was added BuLi (1.6M in hexanes, 8.99 mL, 14.0 mmol) dropwise. After 2 h a solution of 2-(4-chloromethyl-5-methyl-isoxazol-3-yl)-pyridine (1.5 g, 7.0 mmol) in THF (26 mL) was added dropwise. After 3 h the reaction mixture was quenched with citric acid solution (5%, 10 mL) then warmed to room temperature and extracted with ethyl acetate. The combined extracts were dried, filtered and concentrated to give the intermediate acid compound (2.5 g) as a light brown solid. To a solution of intermediate acid (2.5 g) in MeOH (54 mL) and diethylether (30 mL) was added trimethylsilyldiazomethane (2M in diethylether, 21.6 mL, 4.3 mmol) in two portions under ice cooling. Then the reaction mixture was quenched by addition of acetic acid (conc., 0.7 mL), evaporated and extracted with ethyl acetate. The combined extracts were washed with NaOH (1N), water, dried over sodium sulfate, filtered and concentrated. Purification by chromatography (silica, heptane:ethyl acetate 8:2 to 1:1) afforded the title compound (1.69 g, 68%) as an orange solid. MS: m/e=344.1 [M+H]$^+$.

Example 9

4-Methyl-2-[2-(5-methyl-3-pyridin-2-yl-isoxazol-4-yl)-ethyl]-thiazole-5-carboxylic acid (tetrahydro-pyran-4-yl)-amide

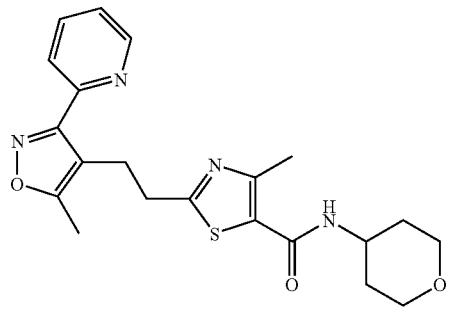

a) 4-Methyl-2-[2-(5-methyl-3-pyridin-2-yl-isoxazol-4-yl)-ethyl]-thiazole-5-carboxylic acid To a suspension of 4-methyl-2-[2-(5-methyl-3-pyridin-2-yl-isoxazol-4-yl)-ethyl]-thiazole-5-carboxylic acid methyl ester (1.62 g, 5.0 mmol) in THF (16 mL) was added a solution of lithium hydroxide monohydrate (396 mg, 9.0 mmol) in water (16 mL) followed by methanol (6 mL) and the resulting mixture stirred at room temperature for 4 h. The mixture was then evaporated to half volume and then acidified to pH 4 with HCl (1N) and cooled to 0° C. for 30 min. A solid precipitated and was filtered off and dried to afford the title compound (1.45 g, 93%) which was obtained as an off white solid. MS: m/e=328.3 [M−H]$^-$.

b) 4-Methyl-2-[2-(5-methyl-3-pyridin-2-yl-isoxazol-4-yl)-ethyl]-thiazole-5-carboxylic acid (tetrahydro-pyran-4-yl)-amide To a solution of 4-methyl-2-[2-(5-methyl-3-pyridin-2-yl-isoxazol-4-yl)-ethyl]-thiazole-5-carboxylic acid (80 mg, 0.24 mmol) in DMF (2 mL) were added 2-(1H-benzotriazole-1-yl)-1,1,3,3-tetramethyluronium tetrafluoroborate (86 mg, 0.27 mmol), N,N-diisopropyl ethyl amine (210 μL, 1.21 mmol) and 4-aminotetrahydropyran (27 mg, 0.27 mmol). The resulting reaction mixture was stirred overnight and then evaporated. Purification by chromatography (silica, heptane:ethyl acetate 8:2 to 1:1) afforded the title compound (97 mg, 97%) as a white solid. MS: m/e=413.2 [M+H]$^+$.

Example 10

4-Methyl-2-[2-(5-methyl-3-pyridin-2-yl-isoxazol-4-yl)-ethyl]-thiazole-5-carboxylic acid isopropylamide

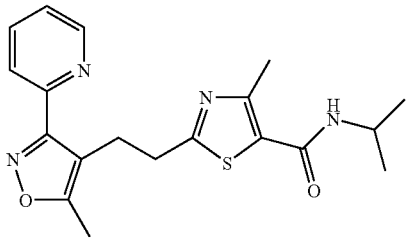

As described for example 9,4-methyl-2-[2-(5-methyl-3-pyridin-2-yl-isoxazol-4-yl)-ethyl]-thiazole-5-carboxylic acid (80 mg, 0.24 mmol) was converted, using isopropylamine instead of 4-aminotetrahydropyran, to the title compound (85 mg, 95%) which was obtained as an off white solid. MS: m/e=371.1 [M+H]$^+$.

Example 11

4-Methyl-2-[2-(5-methyl-3-pyridin-2-yl-isoxazol-4-yl)-ethyl]-thiazole-5-carboxylic acid cyclopropylamide

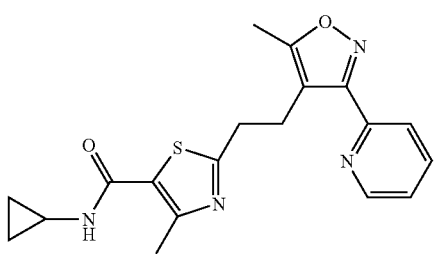

As described for example 9,4-methyl-2-[2-(5-methyl-3-pyridin-2-yl-isoxazol-4-yl)-ethyl]-thiazole-5-carboxylic acid (80 mg, 0.24 mmol) was converted, using cyclopropylamine instead of 4-aminotetrahydropyran, to the title compound (88 mg, 98%) which was obtained as an off white solid. MS: m/e=369.2 [M+H]$^+$.

Example 12

4-Methyl-2-[2-(5-methyl-3-pyridin-2-yl-isoxazol-4-yl)-ethyl]-thiazole-5-carboxylic acid cyclopropylmethyl-amide

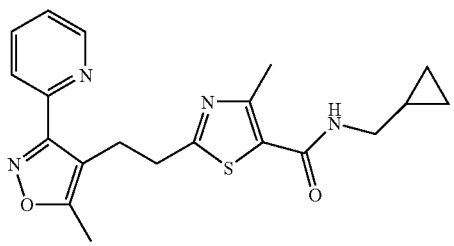

As described for example 9,4-methyl-2-[2-(5-methyl-3-pyridin-2-yl-isoxazol-4-yl)-ethyl]-thiazole-5-carboxylic acid (80 mg, 0.24 mmol) was converted, using aminomethylcyclopropane instead of 4-aminotetrahydropyran, to the title compound (81 mg, 87%) which was obtained as an off white solid. MS: m/e=383.2 [M+H]$^+$.

Example 13

4-Methyl-2-[2-(5-methyl-3-pyridin-2-yl-isoxazol-4-yl)-ethyl]-thiazole-5-carboxylic acid (2,2,2-trifluoro-ethyl)-amide

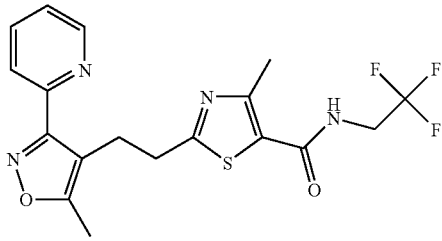

As described for example 9,4-methyl-2-[2-(5-methyl-3-pyridin-2-yl-isoxazol-4-yl)-ethyl]-thiazole-5-carboxylic acid (80 mg, 0.24 mmol) was converted, using 2,2,2-trifluoroethylamine instead of 4-aminotetrahydropyran, to the title compound (98 mg, 98%) which was obtained as an off white solid. MS: m/e=411.2 [M+H]$^+$.

Example 14

4-Methyl-2-[2-(5-methyl-3-pyridin-2-yl-isoxazol-4-yl)-ethyl]-thiazole-5-carboxylic acid (2-hydroxy-ethyl)-amide

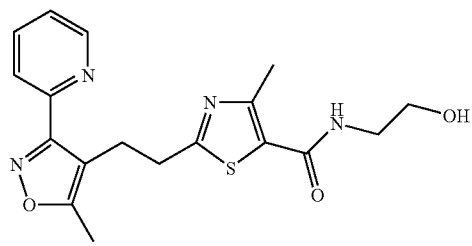

As described for example 9,4-methyl-2-[2-(5-methyl-3-pyridin-2-yl-isoxazol-4-yl)-ethyl]-thiazole-5-carboxylic acid (80 mg, 0.24 mmol) was converted, using ethanolamine instead of 4-aminotetrahydropyran, to the title compound (71 mg, 79%) which was obtained as an off white solid. MS: m/e=373.1 [M+H]$^+$.

Example 15

4-Methyl-2-[2-(5-methyl-3-pyridin-2-yl-isoxazol-4-yl)-ethyl]-thiazole-5-carboxylic acid ethylamide

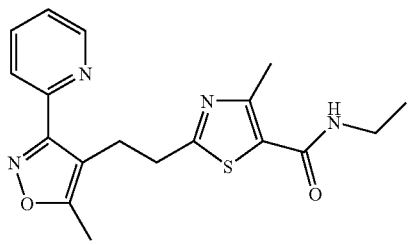

As described for example 9, 4-methyl-2-[2-(5-methyl-3-pyridin-2-yl-isoxazol-4-yl)-ethyl]-thiazole-5-carboxylic acid (80 mg, 0.24 mmol) was converted, using ethylamine (2M solution in THF) instead of 4-aminotetrahydropyran, to the title compound (85 mg, 98%) which was obtained as an off white solid. MS: m/e=357.1 [M+H]⁺.

Example 16

4-Methyl-2-[2-(5-methyl-3-pyridin-2-yl-isoxazol-4-yl)-ethyl]-thiazole-5-carboxylic acid methylamide

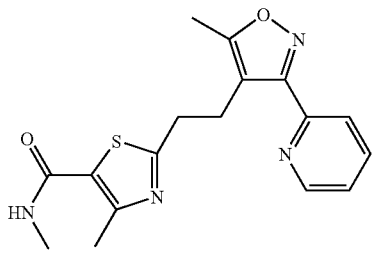

As described for example 9, 4-methyl-2-[2-(5-methyl-3-pyridin-2-yl-isoxazol-4-yl)-ethyl]-thiazole-5-carboxylic acid (80 mg, 0.24 mmol) was converted, using methylamine (2M solution in THF) instead of 4-aminotetrahydropyran, to the title compound (74 mg, 89%) which was obtained as a yellow gum. MS: m/e=343.1 [M+H]⁺.

Example 17

{4-Methyl-2-[2-(5-methyl-3-pyridin-2-yl-isoxazol-4-yl)-ethyl]-thiazol-5-yl}-thiomorpholin-4-yl-methanone

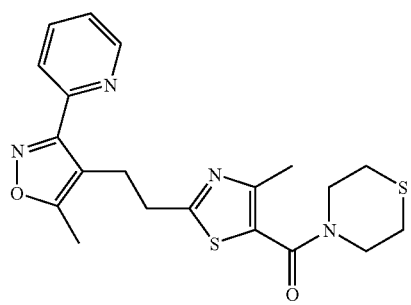

As described for example 9, 4-methyl-2-[2-(5-methyl-3-pyridin-2-yl-isoxazol-4-yl)-ethyl]-thiazole-5-carboxylic acid (80 mg, 0.24 mmol) was converted, using thiomorpholine instead of 4-aminotetrahydropyran, to the title compound (100 mg, 99%) which was obtained as a light yellow gum. MS: m/e=415.2 [M+H]⁺.

Example 18

4-Methyl-2-[2-(5-methyl-3-pyridin-2-yl-isoxazol-4-yl)-ethyl]-thiazole-5-carboxylic acid amide

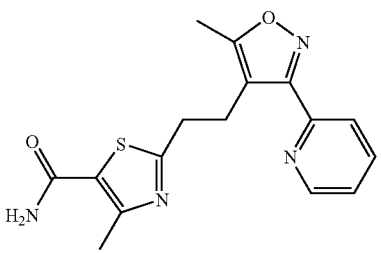

To a solution of 4-methyl-2-[2-(5-methyl-3-pyridin-2-yl-isoxazol-4-yl)-ethyl]-thiazole-5-carboxylic acid (100 mg, 0.3 mmol) in DMF (3 mL) was added 1,1'-carbonyldiimidazole (60 mg, 0.36 mmol). The resulting reaction mixture was stirred for 1 h at 60° C. and then treated with an ammonium hydroxide solution (455 µL, 3.0 mmol) and stirred for 2 h at room temperature. The reaction mixture was then evaporated. Purification by chromatography (silica, heptane:ethyl acetate 8:2 to 1:1) afforded the title compound (79 mg, 79%) as an off white solid. MS: m/e=329.1 [M+H]⁺.

Example 19

4-Methyl-2-[2-(3-pyridin-2-yl-isoxazol-4-yl)-ethyl]-thiazole-5-carboxylic acid (tetra-hydro-pyran-4-yl)-amide

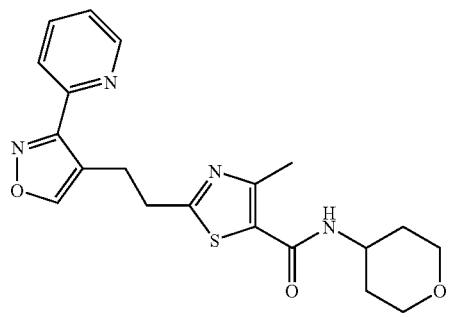

a) 3-Pyridin-2-yl-isoxazole-4-carboxylic acid ethyl ester

To a solution of N-chlorosuccinimide (54.7 g, 409 mmol) in DMF (1 L) was added pyridine-2-carbaldoxime (50 g, 409 mmol) portionwise and the resulting mixture was then stirred for 64 h at room temperature. To this solution was then added ethyl 3-(N,N-dimethylamino)acrylate (58.6 g, 409 mmol) and triethylamine (82.9 mL, 819 mmol) in chloroform (10 mL) and the resulting mixture was then stirred for 14 h at room temperature and poured onto a mixture of ice water and HCl (4 N, 100 mL) and extracted with ethylacetate. The organic extract was then washed with water, saturated aqueous sodium hydrogen carbonate solution, brine, dried with sodium sulfate, filtered and evaporated. Purification by distillation afforded the title product (58.9 g, 66%) which was obtained as a light brown liquid. Bp 125-127° C. at 0.4 mbar. MS: m/e=219.2 [M+H]⁺.

b) 3-Pyridin-2-yl-isoxazole-4-carboxylic acid

To a suspension of 3-pyridin-2-yl-isoxazole-4-carboxylic acid ethyl ester (9.52 g, 44 mmol) in THF (530 mL) was added a solution of lithium hydroxide monohydrate (11.0 g, 263 mmol) in water (265 mL) followed by methanol (265 mL) at 0° C. and the resulting mixture stirred at room temperature for 1 h. The mixture was then evaporated to half volume and then acidified to pH 4 with HCl (1N) and cooled to 0° C. for 30 min. A solid precipitated and was filtered off and dried to afford the title compound (6.55 g, 79%) which was obtained as an off white solid. MS: m/e=189.3 [M–H]⁻.

c) (3-Pyridin-2-yl-isoxazol-4-yl)-methanol

To a solution of 3-pyridin-2-yl-isoxazole-4-carboxylic acid (39.0 g, 200 mmol) in THF (480 mL) at –10° C. was added triethylamine (30.7 mL, 220 mmol) and then a solution of ethylchloroformate (20.0 mL, 210 mmol) in THF (120 mL) added keeping the temperature below –5° C. After 1 h the mixture was filtered and the filtrate cooled to –10° C. and a suspension of sodiumborohydride (18.9 g, 500 mmol) in water (200 mL) added over 15 minutes keeping the temperature below –5° C. The mixture was then allowed to warm up to room temperature over 2 h and diluted with aqueous sodium hydroxide (2 N, 100 mL) and extracted with diethylether. The combined organic layers were then washed with water and brine, dried over sodium sulfate and evaporated. Purification by chromatography (SiO₂, heptane:ethyl acetate=1:1 to 1:2) afforded the title product (26.8 g, 76%) which was obtained as white solid. MS: m/e=177.2 [M]⁺.

d) 2-(4-Chloromethyl-isoxazol-3-yl)-pyridine

To a solution of (3-pyridin-2-yl-isoxazol-4-yl)-methanol (3.0 g, 16 mmol) in DCM (30 mL) at 0° C. was added thionyl chloride (3.75 g, 32 mmol) and the resulting mixture stirred for 1 h and then evaporated. After 1 h the reaction mixture was quenched with a solution of sodium hydrogen carbonate (1 N, 15 mL) and extracted with ethyl acetate. The combined extracts were washed with water, dried over sodium sulfate, filtered and concentrated to give the title compound (3.2 g, 96%) as a grey solid. MS: m/e=195.1 [M+H]⁺.

e) 4-Methyl-2-[2-(3-pyridin-2-yl isoxazol-4-yl)-ethyl]-thiazole-5-carboxylic acid methyl ester To a stirred solution of 2,4-dimethyl-thiazole-5-carboxylic acid (1.21 g, 8.0 mmol) in THF (66 mL) at –75° C. and under argon was added BuLi (1.6M in hexanes, 9.63 mL, 15.0 mmol) dropwise. After 2 h a solution of 2-(4-chloromethyl-isoxazol-3-yl)-pyridine (1.5 g, 8.0 mmol) in THF (28 mL) was added dropwise. After 3 h at –75° C. the reaction mixture was quenched with citric acid solution (5%, 45 mL) then warmed to room temperature and extracted with ethyl acetate. The combined extracts were dried, filtered and concentrated to give the intermediate acid compound (2.78 g) as a light brown solid. To a solution of intermediate acid (2.78 g) in MeOH (58 mL) and diethylether (32 mL) was added trimethylsilyldiazomethane (2M in diethylether, 23.1 mL, 4.6 mmol) in two portions under ice cooling. Then the reaction mixture was quenched by addition of acetic acid (conc., 0.7 mL), evaporated and extracted with ethyl acetate. The combined extracts were washed with NaOH (1N), water, dried over sodium sulfate, filtered and concentrated. Purification by chromatography (silica, heptane:ethyl acetate 8:2 to 1:1) afforded the title compound (685 mg, 27%) as a light brown solid. MS: m/e=330.0 [M+H]⁺.

f) 4-methyl-2-[2-(3-pyridin-2-yl-isoxazol-4-yl)-ethyl]-thiazole-5-carboxylic acid To a suspension of 4-methyl-2-[2-(3-pyridin-2-yl-isoxazol-4-yl)-ethyl]-thiazole-5-carboxylic acid methyl ester (647 mg, 2.0 mmol) in THF (6.5 mL) was added a solution of lithium hydroxide monohydrate (165 mg, 3.9 mmol) in water (6.5 mL) followed by methanol (4 mL) and the resulting mixture stirred at room temperature for 4 h. The mixture was then evaporated to half volume and then acidified to pH 4 with HCl (1N) and cooled to 0° C. for 30 min. A solid precipitated and was filtered off and dried to afford the title compound (578 mg, 93%) which was obtained as a light brown solid. MS: m/e=314.1 [M–H]⁻.

g) 4-Methyl-2-[2-(3-pyridin-2-yl-isoxazol-4-yl)-ethyl]-thiazole-5-carboxylic acid (tetra-hydro-pyran-4-yl)-amide To a solution of 4-methyl-2-[2-(3-pyridin-2-yl-isoxazol-4-yl)-ethyl]-thiazole-5-carboxylic acid (70 mg, 0.22 mmol) in DMF (2 mL) were added 2-(1H-benzotriazole-1-yl)-1,1,3,3-tetramethyluronium tetrafluoroborate (79 mg, 0.24 mmol), N,N-diisopropyl ethyl amine (190 µL, 1.11 mmol) and 4-aminotetrahydropyran (25 mg, 0.24 mmol). The resulting reaction mixture was stirred overnight and then evaporated. Purification by chromatography (silica, heptane:ethyl acetate 8:2 to 1:1) afforded the title compound (84 mg, 95%) as a white solid. S: m/e=399.2 [M+H]⁺.

Example 20

4-Methyl-2-[2-(3-pyridin-2-yl-isoxazol-4-yl)-ethyl]-thiazole-5-carboxylic acid (2,2,2-trifluoro-ethyl)-amide

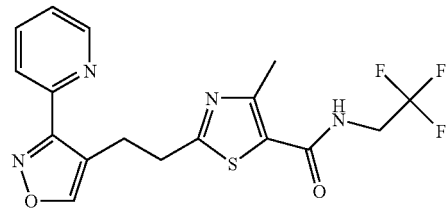

As described for example 19, 4-methyl-2-[2-(3-pyridin-2-yl-isoxazol-4-yl)-ethyl]-thiazole-5-carboxylic acid (70 mg, 0.22 mmol) was converted, using 2,2,2-trifluoroethylamine instead of 4-aminotetrahydropyran, to the title compound (82 mg, 93%) which was obtained as an off white solid MS: m/e=397.1 [M+H]⁺.

Example 21

2-[2-(5-Methyl-3-pyridin-2-yl-isoxazol-4-yl)-ethyl]-thiazole-5-carboxylic acid methyl ester

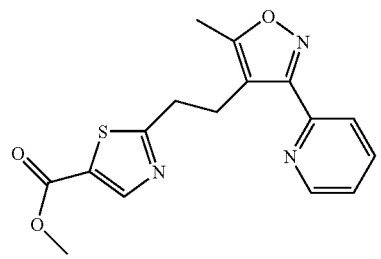

To a stirred solution of 2-methyl-thiazole-5-carboxylic acid (1.03 g, 7.0 mmol) in THF (61 mL) at −70° C. and under argon was added BuLi (1.6M in hexanes, 8.99 mL, 14.0 mmol) dropwise. After 2 h a solution of 2-(4-chloromethyl-5-methyl-isoxazol-3-yl)-pyridine (1.5 g, 7.0 mmol) in THF (26 mL) was added dropwise. After 3 h the reaction mixture was quenched with citric acid solution (5%, 10 mL) then warmed to room temperature and extracted with ethyl acetate. The combined extracts were dried, filtered and concentrated to give the intermediate acid compound (2.43 g) as a light brown solid. To a solution of intermediate acid (2.43 g) in MeOH (54 mL) and diethylether (30 mL) was added trimethylsilyldiazomethane (2M in diethylether, 21.6 mL, 4.3 mmol) in two portions under ice cooling. Then the reaction mixture was quenched by addition of acetic acid (conc., 0.7 mL), evaporated and extracted with ethyl acetate. The combined extracts were washed with NaOH (1N), water, dried over sodium sulfate, filtered and concentrated. Purification by chromatography (silica, heptane:ethyl acetate 8:2 to 2:3) afforded the title compound (915 mg, 39%) as an orange solid. MS: m/e=330.0 [M+H]$^+$.

Example 22

2-[2-(5-Methyl-3-pyridin-2-yl-isoxazol-4-yl)-ethyl]-thiazole-5-carboxylic acid isopropylamide

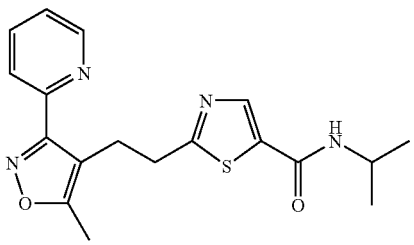

a) 2-[2-(5-Methyl-3-pyridin-2-yl-isoxazol-4-yl)-ethyl]-thiazole-5-carboxylic acid To a suspension of 2-[2-(5-methyl-3-pyridin-2-yl-isoxazol-4-yl)-ethyl]-thiazole-5-carboxylic acid methyl ester (835 mg, 2.54 mmol) in THF (8 mL) was added a solution of lithium hydroxide monohydrate (165 mg, 3.9 mmol) in water (8 mL) and the resulting mixture stirred at room temperature for 45 min. The mixture was then evaporated to half volume and then acidified to pH 1 with HCl (1N) and cooled to 0° C. for 15 min. A solid precipitated and was filtered off and dried to afford the title compound (769 mg, 96%) which was obtained as an off white solid. MS: m/e=314.1 [M−H]$^-$.

b) 2-[2-(5-Methyl-3-pyridin-2-yl-isoxazol-4-yl)-ethyl]-thiazole-5-carboxylic acid iso-propylamide To a solution of 2-[2-(5-methyl-3-pyridin-2-yl-isoxazol-4-yl)-ethyl]-thiazole-5-carboxylic acid (77 mg, 0.24 mmol) in DMF (3 mL) were added 2-(1H-benzotriazole-1-yl)-1,1,3,3-tetramethyluronium tetrafluoroborate (86 mg, 0.27 mmol), N,N-diisopropyl ethyl amine (208 μL, 1.21 mmol) and iso-propylamine (16 mg, 0.27 mmol). The resulting reaction mixture was stirred for 2 h and then evaporated. Purification by chromatography (silica, heptane:ethyl acetate 1:1 to 0:1) afforded the title compound (81 mg, 93%) as an off white solid. MS: m/e=357.2 [M+H]$^+$.

Example 23

2-[2-(5-Methyl-3-pyridin-2-yl-isoxazol-4-yl)-ethyl]-thiazole-5-carboxylic acid cyclo-propylamide

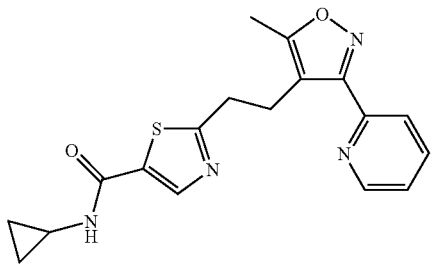

As described for example 22b, 2-[2-(5-methyl-3-pyridin-2-yl-isoxazol-4-yl)-ethyl]-thiazole-5-carboxylic acid (73 mg, 0.23 mmol) was converted, using cyclopropylamine instead of isopropylamine, to the title compound (66 mg, 80%) which was obtained as an off white solid MS: m/e=355.2 [M+H]$^+$.

Example 24

2-[2-(5-Methyl-3-pyridin-2-yl-isoxazol-4-yl)-ethyl]-thiazole-5-carboxylic acid (tetra-hydro-pyran-4-yl)-amide

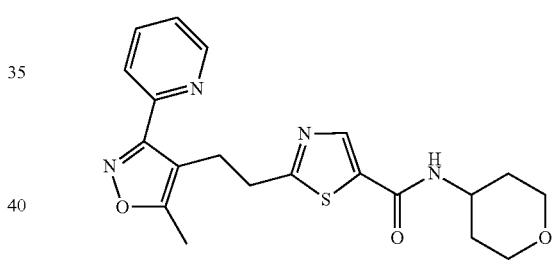

As described for example 22b, 2-[2-(5-methyl-3-pyridin-2-yl-isoxazol-4-yl)-ethyl]-thiazole-5-carboxylic acid (77 mg, 0.24 mmol) was converted, using 4-aminotetrahydropyran instead of isopropylamine, to the title compound (45 mg, 46%) which was obtained as a white solid MS: m/e=399.1 [M+H]$^+$.

Example 25

2-[2-(5-Methyl-3-pyridin-2-yl-isoxazol-4-yl)-ethyl]-thiazole-5-carboxylic acid amide

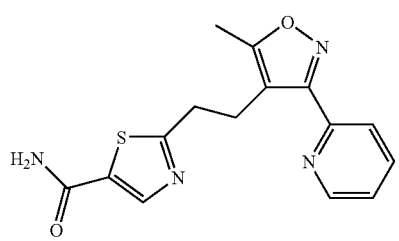

To a solution of 2-[2-(5-methyl-3-pyridin-2-yl-isoxazol-4-yl)-ethyl]-thiazole-5-carboxylic acid (73 mg, 0.23 mmol) in DMF (3 mL) was added 1,1'-carbonyldiimidazole (45 mg, 0.28 mmol). The resulting reaction mixture was stirred for 1 h at 60° C. and then treated with an ammonium hydroxide solution (357 µL, 2.3 mmol) and stirred overnight at room temperature. The reaction mixture was then evaporated. Purification by chromatography (silica, 0 to 10% methanol in dichloromethane) afforded the title compound (51 mg, 70%) as an off white solid. MS: m/e=315.0 [M+H]$^+$.

Example 26

2-[2-(5-Methyl-3-pyridin-2-yl-isoxazol-4-yl)-ethyl]-thiazole-5-carboxylic acid cyclo-propylmethyl-amide

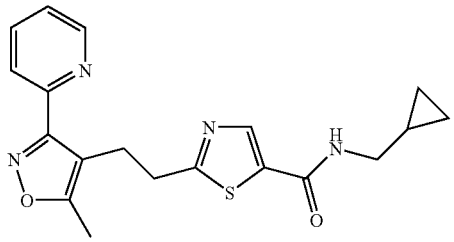

As described for example 22b, 2-[2-(5-methyl-3-pyridin-2-yl-isoxazol-4-yl)-ethyl]-thiazole-5-carboxylic acid (73 mg, 0.23 mmol) was converted, using 2-cyclopropylethylamine instead of isopropylamine, to the title compound (70 mg, 82%) which was obtained as a white solid. MS: m/e=369.1 [M+H]$^+$.

Example 27

2-[2-(5-Methyl-3-pyridin-2-yl-isoxazol-4-yl)-ethyl]-thiazole-5-carboxylic acid (1,1-dioxo-tetrahydrothiophen-3-yl)-amide

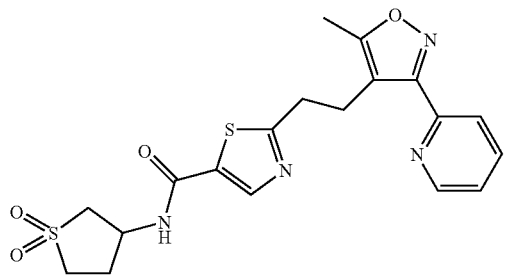

As described for example 22b, 2-[2-(5-methyl-3-pyridin-2-yl-isoxazol-4-yl)-ethyl]-thiazole-5-carboxylic acid (73 mg, 0.23 mmol) was converted, using 1,1-dioxidotetrahydrothien-3-ylamine instead of isopropylamine, to the title compound (37 mg, 37%) which was obtained as a brown solid MS: m/e=433.3 [M+H]$^+$.

Example 28

2-[2-(5-Methyl-3-pyridin-2-yl-isoxazol-4-yl)-ethyl]-thiazole-5-carboxylic acid (2,2,2-trifluoro-ethyl)-amide

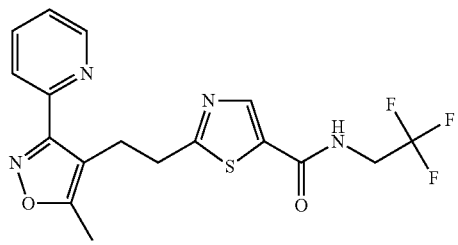

As described for example 22b, 2-[2-(5-methyl-3-pyridin-2-yl-isoxazol-4-yl)-ethyl]-thiazole-5-carboxylic acid (73 mg, 0.23 mmol) was converted, using 2,2,2-trifluoroethylamine instead of isopropylamine, to the title compound (72 mg, 79%) which was obtained as an off white solid MS: m/e=397.2 [M+H]$^+$.

Example 29

2-[2-(5-Methyl-3-pyridin-2-yl-isoxazol-4-yl)-ethyl]-thiazole-5-carboxylic acid (2-hydroxy-ethyl)-amide

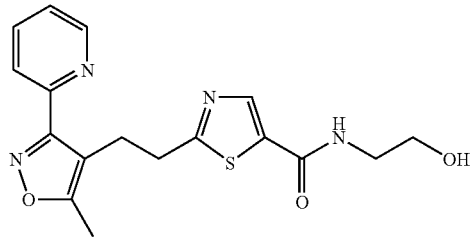

As described for example 22b, 2-[2-(5-methyl-3-pyridin-2-yl-isoxazol-4-yl)-ethyl]-thiazole-5-carboxylic acid (73 mg, 0.23 mmol) was converted, using ethanolamine instead of isopropylamine, to the title compound (29 mg, 35%) which was obtained as a white solid MS: m/e=359.1 [M+H]$^+$.

Example 30

2-{2-[3-(5-Fluoro-pyridin-2-yl)-5-methyl-isoxazol-4-yl]-ethyl}-4-methyl-thiazole-5-carboxylic acid methyl ester

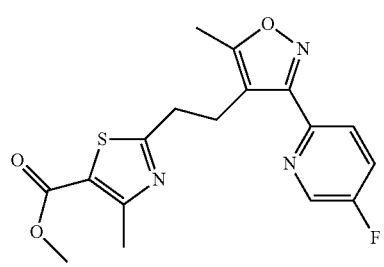

a) 5-Fluoro-pyridine-2-carbaldehyde oxime

To a solution of 5-fluoro-2-formylpyridine (5.0 g, 41 mmol) and hydroxylamine hydrochloride (3.06 g, 44 mmol) in ethanol (3.2 mL) and water (9.6 mL) was added ice (18.6 g). Then a solution of NaOH (4.0 g, 100 mmol) in water (4.6 mL) was added dropwise over 10 min keeping the temperature between −5° C. and 5° C. The reaction mixture was then stirred at room temperature for 30 min. Then HCl (4 N) was added to acidify the mixture and the resulting precipitate was filtered off and washed with water to afford the title compound (4.41 g, 79%) as a light brown solid. MS: m/e=141.0 $[M+H]^+$.

b) 3-(5-Fluoro-pyridin-2-yl)-5-methyl-isoxazole-4-carboxylic acid ethyl ester To a suspension of N-chlorosuccinimide (4.63 g, 35 mmol) in chloroform (21 mL) was added pyridine (0.28 mL, 3.5 mmol) and a solution of 5-fluoro-pyridine-2-carbaldehyde oxime (4.86 g, 35 mmol) in chloroform (110 mL) during 15 min at room temperature. After stirring for 30 min at this temperature a solution of ethyl(E)-3-(1-pyrrolidino)-2-butenoate (6.36 g, 35 mmol) in chloroform (4.4 mL) was added. The resulting suspension was warmed to 50° C. and a solution of triethylamine (4.83 mL, 35 mmol) in chloroform (4.4 mL) was added dropwise over a period of 30 min. Stirring was continued for 1.5 h at 50° C. and then cooled to ambient temperature. The solution was then diluted with ice-water (200 mL) and the aqueous layers were extracted with dichloromethane (50 mL) and dried over sodium sulfate and evaporation to give a dark brown oil. Purification by chromatography (silica, heptane:ethyl acetate=100:0 to 20:80) afforded the title compound (5.83 g, 67%) as yellow oil. MS: m/e=251.1 $[M+H]^+$.

c) [3-(5-Fluoro-pyridin-2-yl)-5-methyl-isoxazol-4-yl]-methanol

To a solution of 3-(5-fluoro-pyridin-2-yl)-5-methyl-isoxazole-4-carboxylic acid ethyl ester (2.5 g, 10 mmol) in dry THF (34 mL), cooled to 0° C., was added lithiumaluminumhydride (209 mg, 2.3 mmol) portionwise. After allowing to warm up to room temperature over 1 h, the mixture was cooled to 0° C. and water (0.2 mL) was added carefully followed by aqueous sodium hydroxide (15%, 0.2 mL) and water (0.6 mL). The resulting suspension was stirred for 4 h at ambient temperature and filtered over Hyflo®. The filtrate was then concentrated and purification by chromatography (silica, heptane:ethyl acetate=50:50 to 0:100) afforded the title compound (1.47 g, 71%) as a light yellow solid. MS: m/e=209.1 $[M+H]^+$.

d) 2-(4-Chloromethyl-5-methyl-isoxazol-3-yl)-5-fluoro-pyridine

To a solution of [3-(5-fluoro-pyridin-2-yl)-5-methyl-isoxazol-4-yl]-methanol (1.0 g, 4.8 mmol) in DCM (9.6 mL) at 0° C. was added thionyl chloride (697 µL, 9.6 mmol) and the resulting mixture stirred for 30 min and then evaporated. After 1 h the reaction mixture was concentrated to give the title compound (1.07 g, 98%) as an off white solid. MS: m/e=227.2 $[M+H]^+$.

e) 2-{2-[3-(5-Fluoro-pyridin-2-yl)-5-methyl-isoxazol-4-yl]-ethyl}-4-methyl-thiazole-5-carboxylic acid methyl ester To a stirred solution of 2,4-dimethylthiazole-5-carboxylic acid (710 mg, 4.52 mmol) in THF (38 mL) at −70° C. and under argon was added BuLi (1.6M in hexanes, 5.65 mL, 9.04 mmol) dropwise. After 2 h at −75° C. a solution of 2-(4-chloromethyl-5-methyl-isoxazol-3-yl)-5-fluoro-pyridine (1.02 g, 4.52 mmol) in THF (14 mL) was added dropwise. After 3 h the reaction mixture was quenched with citric acid solution (5%, 30 mL) then warmed to room temperature and extracted with ethyl acetate. The combined extracts were dried, filtered and concentrated to give the intermediate acid compound (1.76 g) as a yellow solid. To a solution of intermediate acid (1.76 g) in MeOH (34 mL) and diethylether (19 mL) was added trimethylsilyldiazomethane (2M in diethylether, 3×4.5 mL, 27.12 mmol) under ice cooling. Then the reaction mixture was quenched by addition of acetic acid (conc., 0.7 mL), evaporated and extracted with ethyl acetate. The combined extracts were washed with NaOH (1 N), water, dried over sodium sulfate, filtered and concentrated. Purification by chromatography (silica, heptane:ethyl acetate 1:0 to 0:1) afforded the title compound (1.09 g, 67%) as an orange solid. MS: m/e=362.2 $[M+H]^+$.

Example 31

2-{2-[3-(5-Fluoro-pyridin-2-yl)-5-methyl-isoxazol-4-yl]ethyl}-4-methyl-thiazole-5-carboxylic acid (tetrahydro-pyran-4-yl)-amide

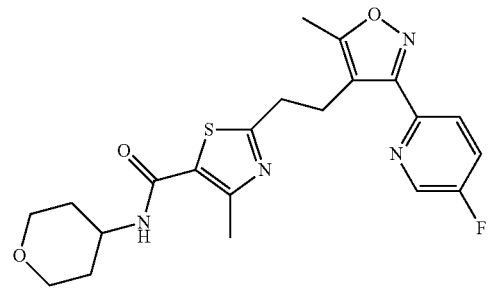

a) 2-{2-[3-(5-Fluoro-pyridin-2-yl)-5-methyl-isoxazol-4-yl]-ethyl}-4-methyl-thiazole-5-carboxylic acid To a suspension of 2-{2-[3-(5-fluoro-pyridin-2-yl)-5-methyl-isoxazol-4-yl]-ethyl}-4-methyl-thiazole-5-carboxylic acid methyl ester (1.02 g, 2.82 mmol) in THF (7 mL), water (7 mL) and MeOH (1.4 mL) was added lithium hydroxide monohydrate (237 mg, 5.65 mmol) and the resulting mixture stirred at room temperature overnight. The mixture was then evaporated to half volume and then acidified to pH 1 with HCl (1 N) and cooled to 0° C. for 15 min. A solid precipitated and was filtered off and dried to afford the title compound (867 mg, 88%) which was obtained as an off white solid. MS: m/e=346.2 $[M-H]^-$.

b) 2-{2-[3-(5-Fluoro-pyridin-2-yl)-5-methyl-isoxazol-4-yl]-ethyl}-4-methyl-thiazole-5-carboxylic acid (tetrahydro-pyran-4-yl)-amide To a solution of 2-{2-[3-(5-fluoro-pyridin-2-yl)-5-methyl-isoxazol-4-yl]-ethyl}-4-methyl-thiazole-5-carboxylic acid (69 mg, 0.20 mmol) in DMF (1.2 mL) were added 2-(1H-benzotriazole-1-yl)-1,1,3,3-tetramethyluronium tetrafluoroborate (71 mg, 0.22 mmol), N,N-diisopropyl ethyl amine (171 µL, 1.00 mmol) and 4-aminotetrahydropyran (22 mg, 0.22 mmol). The resulting reaction mixture was stirred for 1 h and then evaporated. Purification by chromatography (silica, heptane:ethyl acetate 4:1 to 0:1) afforded the title compound (81 mg, 94%) as an off white solid. MS: m/e=431.2 $[M+H]^+$.

Example 32

2-{2-[3-(5-Fluoro-pyridin-2-yl)-5-methyl-isoxazol-4-yl]-ethyl}-4-methyl-thiazole-5-carboxylic acid isopropylamide

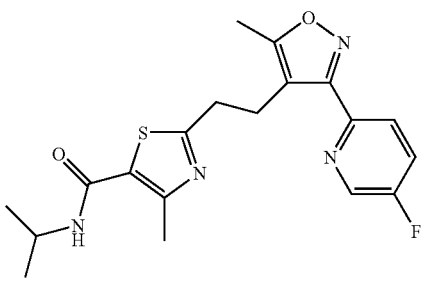

As described for example 31b, 2-{2-[3-(5-fluoro-pyridin-2-yl)-5-methyl-isoxazol-4-yl]-ethyl}-4-methyl-thiazole-5-carboxylic acid (69 mg, 0.20 mmol) was converted, using isopropylamine instead of 4-aminotetrahydropyran, to the title compound (71 mg, 91%) which was obtained as an off white solid. MS: m/e=389.2 [M+H]$^+$.

Example 33

2-{2-[3-(5-Fluoro-pyridin-2-yl)-5-methyl-isoxazol-4-yl]-ethyl}-4-methyl-thiazole-5-carboxylic acid cyclopropylamide

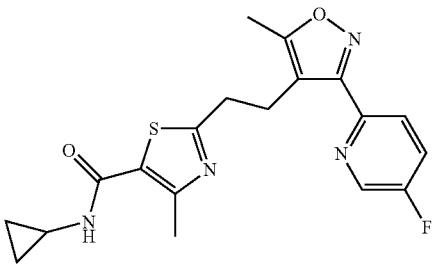

As described for example 31b, 2-{2-[3-(5-fluoro-pyridin-2-yl)-5-methyl-isoxazol-4-yl]-ethyl}-4-methyl-thiazole-5-carboxylic acid (69 mg, 0.20 mmol) was converted, using cyclopropylamine instead of 4-aminotetrahydropyran, to the title compound (63 mg, 82%) which was obtained as an off white solid. MS: m/e=387.2 [M+H]$^+$.

Example 34

2-{2-[3-(5-Fluoro-pyridin-2-yl)-5-methyl-isoxazol-4-yl]-ethyl}-4-methyl-thiazole-5-carboxylic acid cyclopropylmethyl-amide

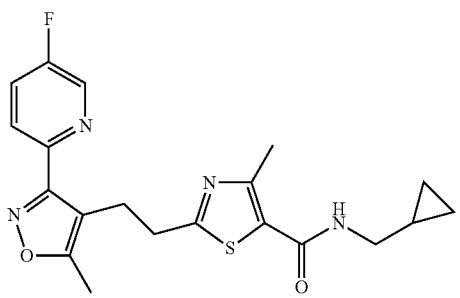

As described for example 31b, 2-{2-[3-(5-fluoro-pyridin-2-yl)-5-methyl-isoxazol-4-yl]-ethyl}-4-methyl-thiazole-5-carboxylic acid (69 mg, 0.20 mmol) was converted, using aminomethylcyclopropane instead of 4-aminotetrahydropyran, to the title compound (68 mg, 85%) which was obtained as an off white solid. MS: m/e=401.1 [M+H]$^+$.

Example 35

2-{2-[3-(5-Fluoro-pyridin-2-yl)-5-methyl-isoxazol-4-yl]ethyl}-4-methyl-thiazole-5-carboxylic acid (2,2,2-trifluoro-ethyl)-amide

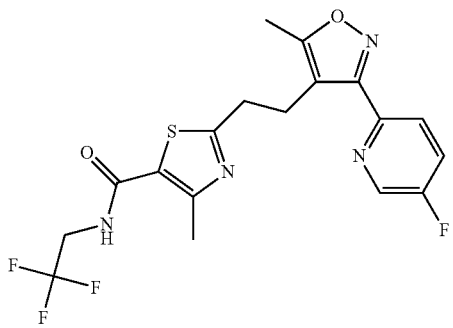

As described for example 31b, 2-{2-[3-(5-fluoro-pyridin-2-yl)-5-methyl-isoxazol-4-yl]-ethyl}-4-methyl-thiazole-5-carboxylic acid (69 mg, 0.20 mmol) was converted, using 2,2,2-trifluoroethylamine instead of 4-aminotetrahydropyran, to the title compound (77 mg, 90%) which was obtained as an off white solid. MS: m/e=429.2 [M+H]$^+$.

Example 36

2-{2-[3-(5-Fluoro-pyridin-2-yl)-5-methyl-isoxazol-4-yl]-ethyl}-4-methyl-thiazole-5-carboxylic acid (2-hydroxy-ethyl)-amide

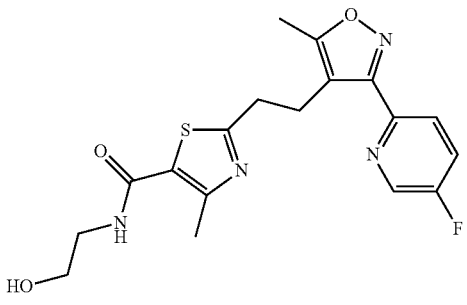

As described for example 31b, 2-{2-[3-(5-fluoro-pyridin-2-yl)-5-methyl-isoxazol-4-yl]-ethyl}-4-methyl-thiazole-5-carboxylic acid (69 mg, 0.20 mmol) was converted, using ethanolamine instead of 4-aminotetrahydropyran, to the title compound (62 mg, 79%) which was obtained as an off white solid. MS: m/e=391.2 [M+H]$^+$.

Example 37

(2-{2-[3-(5-Fluoro-pyridin-2-yl)-5-methyl-isoxazol-4-yl]-ethyl}-4-methyl-thiazol-5-yl)-thiomorpholin-4-yl-methanone

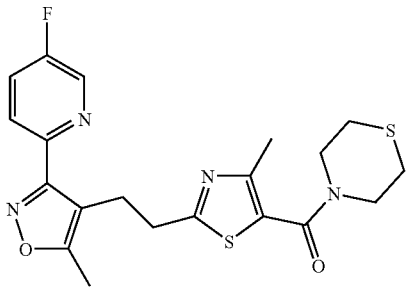

As described for example 31b, 2-{2-[3-(5-fluoro-pyridin-2-yl)-5-methyl-isoxazol-4-yl]-ethyl}-4-methyl-thiazole-5-carboxylic acid (69 mg, 0.20 mmol) was converted, using thiomorpholine instead of 4-aminotetrahydropyran, to the title compound (32 mg, 37%) which was obtained as a colourless gum after purification by chromatography (silica, heptane:ethyl acetate 1:0 to 0:1 then dichloromethane:methanol 1:0 to 95:5). MS: m/e=433.2 [M+H]$^+$.

Example 38

2-{2-[3-(5-Fluoro-pyridin-2-yl)-5-methyl-isoxazol-4-yl]-ethyl}-4-methyl-thiazole-5-carboxylic acid ethylamide

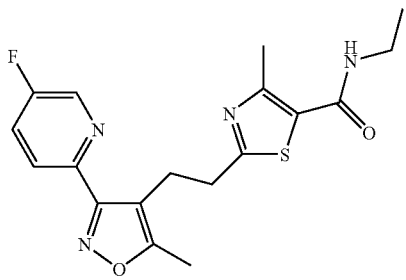

As described for example 31b, 2-{2-[3-(5-fluoro-pyridin-2-yl)-5-methyl-isoxazol-4-yl]-ethyl}-4-methyl-thiazole-5-carboxylic acid (69 mg, 0.20 mmol) was converted, using ethylamine (2M solution in THF) instead of 4-aminotetrahydropyran, to the title compound (48 mg, 64%) which was obtained as an off white solid. MS: m/e=375.2 [M+H]$^+$.

Example 39

2-{2-[3-(5-Fluoro-pyridin-2-yl)-5-methyl-isoxazol-4-yl]-ethyl}-4-methyl-thiazole-5-carboxylic acid methylamide

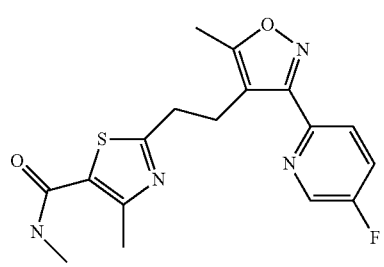

As described for example 31b, 2-{2-[3-(5-fluoro-pyridin-2-yl)-5-methyl-isoxazol-4-yl]-ethyl}-4-methyl-thiazole-5-carboxylic acid (69 mg, 0.20 mmol) was converted, using methylamine (2M solution in THF) instead of 4-aminotetrahydropyran, to the title compound (34 mg, 47%) which was obtained as an off white solid. MS: m/e=361.2 [M+H]$^+$.

Example 40

2-{2-[3-(5-Fluoro-pyridin-2-yl)-5-methyl-isoxazol-4-yl]-ethyl}-thiazole-5-carboxylic acid (tetrahydro-pyran-4-yl)-amide

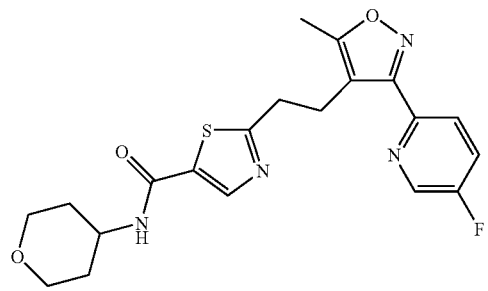

a) 2-{2-[3-(5-Fluoro-pyridin-2-yl)-5-methyl-isoxazol-4-yl]-ethyl}-thiazole-5-carboxylic acid methyl ester To a stirred solution of 2-methyl-thiazole-5-carboxylic acid (1.37 g, 9.58 mmol) in THF (80 mL) at −70° C. and under argon was added BuLi (1.6M in hexanes, 12 mL, 19.15 mmol) dropwise. After 2 h at −75° C. a solution of 2-(4-chloromethyl-5-methyl-isoxazol-3-yl)-5-fluoro-pyridine (2.17 g, 9.58 mmol) in THF (30 mL) was added dropwise. After 4 h the reaction mixture was quenched with citric acid solution (5%, 60 mL) then warmed to room temperature and extracted with ethyl acetate. The combined extracts were dried, filtered and concentrated to give the intermediate acid compound (4.12 g) as a yellow solid. To a solution of intermediate acid (4.12 g) in MeOH (72 mL) and diethylether (40 mL) was added trimethylsilyldiazomethane (2M in diethyl-ether, 3×9.6 mL, 57.48 mmol) under ice cooling. Then the reaction mixture was quenched by addition of acetic acid (conc., 0.7 mL), evaporated and extracted with ethyl acetate. The combined extracts were washed with NaOH (1 N, 100 mL), water, dried over sodium sulfate, filtered and concentrated. Purification by chromatography (silica, heptane:ethyl acetate 1:0 to 0:1) afforded the title compound (1.37 g, 41%) as a yellow solid. MS: m/e=348.1 [M+H]$^+$.

b) 2-{2-[3-(5-Fluoro-pyridin-2-yl)-5-methyl-isoxazol-4-yl]-ethyl}-thiazole-5-carboxylic acid To a solution of 2-{2-[3-(5-fluoro-pyridin-2-yl)-5-methyl-isoxazol-4-yl]-ethyl}-thiazole-5-carboxylic acid methyl ester (1.27 g, 3.66 mmol) in THF (9 mL) was added a solution of lithium hydroxide monohydrate (307 mg, 7.31 mmol) in water (9 mL) and the resulting mixture stirred at room temperature for 2 h. The mixture was then evaporated to half volume and then acidified to pH 1 with HCl (1 N) and cooled to 0° C. for 15 min. A solid precipitated and was filtered off and dried to afford the title compound (707 mg, 58%) which was obtained as an off white solid after recrystallization from ethyl acetate. MS: m/e=332.3 [M−H]$^−$.

c) 2-{2-[3-(5-Fluoro-pyridin-2-yl)-5-methyl-isoxazol-4-yl]-ethyl}-thiazole-5-carboxylic acid (tetrahydro-pyran-4-yl)-amide To a solution of 2-{2-[3-(5-fluoro-pyridin-2-yl)-5-methyl-isoxazol-4-yl]-ethyl}-thiazole-5-carboxylic acid (67 mg, 0.20 mmol) in DMF (1.2 mL) were added 2-(1H-benzotriazole-1-yl)-1,1,3,3-tetramethyluronium tetrafluoroborate (71 mg, 0.22 mmol), N,N-diisopropyl ethyl amine (171 µL, 1.00 mmol) and 4-aminotetrahydropyran (22 mg, 0.22 mmol). The resulting reaction mixture was stirred for 1 h and then evaporated. Purification by chromatography (silica, heptane:ethyl acetate 4:1 to 0:1) afforded the title compound (64 mg, 77%) as a white solid after recrystallization from ethyl acetate:heptane. MS: m/e=417.2 [M+H]$^+$.

Example 41

2-{2-[3-(5-Fluoro-pyridin-2-yl)-5-methyl-isoxazol-4-yl]-ethyl}-thiazole-5-carboxylic acid isopropylamide

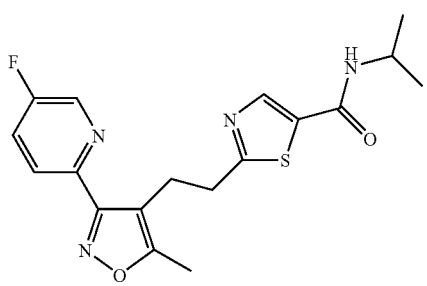

As described for example 40c, 2-{2-[3-(5-fluoro-pyridin-2-yl)-5-methyl-isoxazol-4-yl]-ethyl}-thiazole-5-carboxylic acid (67 mg, 0.20 mmol) was converted, using isopropylamine instead of 4-aminotetrahydropyran, to the title compound (42 mg, 51%) which was obtained as a white solid. MS: m/e=375.3 [M+H]$^+$.

Example 42

2-{2-[3-(5-Fluoro-pyridin-2-yl)-5-methyl-isoxazol-4-yl]-ethyl}-thiazole-5-carboxylic acid cyclopropylamide

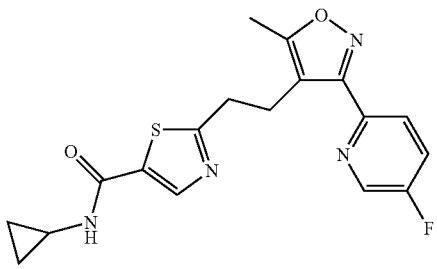

As described for example 40c, 2-{2-[3-(5-fluoro-pyridin-2-yl)-5-methyl-isoxazol-4-yl]-ethyl}-thiazole-5-carboxylic acid (67 mg, 0.20 mmol) was converted, using cyclopropylamine instead of 4-aminotetrahydropyran, to the title compound (42 mg, 55%) which was obtained as a white solid. MS: m/e=373.1 [M+H]$^+$.

Example 43

2-{2-[3-(5-Fluoro-pyridin-2-yl)-5-methyl-isoxazol-4-yl]-ethyl}-thiazole-5-carboxylic acid cyclopropylmethyl-amide

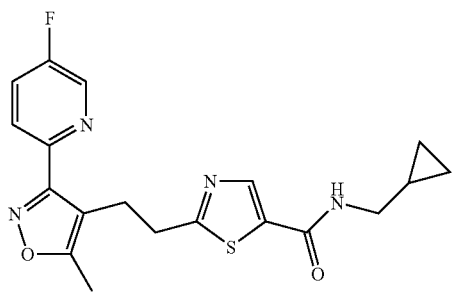

As described for example 40c, 2-{2-[3-(5-fluoro-pyridin-2-yl)-5-methyl-isoxazol-4-yl]-ethyl}-thiazole-5-carboxylic acid (67 mg, 0.20 mmol) was converted, using aminomethylcyclopropane instead of 4-aminotetrahydropyran, to the title compound (39 mg, 50%) which was obtained as a white solid. MS: m/e=387.2 [M+H]$^+$.

Example 44

2-{2-[3-(5-Fluoro-pyridin-2-yl)-5-methyl-isoxazol-4-yl]-ethyl}-thiazole-5-carboxylic acid (2,2,2-trifluoro-ethyl)-amide

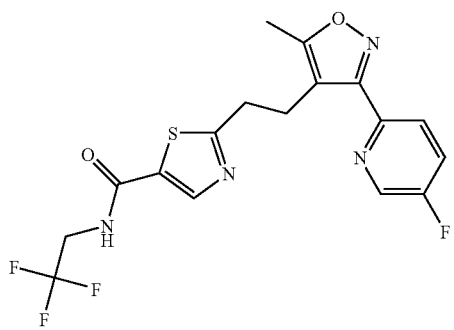

As described for example 40c, 2-{2-[3-(5-fluoro-pyridin-2-yl)-5-methyl-isoxazol-4-yl]-ethyl}-thiazole-5-carboxylic acid (67 mg, 0.20 mmol) was converted, using 2,2,2-trifluoroethylamine instead of 4-aminotetrahydropyran, to the title compound (56 mg, 68%) which was obtained as a white solid. MS: m/e=415.2 [M+H]$^+$.

Example 45

2-{2-[3-(5-Fluoro-pyridin-2-yl)-5-methyl-isoxazol-4-yl]-ethyl}-thiazole-5-carboxylic acid (2-hydroxy-ethyl)-amide

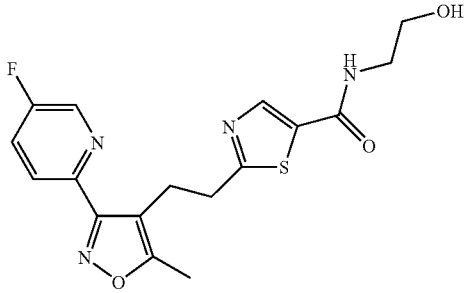

As described for example 40c, 2-{2-[3-(5-fluoro-pyridin-2-yl)-5-methyl-isoxazol-4-yl]-ethyl}-thiazole-5-carboxylic acid (67 mg, 0.20 mmol) was converted, using ethanolamine instead of 4-aminotetrahydropyran, to the title compound (65 mg, 41%) which was obtained as a white solid. MS: m/e=377.2 [M+H]$^+$.

Example 46

2-{2-[3-(5-Fluoro-pyridin-2-yl)-5-methyl-isoxazol-4-yl]-ethyl}-thiazole-5-carboxylic acid ethylamide

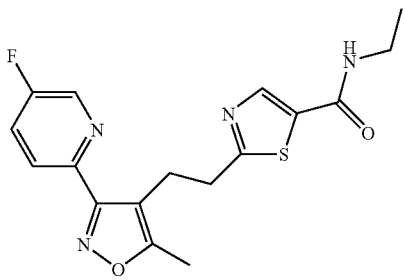

As described for example 40c, 2-{2-[3-(5-fluoro-pyridin-2-yl)-5-methyl-isoxazol-4-yl]-ethyl}-thiazole-5-carboxylic acid (67 mg, 0.20 mmol) was converted, using ethylamine (2M solution in THF) instead of 4-aminotetrahydropyran, to the title compound (42 mg, 58%) which was obtained as a white solid. MS: m/e=361.2 [M+H]$^+$.

Example 47

2-{2-[3-(5-Fluoro-pyridin-2-yl)-5-methyl-isoxazol-4-yl]-ethyl}-thiazole-5-carboxylic acid methylamide

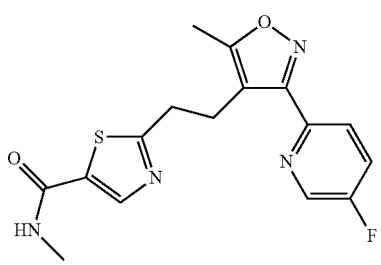

As described for example 40c, 2-{2-[3-(5-fluoro-pyridin-2-yl)-5-methyl-isoxazol-4-yl]-ethyl}-thiazole-5-carboxylic acid (67 mg, 0.20 mmol) was converted, using methylamine (2M solution in THF) instead of 4-aminotetrahydropyran, to the title compound (33 mg, 48%) which was obtained as a white solid. MS: m/e=347.0 [M+H]$^+$.

Example 48

2-[2-(3-Butyl-5-methyl-isoxazol-4-yl)-ethyl]-4-methyl-thiazole-5-carboxylic acid iso-propylamide

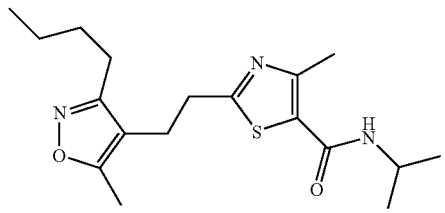

a) 3-Butyl-5-methyl-isoxazole-4-carboxylic acid ethyl ester

To a suspension of N-chlorosuccinimide (16.1 g, 121 mmol) in chloroform (250 mL) at room temperature was added pyridine (0.95 g, 12.0 mmol) then a solution of pentanal oxime (12.2 g, 121 mmol) in chloroform (250 mL) was added dropwise over 20 min. The reaction mixture was stirred at 50° C. for 2 h then cooled to room temperature and a solution of ethyl(E)-3-(1-pyrrolidino)-2-butenoate (22.1 g, 121 mmol) in chloroform (120 mL) added dropwise. The reaction mixture was warmed to 50° C. and a solution of triethylamine (12.2 g, 121 mmol) in chloroform (120 mL) added dropwise. After 15 h the reaction mixture was cooled and extracted with water then citric acid (10% w/w aqueous solution). The combined aqueous phases were extracted with dichloromethane, and the combined organic phases were dried, filtered and concentrated. Purification by chromatography (silica, heptane:ethyl acetate=100:0 to 9:1) afforded the title compound (10.9 g, 43%) as a pale yellow liquid. MS: m/e=232.2 [M+H]$^+$.

b) (3-Butyl-5-methyl-isoxazol-4-yl)-methanol

To a stirred solution of 3-butyl-5-methyl-isoxazole-4-carboxylic acid ethyl ester (9.8 g, 46.3 mmol) in THF (100 mL) under argon and at 0° C. was added lithiumaluminiumhydride (2.03 g, 53.4 mmol) in five portions. After 1 h the reaction mixture was quenched dropwise with Seignette salt solution. The reaction mixture was filtered and the filtrate extracted with ethyl acetate. The combined organic extracts were washed with Seignette salt solution then dried, filtered and concentrated. Purification by chromatography (silica, heptane:ethyl acetate=100:0 to 4:6) afforded the title compound (7.5 g, 95%) as a yellow liquid. MS: m/e=170.3 [M+H]$^+$.

c) 3-Butyl-4-chloromethyl-5-methyl-isoxazole

To a solution of (3-butyl-5-methyl-isoxazol-4-yl)-methanol (1.0 g, 6 mmol) in DCM (10 mL) at 0° C. was added thionyl chloride (1.46 g, 12 mmol) and the resulting mixture stirred for 1 h and then evaporated. After 1 h the reaction mixture was concentrated to give the title compound (1.04 g, 94%) as a light brown liquid. MS: m/e=188.2 [M+H]$^+$.

d) 2-[2-(3-Butyl-5-methyl-isoxazol-4-yl)-ethyl]-4-methyl-thiazole-5-carboxylic acid To a stirred solution of 2,4-dimethyl-thiazole-5-carboxylic acid (157 mg, 1.0 mmol) in THF (3 mL) at −78° C. and under argon was added LDA (1.0 mL of a 2M solution in THF, 2.0 mmol) dropwise. After 1.5 h a solution of 3-butyl-4-chloromethyl-5-methyl-isoxazole (188 mg, 1.0 mmol) in THF (2 mL) was added dropwise. After 1 h the reaction mixture was quenched with HCl (1 N, 10 mL) then warmed to room temperature and extracted with ethyl acetate. The combined extracts were dried, filtered and concentrated. Purification by chromatography (silica, 0 to 10% methanol in dichloromethane) gave the title compound (210 mg, 68%) as an off white solid. MS: m/e=307.3 [M+H]$^+$.

e) 2-[2-(3-Butyl-5-methyl-isoxazol-4-yl)-ethyl]-4-methyl-thiazole-5-carboxylic acid iso-propylamide To a stirred solution of isopropylamine (77 mg, 1.3 mmol) in dioxane (3 mL) under argon and at room temperature was added trimethylaluminium (0.65 mL of a 2M solution in toluene, 1.3 mmol). After 1 h, a solution of 2-[2-(3-butyl-5-methyl-isoxazol-4-yl)-ethyl]-4-methyl-thiazole-5-carboxylic acid (100 mg, 0.32 mmol) in dioxane (4 mL) was added and the reaction mixture heated at 90° C. overnight. The reaction mixture was then cooled, quenched with ice water and extracted with dichloromethane. The combined extracts were washed with Seignette's salt solution then dried, filtered, and concentrated. Purification by chromatography (silica, 0 to 5% methanol in dichloromethane) gave the title compound (50 mg, 44%) as a light yellow oil. MS: m/e=350.5 [M+H]$^+$.

Example 49

2-[2-(3-Butyl-5-methyl-isoxazol-4-yl)-ethyl]-4-methyl-thiazole-5-carboxylic acid (2-hydroxy-2-methyl-propyl)-amide

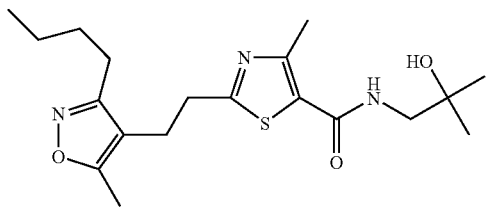

To a solution of 2-[2-(3-butyl-5-methyl-isoxazol-4-yl)-ethyl]-4-methyl-thiazole-5-carboxylic acid (80 mg, 0.26 mmol) in DMF (4 mL) were added 2-(1H-benzotriazole-1-yl)-1,1,3,3-tetramethyluronium tetrafluoroborate (92 mg, 0.29 mmol), N,N-diisopropyl ethyl amine (168 mg, 1.3 mmol) and 1-amino-2-methyl-propan-2-ol (25 mg, 0.29 mmol). The resulting reaction mixture was stirred for 15 h and then evaporated. Purification by chromatography (silica, 0 to 10% methanol in dichloromethane) afforded the title compound (55 mg, 56%) as a colourless oil MS: m/e=380.4 [M+H]$^+$.

Example 50

2-[2-(3-Butyl-5-methyl-isoxazol-4-yl)-ethyl]-4-methyl-thiazole-5-carboxylic acid (2-hydroxy-1-methyl-ethyl)-amide

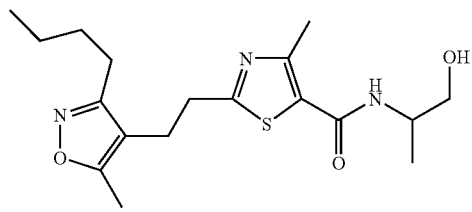

As described for example 49, 2-[2-(3-butyl-5-methyl-isoxazol-4-yl)-ethyl]-4-methyl-thiazole-5-carboxylic acid (80 mg, 0.26 mmol) was converted, using rac-2-amino-1-propanol instead of 1-amino-2-methyl-propan-2-ol, to the title compound (55 mg, 58%) which was obtained as a light brown oil. MS: m/e=366.1 [M+H]$^+$.

Example 51

2-[2-(3-Butyl-5-methyl-isoxazol-4-yl)-ethyl]-4-methyl-thiazole-5-carboxylic acid (tetra-hydro-pyran-4-yl)-amide

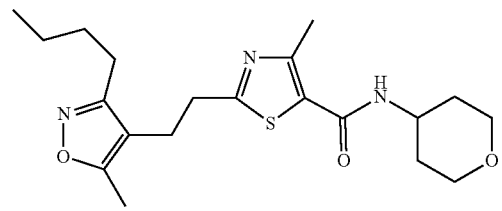

As described for example 48e, 2-[2-(3-butyl-5-methyl-isoxazol-4-yl)-ethyl]-4-methyl-thiazole-5-carboxylic acid (75 mg, 0.23 mmol) was converted, using 4-aminotetrahydropyran instead of isopropylamine, to the title compound (55 mg, 60%) which was obtained as a light brown oil. MS: m/e=392.1 [M+H]$^+$.

Example 52

Rac-2-[2-(3-Butyl-5-methyl-isoxazol-4-yl)-ethyl]-4-methyl-thiazole-5-carboxylic acid (tetrahydro-furan-3-yl)-amide

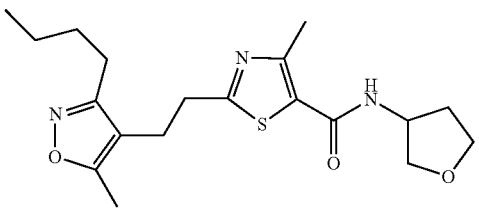

As described for example 48e, 2-[2-(3-butyl-5-methyl-isoxazol-4-yl)-ethyl]-4-methyl-thiazole-5-carboxylic acid (75 mg, 0.23 mmol) was converted, using rac-tetrahydrofuran-3-amine instead of isopropylamine, to the title compound (35 mg, 40%) which was obtained as a light brown oil. MS: m/e=378.3 [M+H]$^+$.

Example 53

2-[2-(3-Butyl-5-methyl-isoxazol-4-yl)-ethyl]-4-methyl-thiazole-5-carboxylic acid (2-hydroxy-1-hydroxymethyl-ethyl)-amide

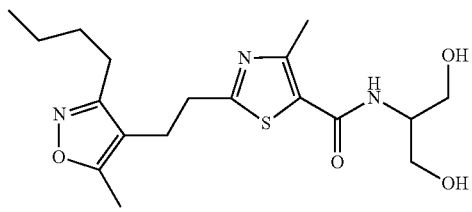

a) 2-[2-(3-Butyl-5-methyl-isoxazol-4-yl)-ethyl]-4-methyl-thiazole-5-carboxylic acid methyl ester To a stirred solution of 2,4-dimethylthiazole-5-carboxylic acid (1.26 g, 8.0 mmol) in THF (60 mL) at −78° C. and under argon was added BuLi (1.6M in hexanes, 10 mL, 16.0 mmol) dropwise. After 2 h at −75° C. a solution of 3-butyl-4-chloromethyl-5-methyl-isoxazole (1.5 g, 8.0 mmol) in THF (10 mL) was added dropwise. After 3.5 h the reaction mixture was quenched with citric acid solution (5%, 30 mL) then warmed to room temperature and extracted with ethyl acetate. The combined extracts were dried, filtered and concentrated to give the intermediate acid compound as a yellow oil. To a solution of intermediate acid in MeOH (30 mL) and diethylether (14 mL) was added trimethylsilyldiazomethane (2M in diethylether, 12 mL, 24 mmol) under ice cooling. Then the reaction mixture was quenched by addition of acetic acid (conc., 0.7 mL), evaporated and extracted with ethyl acetate. The combined extracts were washed with NaOH (2 N), water, dried over sodium sulfate, filtered and concentrated. Purification by chromatography (silica, 0 to 4% methanol in dichloromethane) afforded the title compound (1.51 g, 63%) as a yellow oil. MS: m/e=323.4 [M+H]$^+$.

b) 2-[2-(3-Butyl-5-methyl-isoxazol-4-yl)-ethyl]-4-methyl-thiazole-5-carboxylic acid (2-hydroxy-1-hydroxymethyl-ethyl)-amide To a stirred solution of 2-[2-(3-butyl-5-methyl-isoxazol-4-yl)-ethyl]-4-methyl-thiazole-5-carboxylic acid methyl ester (100 mg, 0.31 mmol) in toluene (1.0 mL) was added 2-amino-1,3-propandiol (57 mg, 0.62 mmol) and TBD (13 mg, 0.09 mmol). After 15 h the reaction mixture was concentrated in vacuo then purified by chromatography (silica, 0 to 7.5% methanol in dichloromethane) to give the title compound (65 mg, 55%) as an off white oil.

MS: m/e=382.3 [M+H]$^+$.

Example 54

2-[2-(3-Butyl-5-methyl-isoxazol-4-yl)-ethyl]-4-methyl-thiazole-5-carboxylic acid ((S)-2-hydroxy-1-methyl-ethyl)-amide

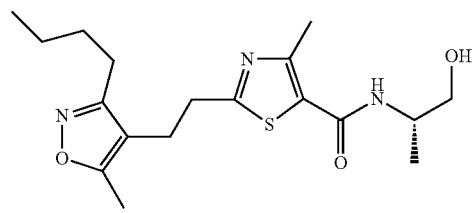

As described for example 53, 2-[2-(3-butyl-5-methyl-isoxazol-4-yl)-ethyl]-4-methyl-thiazole-5-carboxylic acid methyl ester (100 mg, 0.31 mmol) was converted, using L-alaninol instead of 2-amino-1,3-propandiol, to the title compound (80 mg, 71%) which was obtained as an off white oil. MS: m/e=366.3 [M+H]$^+$.

Example 55

2-[2-(3-Butyl-5-methyl-isoxazol-4-yl)-ethyl]-4-methyl-thiazole-5-carboxylic acid ((R)-2-hydroxy-1-methyl-ethyl)-amide

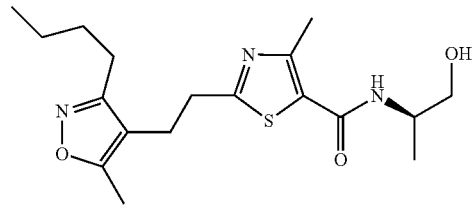

As described for example 53, 2-[2-(3-butyl-5-methyl-isoxazol-4-yl)-ethyl]-4-methyl-thiazole-5-carboxylic acid methyl ester (100 mg, 0.31 mmol) was converted, using D-alaninol instead of 2-amino-1,3-propandiol, to the title compound (85 mg, 75%) which was obtained as an off white oil. MS: m/e=366.0 [M+H]$^+$.

Example 56

2-[2-(3-Butyl-5-methyl-isoxazol-4-yl)-ethyl]-4-methyl-thiazole-5-carboxylic acid (2-hydroxy-propyl)-amide

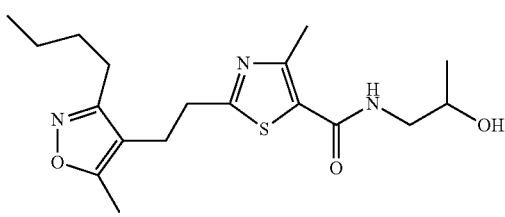

As described for example 53, 2-[2-(3-butyl-5-methyl-isoxazol-4-yl)-ethyl]-4-methyl-thiazole-5-carboxylic acid methyl ester (100 mg, 0.31 mmol) was converted, using rac-1-amino-2-propanol instead of 2-amino-1,3-propandiol, to the title compound (65 mg, 49%) which was obtained as an off white oil. MS: m/e=366.1 [M+H]⁺.

Example 57

2-[2-(3-Butyl-5-methyl-isoxazol-4-yl)-ethyl]-thiazole-5-carboxylic acid isopropylamide

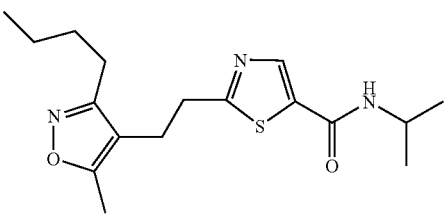

a) 2-[2-(3-Butyl-5-methyl-isoxazol-4-yl)-ethyl]-thiazole-5-carboxylic acid methyl ester To a stirred solution of 2-methyl-thiazole-5-carboxylic acid (286 mg, 2.0 mmol) in THF (14 mL) at −72° C. and under argon was added n-butyllithium (2.50 mL of a 1.6M solution in hexane, 4.0 mmol) dropwise. After 2 h, a solution of 3-butyl-4-chloromethyl-5-methyl-isoxazole (375 mg, 2.0 mmol) in THF (6 mL) was added dropwise. After 2.5 h the reaction mixture was quenched with 10% aqueous citric acid (10 mL) then warmed to room temperature. The reaction mixture was extracted with ethyl acetate then the combined extracts were dried, filtered and concentrated. The resultant oil was dissolved in methanol (15 mL) and ether (7 mL) then (trimethylsilyl)diazomethane (3 mL of a 2M solution in ether, 6.0 mmol) was added dropwise. After 30 min, further (trimethylsilyl)diazomethane (3 mL of a 2M solution in ether, 6.0 mmol) was added. After 15 h, the reaction mixture was quenched with acetic acid (3 drops) then was concentrated and purified by chromatography (silica, 0 to 75% ethyl acetate in heptane) to give the title compound (360 mg, 58%) was a light brown oil. MS: m/e=309.2 [M+H]⁺.

b) 2-[2-(3-Butyl-5-methyl-isoxazol-4-yl)-ethyl]-thiazole-5-carboxylic acid isopropylamide To a stirred solution of isopropylamine (130 mg, 2.2 mmol) in dioxane (3 mL) under argon and at room temperature was added trimethylaluminium (0.65 mL of a 2M solution in toluene, 1.3 mmol). After 1 h, a solution of 2-[2-(3-butyl-5-methyl-isoxazol-4-yl)-ethyl]-thiazole-5-carboxylic acid methyl ester (170 mg, 0.55 mmol) in dioxane (3 mL) was added and the reaction mixture heated at 90° C. overnight. The reaction mixture was then cooled, quenched with ice water and extracted with dichloromethane. The combined extracts were washed with Seignette's salt solution then dried, filtered, and concentrated. Purification by chromatography (silica, 0 to 6% methanol in dichloromethane then heptane:ethyl acetate=100:0 to 1:4) gave the title compound (30 mg, 16%) as a white solid. MS: m/e=336.5 [M+H]⁺.

Example 58

2-[2-(3-Butyl-5-methyl-isoxazol-4-yl)-ethyl]-thiazole-5-carboxylic acid (2-hydroxy-1-methyl-ethyl)-amide

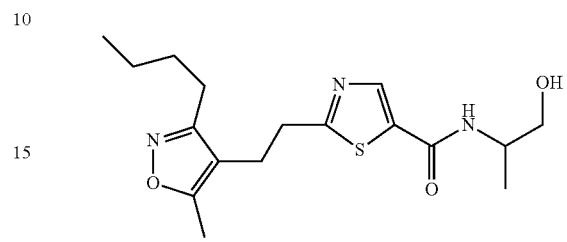

To a stirred solution of 2-[2-(3-butyl-5-methyl-isoxazol-4-yl)-ethyl]-thiazole-5-carboxylic acid methyl ester (170 mg, 0.55 mmol) in toluene (0.5 mL) was added rac-2-amino-1-propanol (83 mg, 1.1 mmol) and TBD (23 mg, 0.017 mmol). After 15 h the reaction mixture was concentrated in vacuo then purified by chromatography (silica, 0 to 7% methanol in dichloromethane) to give the title compound (85 mg, 44%) as a pale yellow oil.
MS: m/e=352.4 [M+H]⁺.

Example 59

2-[2-(3-Butyl-5-methyl-isoxazol-4-yl)-ethyl]-thiazole-5-carboxylic acid (tetrahydro-pyran-4-yl)-amide

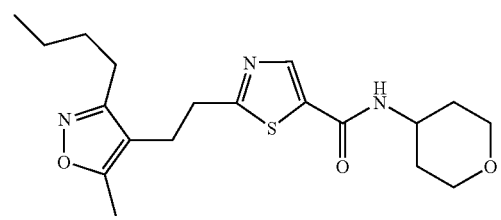

As described for example 57b, 2-[2-(3-butyl-5-methyl-isoxazol-4-yl)-ethyl]-thiazole-5-carboxylic acid methyl ester (90 mg, 0.29 mmol) was converted, using 4-aminotetrahydropyran instead of isopropylamine, to the title compound (50 mg, 76%) which was obtained as a light yellow solid. MS: m/e=378.4 [M+H]⁺.

Example 60

2-[2-(3-Butyl-5-methyl-isoxazol-4-yl)-ethyl]-thiazole-5-carboxylic acid (tetrahydro-furan-3-yl)-amide

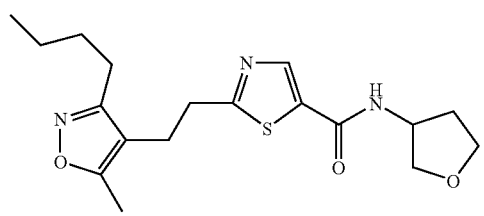

As described for example 57b, 2-[2-(3-butyl-5-methyl-isoxazol-4-yl)-ethyl]-thiazole-5-carboxylic acid methyl ester (90 mg, 0.29 mmol) was converted, using tetrahydrofuran-3-amine instead of isopropylamine, to the title compound (45 mg, 71%) which was obtained as a light yellow oil. MS: m/e=364.3 [M+H]+.

Example 61

2-[2-(3-Butyl-5-methyl-isoxazol-4-yl)-ethyl]-thiazole-5-carboxylic acid ((S)-2-hydroxy-1-methyl-ethyl)-amide

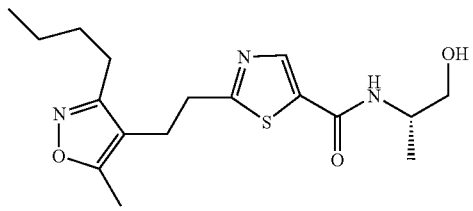

As described for example 58, 2-[2-(3-butyl-5-methyl-isoxazol-4-yl)-ethyl]-thiazole-5-carboxylic acid methyl ester (90 mg, 0.29 mmol) was converted, using L-alaninol instead of rac-2-amino-1-propanol, to the title compound (50 mg, 81%) which was obtained as a colourless oil. MS: m/e=352.4 [M+H]+.

Example 62

2-[2-(3-Butyl-5-methyl-isoxazol-4-yl)-ethyl]-thiazole-5-carboxylic acid (2-hydroxy-propyl)-amide

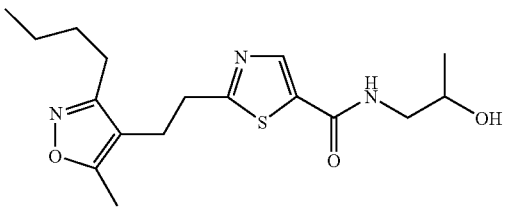

As described for example 58, 2-[2-(3-butyl-5-methyl-isoxazol-4-yl)-ethyl]-thiazole-5-carboxylic acid methyl ester (90 mg, 0.29 mmol) was converted, using rac-1-amino-2-propanol instead of rac-2-amino-1-propanol, to the title compound (50 mg, 69%) which was obtained as a light yellow oil. MS: m/e=352.4 [M+H]+.

Example 63

2-[(E)-2-(5-Methyl-3-phenyl-isoxazol-4-yl)-vinyl]-thiazole-5-carboxylic acid (tetra-hydro-pyran-4-yl)-amide

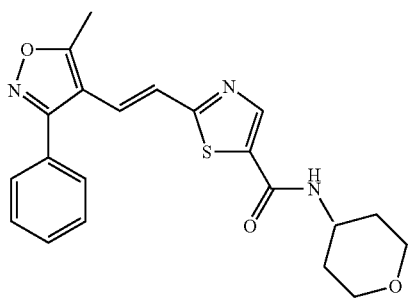

a) 2-[(E)-2-(5-Methyl-3-phenyl-isoxazol-4-yl)-vinyl]-thiazole-5-carboxylic acid ethyl ester 2-Methyl-thiazole-5-carboxylic acid ethyl ester (547 mg, 2.92 mmol) was dissolved in acetic anhydride (0.15 mL, 15.5 mmol) and acetic acid (0.04 mL, 2.54 mmol) then 5-methyl-3-phenyl-4-isoxazolecarbaldehyde (500 mg, 2.92 mmol) was added and the reaction mixture warmed to 120° C. After 6 days, the reaction mixture was cooled to room temperature then diluted with water and extracted with ethyl acetate. The combined organic extracts were dried, filtered and concentrated then purified by chromatography (silica, 0 to 30% ethyl acetate in heptane) to give the title compound (191 mg, 19%) as an off-white solid after trituration with isopropylether. MS: m/e=341.3 [M+H]+.

b) 2-[(E)-2-(5-Methyl-3-phenyl-isoxazol-4-yl)-vinyl]-thiazole-5-carboxylic acid(tetra-hydro-pyran-4-yl)-amide To a stirred solution of 4-aminotetrahydropyran (123 mg, 1.22 mmol) in dioxane (3 mL) under argon and at room temperature was added trimethylaluminium (0.6 mL of a 2M solution in toluene, 1.2 mmol). After 1 h, a solution of 2-[(E)-2-(5-methyl-3-phenyl-isoxazol-4-yl)-vinyl]-thiazole-5-carboxylic acid ethyl ester (50 mg, 0.15 mmol) in dioxane (3 mL) was added and the reaction mixture heated at 90° C. for 3 h. The reaction mixture was then cooled, quenched with ice water and extracted with dichloromethane. The combined extracts were washed with Seignette's salt solution then dried, filtered, and concentrated. Purification by chromatography (silica, 0 to 2.5% methanol in dichloromethane) gave the title compound (34 mg, 59%) as a white solid. MS: m/e=396.3 [M+H]+.

Example 64

(S)-2-[(E)-2-(5-Methyl-3-phenyl-isoxazol-4-yl)-vinyl]-thiazole-5-carboxylic acid (tetra-hydro-furan-3-yl)-amide

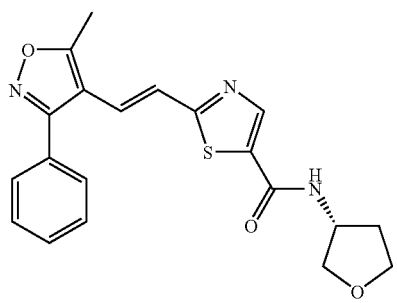

As described for example 63b, 2-[(E)-2-(5-methyl-3-phenyl-isoxazol-4-yl)-vinyl]-thiazole-5-carboxylic acid ethyl ester (50 mg, 0.15 mmol) was converted, using (S)-tetrahydrofuran-3-amine HCl instead of 4-aminotetrahydropyran, to the title compound (50 mg, 89%) which was obtained as a white solid. MS: m/e=382.3 [M+H]+.

Example 65

2-[(E)-2-(5-Methyl-3-phenyl-isoxazol-4-yl)-vinyl]-thiazole-5-carboxylic acid isoprop-ylamide

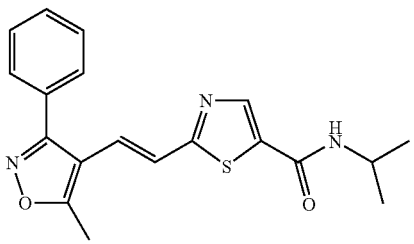

As described for example 63b, 2-[(E)-2-(5-methyl-3-phenyl-isoxazol-4-yl)-vinyl]-thiazole-5-carboxylic acid ethyl ester (50 mg, 0.15 mmol) was converted, using isopropylamine instead of 4-aminotetrahydropyran, to the title compound (37 mg, 71%) which was obtained as a white solid. MS: m/e=354.4 [M+H]$^+$.

Example 66

2-[(E)-2-(5-Methyl-3-phenyl-isoxazol-4-yl)-vinyl]-thiazole-5-carboxylic acid (2-hydroxy-1-methyl-ethyl)-amide

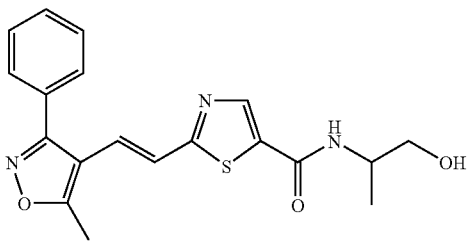

To a stirred solution of 2-[(E)-2-(5-methyl-3-phenyl-isoxazol-4-yl)-vinyl]-thiazole-5-carboxylic acid ethyl ester (30 mg, 0.09 mmol) in toluene (0.5 mL) was added rac-2-amino-1-propanol (9 mg, 0.12 mmol) and TBD (4 mg, 0.03 mmol). After 15 h, the reaction mixture was concentrated in vacuo then purified by chromatography (silica, 0 to 3% methanol in dichloromethane) to give the title compound (26 mg, 80%) as a white solid. MS: m/e=370.0 [M+H]$^+$.

Example 67

2-[(E)-2-(5-Methyl-3-phenyl-isoxazol-4-yl)-vinyl]-thiazole-5-carboxylic acid (2-hydroxy-ethyl)-amide

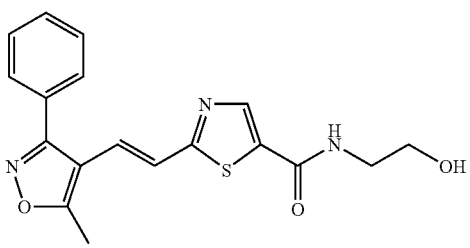

As described for example 66, 4-methyl-2-[(E)-2-(5-methyl-3-phenyl-isoxazol-4-yl)-vinyl]-thiazole-5-carboxylic acid methyl ester (55 mg, 0.17 mmol) was converted, using ethanolamine instead of rac-2-amino-1-propanol, to the title compound (34 mg, 63%) which was obtained as a light yellow solid. MS: m/e=356.2 [M+H]$^+$.

Example 68

4-Methyl-2-[(E)-2-(5-methyl-3-phenyl-isoxazol-4-yl)-vinyl]-thiazole-5-carboxylic acid isopropylamide

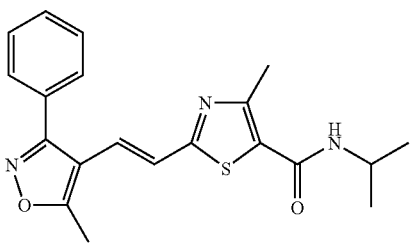

a) 2-[2-Hydroxy-2-(5-methyl-3-phenyl-isoxazol-4-yl)-ethyl]-4-methyl-thiazole-5-carbox-ylic acid methyl ester To a stirred solution of 2,4-dimethyl-thiazole-5-carboxylic acid (0.84 g, 5.34 mmol) in THF (50 mL) at −78° C. and under argon was added n-butyllithium (7.63 mL of a 1.40M solution in hexane, 10.7 mmol) dropwise. After 1 h, a solution of 5-methyl-3-phenyl-isoxazole-4-carbaldehyde (1.0 g, 5.34 mmol) in THF (50 mL) was added dropwise. After 3 h the reaction mixture was quenched with 10% aqueous citric acid (50 mL) then warmed to room temperature. The reaction mixture was extracted with ethyl acetate then the combined extracts were dried, filtered and concentrated. The resultant oil was redissolved in ethyl acetate, washed with water then dried, filtered and concentrated in vacuo. The resultant residue was dissolved in methanol (40 mL) and ether (20 mL) then (trimethylsilyl)diazomethane (4.0 mL of a 2M solution in ether, 8.0 mmol) was added dropwise. After 30 min, further (trimethylsilyl)diazomethane (4.0 mL of a 2M solution in ether, 8.0 mmol) was added. After 15 h, the reaction mixture was quenched with acetic acid (3 drops) then was concentrated and the residue redissolved in ethyl acetate and washed with NaOH (2 N). The organic phase was dried, filtered and concentrated then purified by chromatography (silica, 10 to 40% ethyl acetate in heptane) to give the title compound (500 mg, 26%) as a yellow foam. MS: m/e=359.0 [M]$^+$.

b) 4-Methyl-2-[(E)-2-(5-methyl-3-phenyl-isoxazol-4-yl)-vinyl]-thiazole-5-carboxylic acid methyl ester Concentrated sulfuric acid (5 mL) was added to 2-[2-hydroxy-2-(5-methyl-3-phenyl-isoxazol-4-yl)-ethyl]-4-methyl-thiazole-5-carboxylic acid methyl ester (200 mg, 0.56 mmol) then the mixture was heated at 90° C. for 10 min. The solution was carefully dropped into saturated sodium bicarbonate solution (100 mL) then extracted with ether. The combined organic extracts were dried, filtered and concentrated, to give the title compound (160 mg, 84%) as a yellow oil which solidified on standing to a yellow solid. This material was used directly without further purification. MS: m/e=341.1 [M+H]$^+$.

c) 4-Methyl-2-[(E)-2-(5-methyl-3-phenyl-isoxazol-4-yl)-vinyl]-thiazole-5-carboxylic acid isopropylamide To a stirred solution of isopropylamine (56 mg, 0.95 mmol) in dioxane (2 mL) under argon and at room temperature was added trimethylaluminium (0.47 mL of a 2M solution in toluene, 0.94 mmol). After 1 h, a solution of 4-methyl-2-[(E)-2-(5-methyl-3-phenyl-isoxazol-4-yl)-vinyl]-thiazole-5-carboxylic acid methyl ester (80 mg, 0.24 mmol) in dioxane (2 mL) was added and the reaction mixture warmed to 90° C. After 24 h, the reaction mixture was cooled, quenched with ice and Seignettes's salt solution, then extracted with ethyl acetate. The combined organic extracts were dried, filtered and concentrated. Purification by chromatography (silica, 10 to 80% ethyl acetate in heptane) gave the title compound (40 mg, 46%) as an off white solid. MS: m/e=368.1 [M+H]$^+$.

Example 69

4-Methyl-2-[(E)-2-(5-methyl-3-phenyl-isoxazol-4-yl)-vinyl]-thiazole-5-carboxylic acid (tetrahydrofuran-3-yl)-amide

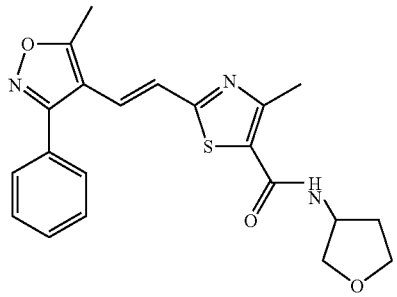

As described for example 68c, 4-methyl-2-[(E)-2-(5-methyl-3-phenyl-isoxazol-4-yl)-vinyl]-thiazole-5-carboxylic acid methyl ester (80 mg, 0.24 mmol) was converted, using 3-amino-tetrahydrofuran instead of isopropylamine, to the title compound (40 mg, 43%) which was obtained as a light yellow solid. MS: m/e=396.3 [M+H]$^+$.

Example 70

4-Methyl-2-[(E)-2-(5-methyl-3-phenyl-isoxazol-4-yl)-vinyl]-thiazole-5-carboxylic acid (2-hydroxy-ethyl)-amide

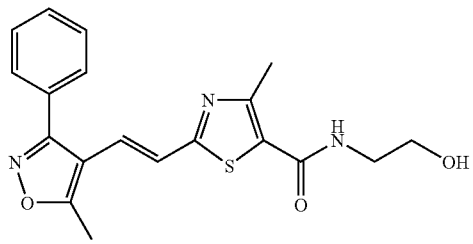

To a stirred solution of 4-methyl-2-[(E)-2-(5-methyl-3-phenyl-isoxazol-4-yl)-vinyl]-thiazole-5-carboxylic acid methyl ester (70 mg, 0.21 mmol) in toluene (0.5 mL) was added ethanolamine (15 mg, 0.25 mmol) and TBD (18 mg, 0.13 mmol). After 24 h the reaction mixture was diluted with brine and extracted with ethyl acetate. The combined extracts were dried, filtered and concentrated in vacuo, then purified by chromatography (silica, 0 to 10% methanol in dichloromethane) to give the title compound (48 mg, 60%) as a pale yellow oil. MS: m/e=370.1 [M+H]$^+$.

Example 71

2-{(E)-2-[3-(5-Fluoro-pyridin-2-yl)-5-methyl-isoxazol-4-yl]-vinyl}-4-methyl-thiazole-5-carboxylic acid isopropylamide

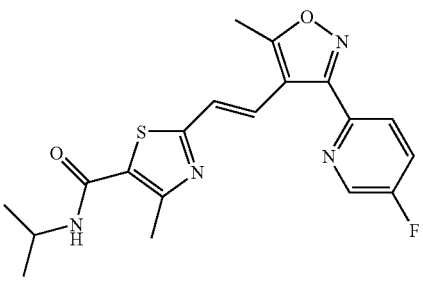

ai) 3-(5-Fluoro-pyridin-2-yl)-5-methyl-isoxazole-4-carbaldehyde

To a solution of [3-(5-fluoro-pyridin-2-yl)-5-methyl-isoxazol-4-yl]-methanol (1.9 g, 9.13 mmol) in DCM (38 mL) was added a suspension of DMP (4.65 g, 10.96 mmol) in DCM (30 mL) portionwise and under argon at room temperature and then the mixture was cooled to 0° C. and the resulting mixture warmed up to room temperature overnight. The mixture was then poured carefully into stirred saturated sodium hydrogen carbonate solution and the aqueous layer extracted with DCM. The combined organic layers were then washed with brine, dried over sodium sulfate and evaporated. Purification by chromatography (silica, 0 to 50% ethyl acetate in heptane) gave the title compound (1.7 g, 90%) as a white solid. MS: m/e=207.0 [M+H]$^+$. Alternatively aii) 3-(5-Fluoro-pyridin-2-yl)-5-methyl-isoxazole-4-carbaldehyde To a solution of [3-(5-fluoro-pyridin-2-yl)-5-methyl-isoxazol-4-yl]-methanol (2.10 g, 10.1 mmol) in DCM (240 mL) was added manganese(IV) oxide (activated 85%, 20.63 g, 201 mmol) and the reaction mixture was stirred vigorously at room temperature for 3 days. The reaction mixture was filtered through dicalite and then fresh manganese(IV) oxide (activated 85%, 20.63 g, 201 mmol) was added and the reaction mixture stirred vigorously at room temperature for another 4 days. The reaction mixture was filtered through dicalite and evaporated. The combined DCM extracts were then dried over sodium sulfate, filtered and evaporated. Purification by chromatography (silica, 0 to 50% ethyl acetate in heptane) gave the title compound (845 mg, 40%) as a white solid. MS: m/e=207.0 [M+H]$^+$.

b) 2-{2-[3-(5-Fluoro-pyridin-2-yl)-5-methyl-isoxazol-4-yl]-2-hydroxy-ethyl}-4-methyl-thiazole-5-carboxylic acid To a stirred solution of 2,4-dimethyl-thiazole-5-carboxylic acid (650 mg, 7.0 mmol) in THF (33 mL) at −70° C. and under argon was added BuLi (1.6M in hexanes, 4.94 mL, 7.9 mmol) dropwise. After 2 h a solution of 3-(5-fluoro-pyridin-2-yl)-5-methyl-isoxazole-4-carbaldehyde (814 mg, 3.95 mmol) in THF (12 mL) was added dropwise. After 2 h the reaction mixture was quenched with citric acid solution (5%, 25 mL) then warmed to room temperature and extracted with ethyl acetate. The combined extracts were washed with brine, water, dried over sodium sulfate, filtered and concentrated. Purification by recrystallization (ethyl acetate) afforded the title compound (729 mg, 51%) as a light yellow solid. MS: m/e=362.2 [M+H]⁺.

c) 2-{(E)-2-[3-(5-Fluoro-pyridin-2-yl)-5-methyl-isoxazol-4-yl]-vinyl}-4-methyl-thiazole-5-carboxylic acid Concentrated sulfuric acid (9.3 mL) was added to 2-{2-[3-(5-fluoro-pyridin-2-yl)-5-methyl-isoxazol-4-yl]-2-hydroxy-ethyl}-4-methyl-thiazole-5-carboxylic acid (574 mg, 1.58 mmol) then the mixture was heated at 90° C. for 10 min. After cooling to room temperature the mixture was poured into ice (100 g) and the precipitate was filtered off and dried to give the title product. (471 mg, 86%) as a yellow solid. MS: m/e=344.1 [M–H]⁻.

d) 2-{(E)-2-[3-(5-Fluoro-pyridin-2-yl)-5-methyl-isoxazol-4-yl]-vinyl}-4-methyl-thiazole-5-carboxylic acid isopropylamide To a solution of 2-{(E)-2-[3-(5-fluoro-pyridin-2-yl)-5-methyl-isoxazol-4-yl]-vinyl}-4-methyl-thiazole-5-carboxylic acid (28 mg, 0.085 mmol) in DMF (0.5 mL) were added 2-(1H-benzotriazole-1-yl)-1,1,3,3-tetramethyluronium tetrafluoroborate (30 mg, 0.085 mmol), N,N-diisopropyl ethyl amine (72 μL, 0.423 mmol) and isopropylamine (8 μL, 0.40 mmol). The resulting reaction mixture was stirred for 1 h. The reaction mixture was then evaporated and purification by chromatography (silica, 0 to 100% ethyl acetate in heptane) afforded the title compound (24 mg, 74%) as a white solid after trituration from water. MS: m/e=387.2 [M+H]⁺.

Example 72

2-{(E)-2-[3-(5-Fluoro-pyridin-2-yl)-5-methyl-isoxazol-4-yl]-vinyl}-4-methyl-thiazole-5-carboxylic acid (tetrahydro-pyran-4-yl)-amide

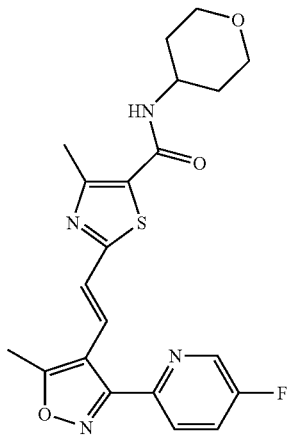

As described for example 71d, 2-{(E)-2-[3-(5-fluoro-pyridin-2-yl)-5-methyl-isoxazol-4-yl]-vinyl}-4-methyl-thiazole-5-carboxylic acid (69 mg, 0.2 mmol) was converted, using 4-aminotetrahydropyran instead of isopropylamine, to the title compound (60 mg, 70%) which was obtained as a white solid after trituration from methanol/water. MS: m/e=429.2 [M+H]⁺.

Example 73

2-{(E)-2-[3-(5-Fluoro-pyridin-2-yl)-5-methyl-isoxazol-4-yl]-vinyl}-4-methyl-thiazole-5-carboxylic acid cyclopropylamide

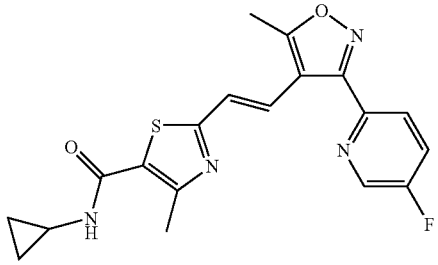

As described for example 71d, 2-{(E)-2-[3-(5-fluoro-pyridin-2-yl)-5-methyl-isoxazol-4-yl]-vinyl}-4-methyl-thiazole-5-carboxylic acid (69 mg, 0.2 mmol) was converted, using cyclopropylamine instead of isopropylamine, to the title compound (40 mg, 52%) which was obtained as a white solid after trituration from methanol/water. MS: m/e=385.1 [M+H]⁺.

Example 74

2-{(E)-2-[3-(5-Fluoro-pyridin-2-yl)-5-methyl-isoxazol-4-yl]-vinyl}-4-methyl-thiazole-5-carboxylic acid (2-hydroxy-1,1-dimethyl-ethyl)-amide

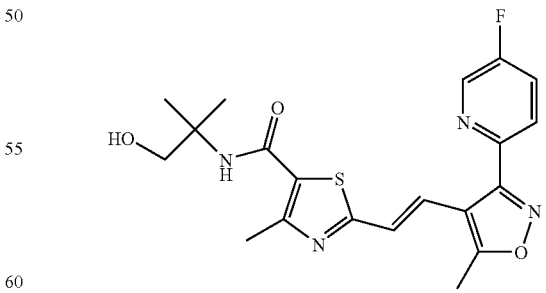

As described for example 71d, 2-{(E)-2-[3-(5-fluoro-pyridin-2-yl)-5-methyl-isoxazol-4-yl]-vinyl}-4-methyl-thiazole-5-carboxylic acid (69 mg, 0.2 mmol) was converted, using 2-amino-2-methyl-1-propanol instead of isopropylamine, to the title compound (25 mg, 30%) which was obtained as a white solid after trituration from methanol/water. MS: m/e=417.2 [M+H]$^+$.

Example 75

2-{(E)-2-[3-(5-Fluoro-pyridin-2-yl)-5-methyl-isoxazol-4-yl]-vinyl}-4-methyl-thiazole-5-carboxylic acid cyclopropylmethyl-amide

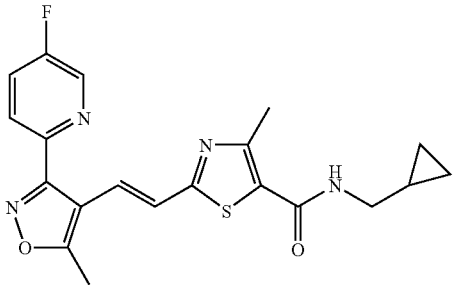

As described for example 71d, 2-{(E)-2-[3-(5-fluoro-pyridin-2-yl)-5-methyl-isoxazol-4-yl]-vinyl}-4-methyl-thiazole-5-carboxylic acid (69 mg, 0.2 mmol) was converted, using aminomethylcyclopropane instead of isopropylamine, to the title compound (53 mg, 67%) which was obtained as a white solid. MS: m/e=399.1 [M+H]$^+$.

Example 76

2-{(E)-2-[3-(5-Fluoro-pyridin-2-yl)-5-methyl-isoxazol-4-yl]-vinyl}-4-methyl-thiazole-5-carboxylic acid amide

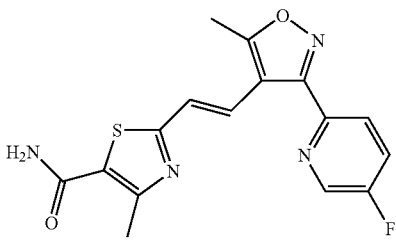

To a solution of 2-{(E)-2-[3-(5-fluoro-pyridin-2-yl)-5-methyl-isoxazol-4-yl]-vinyl}-4-methyl-thiazole-5-carboxylic acid (69 mg, 0.2 mmol) in DMF (2 mL) was added 1,1'-carbonyldiimidazole (39 mg, 0.24 mmol). The resulting reaction mixture was stirred for 1 h at 60° C. and then treated with an ammonium hydroxide solution (308 L, 2.0 mmol) and stirred for 2 h at room temperature. The reaction mixture was then evaporated. Purification by chromatography (silica, heptane:ethyl acetate=1:1 to 0:1) afforded the title compound (33 mg, 48%) as a white solid after trituration from dichloromethane. MS: m/e=345.2 [M+H]$^+$.

Example 77

2-{(E)-2-[3-(5-Fluoro-pyridin-2-yl)-5-methyl-isoxazol-4-yl]-vinyl}-thiazole-5-carboxylic acid (tetrahydro-pyran-4-yl)-amide

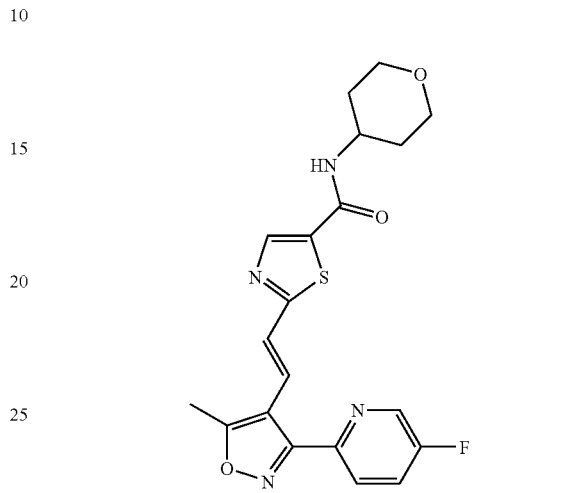

a) 2-{2-[3-(5-Fluoro-pyridin-2-yl)-5-methyl-isoxazol-4-yl]-2-hydroxy-ethyl}-thiazole-5-carboxylic acid To a stirred solution of 2-methyl-thiazole-5-carboxylic acid (1.15 g, 8.05 mmol) in THF (67 mL) at −70° C. and under argon was added BuLi (1.6M in hexanes, 10.06 mL, 16.1 mmol) dropwise. After 2 h a solution of 3-(5-fluoro-pyridin-2-yl)-5-methyl-isoxazole-4-carbaldehyde (1.66 g, 8.05 mmol) in THF (24 mL) was added dropwise. After 3 h the reaction mixture was quenched with citric acid solution (5%, 50 mL) then warmed to room temperature and extracted with ethyl acetate. The combined extracts were washed with brine, water, dried over sodium sulfate, filtered and concentrated. Purification by trituration (ethyl acetate) afforded the title compound (1.85 g, 66%) as a light yellow solid. MS: m/e=348.2 [M−H]$^-$.

b) 2-{(E)-2-[3-(5-Fluoro-pyridin-2-yl)-5-methyl-isoxazol-4-yl]-vinyl}-thiazole-5-carbox-ylic acid Concentrated sulfuric acid (29 mL) was added to 2-{2-[3-(5-fluoro-pyridin-2-yl)-5-methyl-isoxazol-4-yl]-2-hydroxy-ethyl}-thiazole-5-carboxylic acid (1.71 g, 4.9 mmol) then the mixture was heated at 90° C. for 10 min. After cooling to room temperature the mixture was poured into ice (200 g) and the precipitate was filtered off and dried to give the title product (1.44 g, 89%) as a yellow solid. MS: m/e=330.0 [M−H]$^-$.

c) 2-{(E)-2-[3-(5-Fluoro-pyridin-2-yl)-5-methyl-isoxazol-4-yl]-vinyl}-thiazole-5-carboxylic acid (tetrahydro-pyran-4-yl)-amide To a solution of 2-{(E)-2-[3-(5-fluoro-pyridin-2-yl)-5-methyl-isoxazol-4-yl]-vinyl}-thiazole-5-carboxylic acid (83 mg, 0.25 mmol) in DMF (1.5 mL) were added 2-(1H-benzotriazole-1-yl)-1,1,3,3-tetramethyluronium tetrafluoroborate (88 mg, 0.28 mmol), N,N-diisopropyl ethyl amine (214 μL, 1.25 mmol) and 4-aminotetrahydropyran (28 mg, 0.28 mmol). The resulting reaction mixture was stirred for 1 h. The reaction mixture was then evaporated and purification by chromatography (silica, 50 to 100% ethyl acetate in heptane) afforded the title compound (68 mg, 66%) as a white solid. MS: m/e=415.3 [M+H]$^+$.

Example 78

2-{(E)-2-[3-(5-Fluoro-pyridin-2-yl)-5-methyl-isoxazol-4-yl}-vinyl]-thiazole-5-carboxylic acid isopropylamide

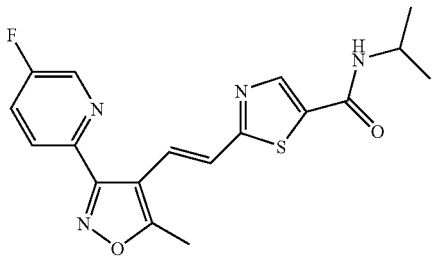

As described for example 77c, 2-{(E)-2-[3-(5-fluoro-pyridin-2-yl)-5-methyl-isoxazol-4-yl]-vinyl}-thiazole-5-carboxylic acid (83 mg, 0.25 mmol) was converted, using isopropylamine instead of 4-aminotetrahydropyran, to the title compound (55 mg, 59%) which was obtained as an off white solid after recrystallization from heptane/ethyl acetate. MS: m/e=373.1 [M+H]$^+$.

Example 79

2-{(E)-2-[3-(5-Fluoro-pyridin-2-yl)-5-methyl-isoxazol-4-yl]-vinyl}-thiazole-5-carboxylic acid cyclopropylamide

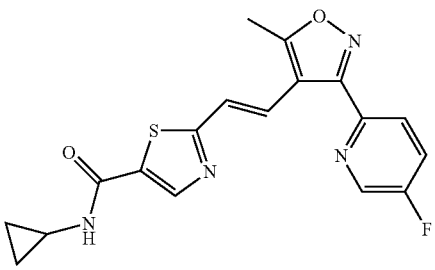

As described for example 77c, 2-{(E)-2-[3-(5-fluoro-pyridin-2-yl)-5-methyl-isoxazol-4-yl]-vinyl}-thiazole-5-carboxylic acid (83 mg, 0.25 mmol) was converted, using cyclopropylamine instead of 4-aminotetrahydropyran, to the title compound (40 mg, 43%) which was obtained as a light yellow solid after recrystallization from heptane/ethyl acetate. MS: m/e=371.1 [M+H]$^+$.

Example 80

2-{(E)-2-[3-(5-Fluoro-pyridin-2-yl)-5-methyl-isoxazol-4-yl]-vinyl}-thiazole-5-carboxylic acid (2-hydroxy-1,1-dimethyl-ethyl)-amide

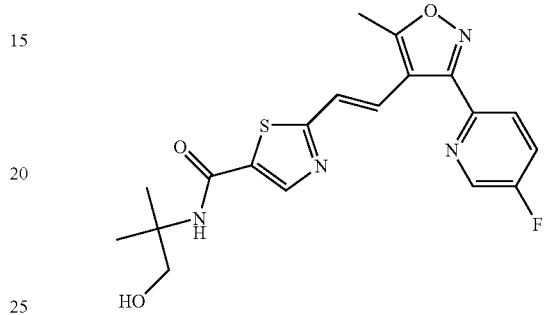

As described for example 77c, 2-{(E)-2-[3-(5-fluoro-pyridin-2-yl)-5-methyl-isoxazol-4-yl]-vinyl}-thiazole-5-carboxylic acid (83 mg, 0.25 mmol) was converted, using 2-amino-2-methyl-1-propanol instead of 4-aminotetrahydropyran, to the title compound (46 mg, 46%) which was obtained as an off white solid after recrystallization from heptane/ethyl acetate. MS: m/e=403.3 [M+H]$^+$.

Example 81

2-{(E)-2-[3-(5-Fluoro-pyridin-2-yl)-5-methyl-isoxazol-4-yl]-vinyl}-thiazole-5-carboxylic acid amide

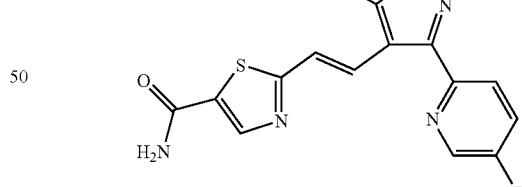

To a solution of 2-{(E)-2-[3-(5-fluoro-pyridin-2-yl)-5-methyl-isoxazol-4-yl]-vinyl}-thiazole-5-carboxylic acid (83 mg, 0.25 mmol) in DMF (2.5 mL) was added 1,1'-carbonyldiimidazole (49 mg, 0.3 mmol). The resulting reaction mixture was stirred for 1 h at 60° C. and then treated with an ammonium hydroxide solution (25%, 385 μL, 2.5 mmol) and stirred for 2 h at room temperature. The reaction mixture was then evaporated. Purification by trituration from water/ methanol afforded the title compound (64 mg, 77%) as an off white solid after. MS: m/e=331.0 [M+H]⁺.

Example 82

2-{(E)-2-[3-(5-Fluoro-pyridin-2-yl)-5-methyl-isoxazol-4-yl]-vinyl}-thiazole-5-carboxylic acid cyclopropylmethyl-amide

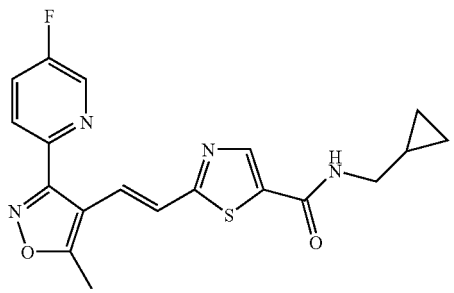

As described for example 77c, 2-{(E)-2-[3-(5-fluoro-pyridin-2-yl)-5-methyl-isoxazol-4-yl]-vinyl}-thiazole-5-carboxylic acid (83 mg, 0.25 mmol) was converted, using aminomethylcyclopropane instead of 4-aminotetrahydropyran, to the title compound (56 mg, 58%) which was obtained as a light yellow solid after purification by chromatography (silica, 0 to 100% ethyl acetate in heptane). MS: m/e=385.2 [M+H]⁺.

Example 83

(1,1-Dioxothiomorpholin-4-yl)-(2-{(E)-2-[3-(5-fluoro-pyridin-2-yl)-5-methyl-isoxazol-4-yl]-vinyl}-thiazol-5-yl)-methanone

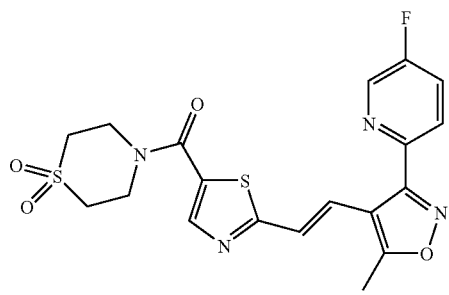

As described for example 77c, 2-{(E)-2-[3-(5-fluoro-pyridin-2-yl)-5-methyl-isoxazol-4-yl]-vinyl}-thiazole-5-carboxylic acid (83 mg, 0.25 mmol) was converted, using thiomorpholine 1,1-dioxide instead of 4-aminotetrahydropyran, to the title compound (94 mg, 84%) which was obtained as a light yellow solid after purification by chromatography (silica, 0 to 100% ethyl acetate in heptane). MS: m/e=449.1 [M+H]⁺.

Example 84

2-{(E)-2-[3-(5-Fluoro-pyridin-2-yl)-5-methyl-isoxazol-4-yl]-vinyl}-thiazole-5-carboxylic acid (2,2,2-trifluoro-ethyl)-amide

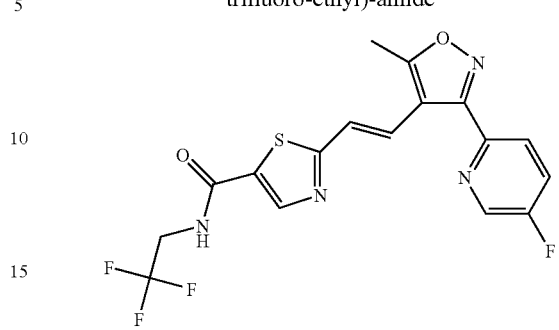

As described for example 77c, 2-{(E)-2-[3-(5-fluoro-pyridin-2-yl)-5-methyl-isoxazol-4-yl]-vinyl}-thiazole-5-carboxylic acid (83 mg, 0.25 mmol) was converted, using 2,2,2-trifluoroethylamine instead of 4-aminotetrahydropyran, to the title compound (87 mg, 84%) which was obtained as a yellow solid after purification by chromatography (silica, 0 to 100% ethyl acetate in heptane). MS: m/e=413.1 [M+H]⁺.

Example 85

2-{(E)-2-[3-(5-Fluoro-pyridin-2-yl)-5-methyl-isoxazol-4-yl]-vinyl}-thiazole-5-carboxylic acid (2-hydroxy-ethyl)-amide

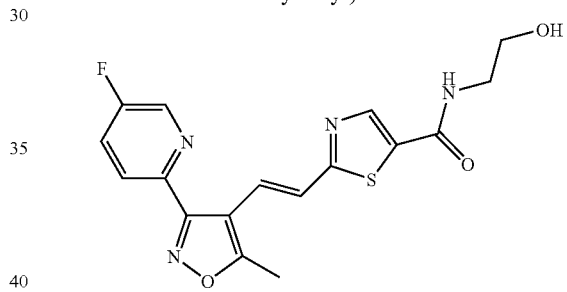

As described for example 77c, 2-{(E)-2-[3-(5-fluoro-pyridin-2-yl)-5-methyl-isoxazol-4-yl]-vinyl}-thiazole-5-carboxylic acid (83 mg, 0.25 mmol) was converted, using ethanolamine instead of 4-aminotetrahydropyran, to the title compound (43 mg, 46%) which was obtained as an off white solid after purification by chromatography (silica, 0 to 100% ethyl acetate in heptane) and trituration from methanol. MS: m/e=375.2 [M+H]⁺.

Example 86

(2-{(E)-2-[3-(5-Fluoro-pyridin-2-yl)-5-methyl-isoxazol-4-yl]-vinyl}-thiazol-5-yl)-morpholin-4-yl-methanone

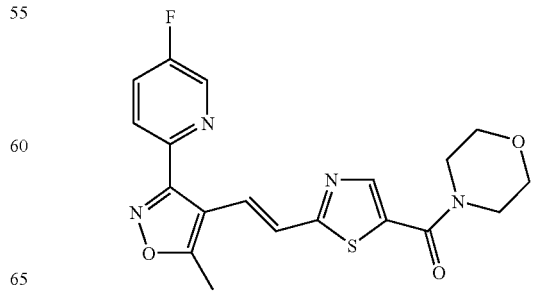

As described for example 77c, 2-{(E)-2-[3-(5-fluoro-pyridin-2-yl)-5-methyl-isoxazol-4-yl]-vinyl}-thiazole-5-carboxylic acid (83 mg, 0.25 mmol) was converted, using morpholine instead of 4-aminotetrahydropyran, to the title compound (83 mg, 83%) which was obtained as a yellow solid after purification by chromatography (silica, 0 to 100% ethyl acetate in heptane). MS: m/e=401.2 [M+H]+.

Example 87

2-{(E)-2-[3-(5-Fluoro-pyridin-2-yl)-5-methyl-isoxazol-4-yl]-vinyl}-thiazole-5-carboxylic acid ethylamide

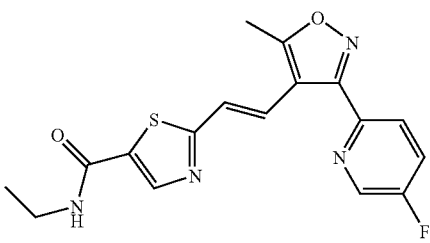

As described for example 77c, 2-{(E)-2-[3-(5-fluoro-pyridin-2-yl)-5-methyl-isoxazol-4-yl]-vinyl}-thiazole-5-carboxylic acid (83 mg, 0.25 mmol) was converted, using ethylamine (2M solution in THF) instead of 4-aminotetrahydropyran, to the title compound (70 mg, 78%) which was obtained as a yellow solid after purification by chromatography (silica, 0 to 100% ethyl acetate in heptane). MS: m/e=359.1 [M+H]+.

Example 88

2-{(E)-2-[3-(5-Fluoro-pyridin-2-yl)-5-methyl-isoxazol-4-yl]-vinyl}-thiazole-5-carboxylic acid methylamide

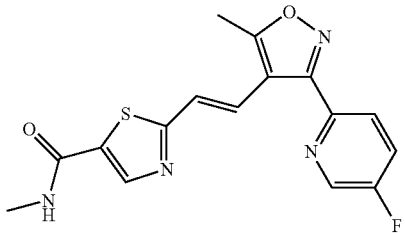

As described for example 77c, 2-{(E)-2-[3-(5-fluoro-pyridin-2-yl)-5-methyl-isoxazol-4-yl]-vinyl}-thiazole-5-carboxylic acid (83 mg, 0.25 mmol) was converted, using methylamine (2M solution in THF) instead of 4-aminotetrahydropyran, to the title compound (66 mg, 77%) which was obtained as a yellow solid after purification by chromatography (silica, 0 to 100% ethyl acetate in heptane). MS: m/e=345.0 [M+H]+.

Example 89

(2-{(E)-2-[3-(5-Fluoro-pyridin-2-yl)-5-methyl-isoxazol-4-yl]-vinyl}-thiazol-5-yl)-thiomorpholin-4-yl-methanone

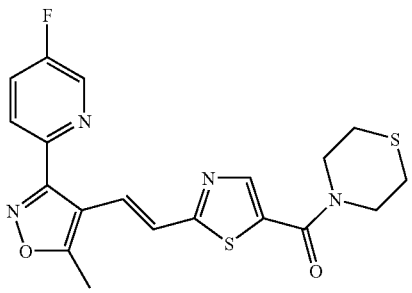

As described for example 77c, 2-{(E)-2-[3-(5-fluoro-pyridin-2-yl)-5-methyl-isoxazol-4-yl]-vinyl}-thiazole-5-carboxylic acid (83 mg, 0.25 mmol) was converted, using thiomorpholine instead of 4-aminotetrahydropyran, to the title compound (61 mg, 59%) which was obtained as a yellow solid after purification by chromatography (silica, 0 to 100% ethyl acetate in heptane) and trituration from diethyl ether. MS: m/e=417.2 [M+H]+.

Example 90

2-{(E)-2-[3-(5-Fluoro-pyridin-2-yl)-isoxazol-4-yl]-vinyl}-4-methyl-thiazole-5-carboxylic acid (tetrahydro-pyran-4-yl)-amide

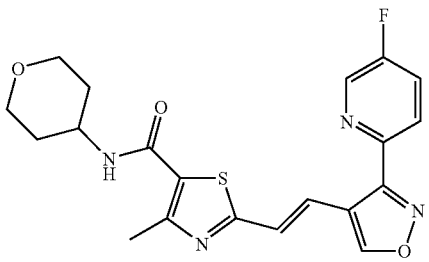

a) 5-Fluoro-pyridine-2-carbaldehyde oxime

To a solution of 5-fluoro-2-formylpyridine (5.0 g, 41 mmol) and hydroxylamine hydrochloride (3.06 g, 44 mmol) in ethanol (3.2 mL) and water (9.6 mL) was added ice (18.6 g). Then a solution of NaOH (4.0 g, 100 mmol) in water (4.6 mL) was added dropwise over 10 min keeping the temperature between −5° C. and 5° C. The reaction mixture was then stirred at room temperature for 30 min. Then HCl (4 N) was added to acidify the mixture and the resulting precipitate was filtered off and washed with water to afford the title compound (4.41 g, 79%) as a light brown solid. MS: m/e=141.0 [M+H]+.

b) 3-(5-Fluoro-pyridin-2-yl)-isoxazole-4-carboxylic acid ethyl ester

To a solution of N-chlorosuccinimide (17.34 g, 130 mmol) in DMF (128 mL) was added 5-fluoro-pyridine-2-carbaldehyde oxime (18.2 g, 130 mmol) portionwise over 2 h at room temperature and as the reaction warmed up to 60° C. the mixture was cooled back to room temperature with an ice-water bath and the resulting mixture was then stirred for 64 h at room temperature. To this solution was then added ethyl 3-(N,N-dimethylamino)acrylate (18.6 g, 130 mmol) and triethylamine (36.2 mL, 260 mmol) in chloroform (64 mL) and the resulting mixture was then stirred for 1 h at room temperature and poured onto a mixture of ice water and HCl (4 N, 1 L) and extracted with ethylacetate. The organic extract was then washed with water, saturated aqueous sodium hydrogen carbonate solution, brine, dried with sodium sulfate, filtered and evaporated. Purification by chromatography (silica, heptane:ethylacetate=100:0 to 1:1) afforded the title product (21.96 g, 72%) which was obtained as a yellow solid. MS: m/e=237.1 [M+H]$^+$.

c) [3-(5-Fluoro-pyridin-2-yl)-isoxazol-4-yl]-methanol

To a solution of 3-(5-fluoro-pyridin-2-yl)-isoxazole-4-carboxylic acid ethyl ester (1.0 g, 4.23 mmol) in THF (52 mL) was added portionwise lithiumaluminiumhydride (89 mg, 2.33 mmol) at 0° C. and the reaction mixture was stirred at room temperature for 1 h. The mixture was then cooled to 0° C. and water (88 µL) added followed by sodium hydroxide (15% solution, 88 µL) and then again water (264 µL) and the mixture then stirred overnight at room temperature. The precipitate was then filtered off and washed with THF. The combined washings and filtrate were then evaporated. Purification by chromatography (silica, heptane:ethyl acetate=100:0 to 1:1) afforded the title compound (249 mg, 30%) which was obtained as a light yellow solid.
MS: m/e=195.1 [M+H]$^+$.

d) 3-(5-Fluoro-pyridin-2-yl)-isoxazole-4-carbaldehyde

To a solution of [3-(5-fluoro-pyridin-2-yl)-isoxazol-4-yl]-methanol (2.1 g, 10.8 mmol) in DCM (45 mL) was added a suspension of DMP (5.5 g, 13.0 mmol) in DCM (35 mL) portionwise and under Argon at room temperature and then the mixture was cooled to 0° C. and the resulting mixture warmed up to room temperature overnight. The mixture was then poured carefully into stirred saturated sodium hydrogen carbonate solution and the aqueous layer extracted with DCM. The combined organic layers were then washed with brine, dried over sodium sulfate and evaporated. Purification by chromatography (silica, 0 to 100% ethyl acetate in heptane) gave the title compound (1.85 g, 89%) as a white solid. MS: m/e=193.1 [M+H]$^+$.

e) 2-{2-[3-(5-Fluoro-pyridin-2-yl)-isoxazol-4-yl]-2-hydroxy-ethyl}-4-methyl-thiazole-5-carboxylic acid To a stirred solution of 2,4-dimethyl-thiazole-5-carboxylic acid (1.36 g, 8.63 mmol) in THF (72 mL) at −70° C. and under argon was added BuLi (1.6M in hexanes, 10.8 mL, 17.27 mmol) dropwise. After 2 h a solution of 3-(5-fluoro-pyridin-2-yl)-isoxazole-4-carbaldehyde (1.78 g, 8.63 mmol) in THF (26 mL) was added dropwise. After 1 h the reaction mixture was quenched with citric acid solution (5%, 55 mL) then warmed to room temperature and extracted with ethyl acetate. The combined extracts were washed with brine, water, dried over sodium sulfate, filtered and concentrated. Purification by recrystallization (ethyl acetate) afforded the title compound (1.67 g, 55%) as a light yellow solid. MS: m/e=348.2 [M−H]$^-$.

f) 2-{(E)-2-[3-(5-Fluoro-pyridin-2-yl)-isoxazol-4-yl]-vinyl}-4-methyl-thiazole-5-carboxy-lic acid Concentrated sulfuric acid (27 mL) was added to 2-{2-[3-(5-fluoro-pyridin-2-yl)-isoxazol-4-yl]-2-hydroxy-ethyl}-4-methyl-thiazole-5-carboxylic acid (1.6 g, 4.6 mmol) then the mixture was heated at 90° C. for 20 min. After cooling to room temperature the mixture was poured into ice (200 g) and the precipitate was filtered off and dried to give the title product (930 mg, 61%) as a light yellow solid after trituration from ethyl acetate. MS: m/e=330.3 [M−H]$^-$.

g) 2-{(E)-2-[3-(5-Fluoro-pyridin-2-yl)-isoxazol-4-yl]-vinyl}-4-methyl-thiazole-5-carbox-ylic acid (tetrahydro-pyran-4-yl)-amide To a solution of 2-{(E)-2-[3-(5-fluoro-pyridin-2-yl)-isoxazol-4-yl]-vinyl}-4-methyl-thiazole-5-carboxylic acid (99 mg, 0.3 mmol) in DMF (1.5 mL) were added 2-(1H-benzotriazole-1-yl)-1,1,3,3-tetramethyluronium tetrafluoroborate (106 mg, 0.33 mmol), N,N-diisopropyl ethyl amine (257 µL, 1.5 mmol) and 4-aminotetrahydropyran (33 mg, 0.33 mmol). The resulting reaction mixture was stirred for 1 h. The reaction mixture was then evaporated and purification by trituration from methanol/water afforded the title compound (103 mg, 83%) as an off white solid. MS: m/e=415.2 [M+H]$^+$.

Example 91

2-{(E)-2-[3-(5-Fluoro-pyridin-2-yl)-isoxazol-4-yl]vinyl}-4-methyl-thiazole-5-carboxylic acid cyclopropylamide

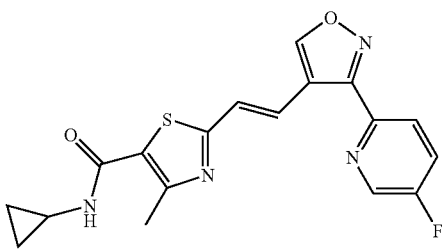

As described for example 90 g, 2-{(E)-2-[3-(5-fluoro-pyridin-2-yl)-isoxazol-4-yl]-vinyl}-4-methyl-thiazole-5-carboxylic acid (99 mg, 0.3 mmol) was converted, using cyclopropylamine instead of 4-aminotetrahydropyran, to the title compound (53 mg, 48%) which was obtained as a yellow solid. MS: m/e=371.1 [M+H]+.

Example 92

2-{(E)-2-[3-(5-Fluoro-pyridin-2-yl)-isoxazol-4-yl]-vinyl}-4-methyl-thiazole-5-carboxylic acid cyclopropylmethyl-amide

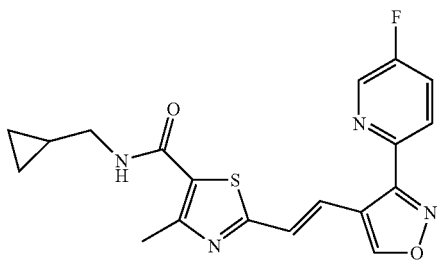

As described for example 90 g, 2-{(E)-2-[3-(5-fluoro-pyridin-2-yl]-isoxazol-4-yl]-vinyl}-4-methyl-thiazole-5-carboxylic acid (99 mg, 0.3 mmol) was converted, using aminomethylcyclopropane instead of 4-aminotetrahydropyran, to the title compound (51 mg, 44%) which was obtained as an off white solid after purification by chromatography (silica, 0 to 100% ethyl acetate in heptane) and recrystallization from heptane/ethyl acetate. MS: m/e=385.1 [M+H]+.

Example 93

2-[(E)-2-(3-Butyl-5-methyl-isoxazol-4-yl)-vinyl]-4-methyl-thiazole-5-carboxylic acid isopropylamide

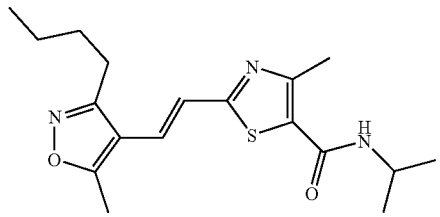

a) 3-Butyl-5-methyl-isoxazole-4-carbaldehyde

To a stirred solution of PCC (4.96 g, 23 mmol) and anhydrous magnesium sulfate (7.40 g, 61 mmol) in DCM (60 mL) was added a solution of (3-butyl-5-methyl-isoxazol-4-yl)-methanol (2.6 g, 15 mmol) in DCM (60 mL) at room temperature and under argon. After 3 h the reaction mixture was diluted with ether (100 mL) and filtered through a bed of silica. The filtrate was concentrated in vacuo and purified by chromatography (silica, 0 to 50% ethyl acetate in heptane) to give the title compound (2.15 g, 84%) as a colourless liquid. MS: m/e=168.0 [M+H]+.

b) 2-[2-(3-Butyl-5-methyl-isoxazol-4-yl)-2-hydroxy-ethyl]-4-methyl-thiazole-5-carboxylic acid methyl ester To a stirred solution of 2,4-dimethyl-thiazole-5-carboxylic acid (7.52 g, 47.8 mmol) in THF (400 mL) at −78° C. and under argon was added n-butyllithium (59.8 mL of a 1.60M solution in hexane, 95.7 mmol) dropwise. After 1.5 h, a solution of 3-butyl-5-methyl-isoxazole-4-carbaldehyde (8.0 g, 47.8 mmol) in THF (200 mL) was added dropwise over 30 min. After 3 h the reaction mixture was quenched with HCl (1 N, 80 mL) and water (100 mL), warmed to room temperature, then the reaction mixture was adjusted to pH 6 with 10% aqueous citric acid. The reaction mixture was concentrated to remove most of the THF then was extracted with ethyl acetate. The combined extracts were dried, filtered and concentrated. The resultant oil was redissolved in methanol (400 mL) and ether (200 mL) then (trimethylsilyl)diazomethane (71.8 ml, of a 2M solution in ether, 144 mmol) was added dropwise. After 30 min, further (trimethylsilyl)diazomethane (71.8 mL of a 2M solution in ether, 144 mmol) was added. After 30 min, the reaction mixture was quenched with acetic acid then saturated aqueous sodium bicarbonate (200 mL) added. The mixture was filtered and the filtrates concentrated to ~200 mL then extracted with in ethyl acetate. The combined organic extracts were dried, filtered and concentrated then purified by chromatography (silica, 10 to 40% ethyl acetate in heptane) to give the title compound (12.8 g, 79%) as a yellow solid. MS: m/e=321.2 [M+H—H2O]+.

c) 2-[(E)-2-(3-Butyl-5-methyl-isoxazol-4-yl)-vinyl]-4-methyl-thiazole-5-carboxylic acid methyl ester Concentrated sulfuric acid (85 mL) was added to 2-[2-(3-butyl-5-methyl-isoxazol-4-yl)-2-hydroxy-ethyl]-4-methyl-thiazole-5-carboxylic acid methyl ester (9.0 g, 26.6 mmol) then the mixture was heated at 90° C. for 2 h. The solution was carefully dropped into 2N sodium hydroxide (1580 mL) and ethyl acetate (100 mL) saturated sodium bicarbonate was added until pH 10 was reached. The reaction mixture was extracted with ethyl acetate then the combined organic extracts were dried, filtered and concentrated, to give the title compound (8.02 g, 94%) as a yellow oil that was used directly without further purification. MS: m/e=321.2 [M+H]+.

d) 2-[(E)-2-(3-Butyl-5-methyl-isoxazol-4-yl)-vinyl]-4-methyl-thiazole-5-carboxylic acid isopropylamide To a stirred solution of isopropylamine (59 mg, 1.0 mmol) in dioxane (2 mL) under argon and at room temperature was added trimethylaluminium (0.50 mL of a 2M solution in toluene, 1.0 mmol). After 1 h, a solution of 2-[(E)-2-(3-butyl-5-methyl-isoxazol-4-yl)-vinyl]-4-methyl-thiazole-5-carboxylic acid methyl ester (80 mg, 0.25 mmol) in dioxane (2 mL) was added and the reaction mixture warmed to 90° C. After 48 h, the reaction mixture was cooled, quenched with Seignettes's salt solution (2 mL) and water (2 mL), then extracted with ethyl acetate. The combined organic extracts were dried, filtered and concentrated. Purification by chromatography (silica, 10 to 80% ethyl acetate in heptane) gave the title compound (59 mg, 68%) as pale yellow solid. MS: m/e=348.0 [M+H]+.

Example 94

2-[(E)-2-(3-Butyl-5-methyl-isoxazol-4-yl)-vinyl]-4-methyl-thiazole-5-carboxylic acid (tetrahydro-furan-3-yl)-amide

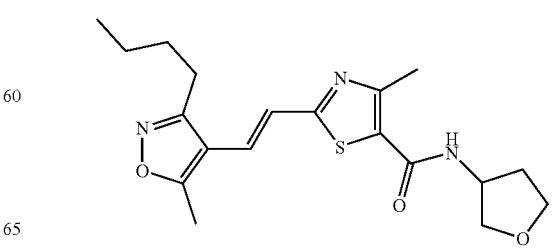

As described for example 93d, 2-[(E)-2-(3-butyl-5-methyl-isoxazol-4-yl)-vinyl]-4-methyl-thiazole-5-carboxylic acid methyl ester (80 mg, 0.25 mmol) was converted, using 3-amino-tetrahydrofuran instead of isopropylamine, to the title compound (43 mg, 46%) which was obtained as a white solid. MS: m/e=376.3 [M+H]⁺.

Example 95

2-[(E)-2-(3-Butyl-5-methyl-isoxazol-4-yl)-vinyl]-4-methyl-thiazole-5-carboxylic acid (2-hydroxy-ethyl)-amide

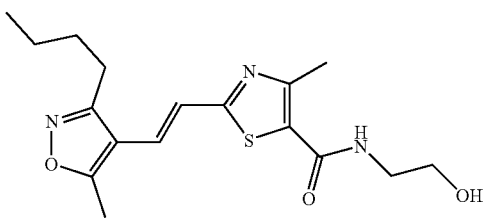

To a stirred solution of 2-[(E)-2-(3-butyl-5-methyl-isoxazol-4-yl)-vinyl]-4-methyl-thiazole-5-carboxylic acid methyl ester (70 mg, 0.22 mmol) in toluene (0.5 mL) was added ethanolamine (16 mg, 0.26 mmol) and TBD (18 mg, 0.12 mmol). After 20 h the reaction mixture was concentrated in vacuo then purified by chromatography (silica, 0 to 10% methanol in dichloromethane) to give the title compound (14 mg, 18%) as a white solid. MS: m/e=350.3 [M+H]⁺.

Example 96

2-[(E)-2-(3-Butyl-5-methyl-isoxazol-4-yl)-vinyl]-4-methyl-thiazole-5-carboxylic acid (tetrahydro-pyran-4-yl)-amide

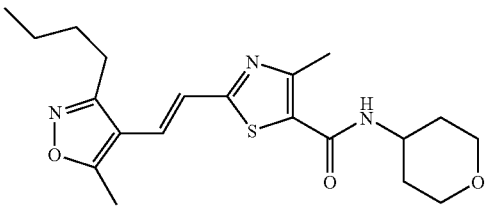

As described for example 93d, 2-[(E)-2-(3-butyl-5-methyl-isoxazol-4-yl)-vinyl]-4-methyl-thiazole-5-carboxylic acid methyl ester (60 mg, 0.19 mmol) was converted, using 4-aminotetrahydropyran instead of isopropylamine, to the title compound (55 mg, 75%) which was obtained as a white solid. MS: m/e=390.3 [M+H]⁺.

Example 97

Rac-2-[(E)-2-(3-Butyl-5-methyl-isoxazol-4-yl)-vinyl]-4-methyl-thiazole-5-carboxylic acid (2-hydroxy-1-methyl-ethyl)-amide

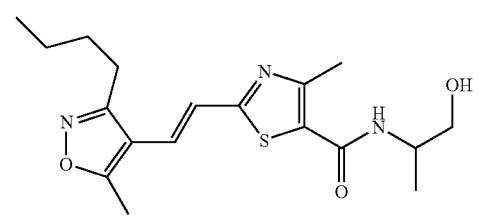

As described for example 95, 2-[(E)-2-(3-butyl-5-methyl-isoxazol-4-yl)-vinyl]-4-methyl-thiazole-5-carboxylic acid methyl ester (60 mg, 0.19 mmol) was converted, using rac-2-amino-1-propanol instead of isopropylamine, to the title compound (45 mg, 79%) which was obtained as a colourless oil. MS: m/e=364.1 [M+H]⁺.

Example 98

2-[(E)-2-(3-Butyl-5-methyl-isoxazol-4-yl)-vinyl]-4-methyl-thiazole-5-carboxylic acid (2-hydroxy-1-hydroxymethyl-ethyl)-amide

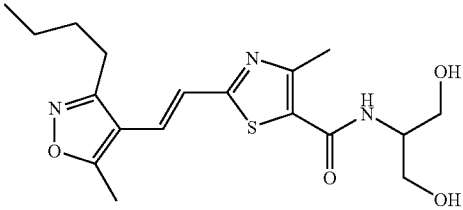

As described for example 95, 2-[(E)-2-(3-butyl-5-methyl-isoxazol-4-yl)-vinyl]-4-methyl-thiazole-5-carboxylic acid methyl ester (60 mg, 0.19 mmol) was converted, using 2-amino-1,3-propanediol instead of isopropylamine, to the title compound (61 mg, 86%) which was obtained as a colourless oil. MS: m/e=380.4 [M+H]⁺.

Example 99

2-[(E)-2-(3-Butyl-5-methyl-isoxazol-4-yl)-vinyl]-4-methyl-thiazole-5-carboxylic acid

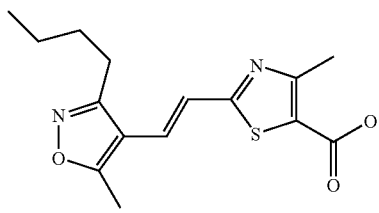

To a suspension of 2-[(E)-2-(3-butyl-5-methyl-isoxazol-4-yl)-vinyl]-4-methyl-thiazole-5-carboxylic acid methyl ester (150 mg, 0.47 mmol) in THF (1.5 mL) was added a solution of lithium hydroxide monohydrate (39 mg, 0.93 mmol) in water (1.5 mL) followed by methanol (1 mL) and the resulting mixture stirred at room temperature for 1 h. The mixture was then evaporated to half volume and then acidified to pH 4 with HCl (1 N) and cooled to 0° C. for 30 min. A solid precipitated and was filtered off and dried to afford the title compound (130 mg, 91%) which was obtained as a light yellow solid. MS: m/e=305.2 [M−H]⁻.

Example 100

2-[(E)-2-(3-Butyl-5-methyl-isoxazol-4-yl)-vinyl]-4-methyl-thiazole-5-carboxylic acid amide

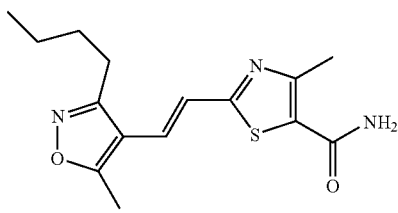

To a solution of 2-[(E)-2-(3-butyl-5-methyl-isoxazol-4-yl)-vinyl]-4-methyl-thiazole-5-carboxylic acid (100 mg, 0.33 mmol) in DMF (3 mL) was added 1,1'-carbonyldiimidazole (64 mg, 0.39 mmol). The resulting reaction mixture was stirred for 1 h at 60° C. and then treated with an ammonium hydroxide solution (490 µL, 3.3 mmol) and stirred for 1 h at room temperature. The reaction mixture was then evaporated. Purification by chromatography (silica, heptane:ethyl acetate=1:0 to 1:1) afforded the title compound (84 mg, 84%) as an off white solid. MS: m/e=306.1 [M+H]$^+$.

Example 101

2-[(Z)-2-(3-Butyl-5-methyl-isoxazol-4-yl)-vinyl]-4-methyl-thiazole-5-carboxylic acid (2-hydroxy-ethyl)-amide

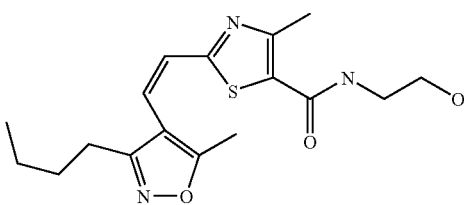

To a stirred solution of 2-[(E)-2-(3-butyl-5-methyl-isoxazol-4-yl)-vinyl]-4-methyl-thiazole-5-carboxylic acid methyl ester (Example 93c, 1.0 g, 3.12 mmol) in toluene (7 mL) was added ethanolamine (229 mg, 3.75 mmol) and TBD (261 mg, 1.88 mmol). After 22 h the reaction mixture was diluted with Seignette's salt and extracted with ethyl acetate. The combined extracts were dried, filtered and concentrated in vacuo, then purified by chromatography (silica, 0 to 10% methanol in dichloromethane) then on a 5×50 cm Chiralpak AD column at room temperature using an isopropanol:heptane (2:8) mobile phase with UV detection at 220 nM to give the less polar component 2-[(E)-2-(3-butyl-5-methyl-isoxazol-4-yl)-vinyl]-4-methyl-thiazole-5-carboxylic acid (2-hydroxy-ethyl)-amide (884 mg, 81%) as a pale yellow solid then the most polar component 2-[(Z)-2-(3-butyl-5-methyl-isoxazol-4-yl)-vinyl]-4-methyl-thiazole-5-carboxylic acid (2-hydroxy-ethyl)-amide (80 mg, 7%) as a pale yellow solid. MS: m/e=350.4 [M+H]+.

Example 102

2-[(E)-2-(3-Butyl-5-methyl-isoxazol-4-yl)-vinyl]-4-methyl-thiazole-5-carboxylic acid N',N'-dimethyl-hydrazide

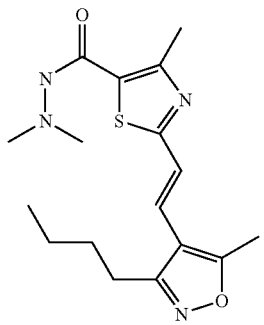

To a solution of 2-[(E)-2-(3-butyl-5-methyl-isoxazol-4-yl)-vinyl]-4-methyl-thiazole-5-carboxylic acid (90 mg, 0.29 mmol) in DMF (5 mL) were added 2-(1H-benzotriazole-1-yl)-1,1,3,3-tetramethyluronium tetrafluoroborate (104 mg, 0.32 mmol), N,N-diisopropyl ethyl amine (250 µL, 1.47 mmol) and 1,1-dimethylhydrazine (0.03 mL, 0.39 mmol). The resulting reaction mixture was stirred for 1 h. The reaction mixture was then evaporated and purification by chromatography (silica, 0 to 2% methanol in dichloromethane) afforded the title compound (45 mg, 44%) as a white solid. MS: m/e=349.3 [M+H]$^+$.

Example 103

2-[(E)-2-(3-Butyl-5-methyl-isoxazol-4-yl)-vinyl]-4-methyl-thiazole-5-carboxylic acid morpholin-4-ylamide

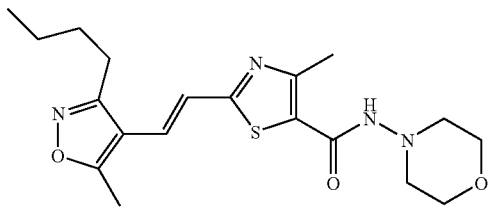

As described for example 102, 2-[(E)-2-(3-butyl-5-methyl-isoxazol-4-yl)-vinyl]-4-methyl-thiazole-5-carboxylic acid (90 mg, 0.29 mmol) was converted, using 4-aminomorpholine instead of 1,1-dimethylhydrazine, to the title compound (43 mg, 37%) which was obtained as an off white solid. MS: m/e=391.3 [M+H]$^+$.

Example 104

Rac-2-[(E)-2-(3-Butyl-5-methyl-isoxazol-4-yl)-vinyl]-4-methyl-thiazole-5-carboxylic acid (1-hydroxymethyl-propyl)-amide

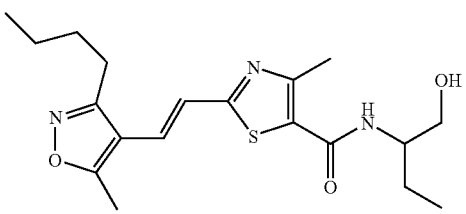

As described for example 102, 2-[(E)-2-(3-butyl-5-methyl-isoxazol-4-yl)-vinyl]-4-methyl-thiazole-5-carboxylic acid (153 mg, 0.5 mmol) was converted, using rac-2-amino-1-butanol instead of 1,1-dimethylhydrazine, to the title compound (98 mg, 52%) which was obtained as a white solid after purification by chromatography (silica, 50 to 100% ethyl acetate in heptane). MS: m/e=378.3 [M+H]⁺.

Example 105

2-[(E)-2-(3-Butyl-5-methyl-isoxazol-4-yl)-vinyl]-4-methyl-thiazole-5-carboxylic acid ((R)-1-hydroxymethyl-propyl)-amide

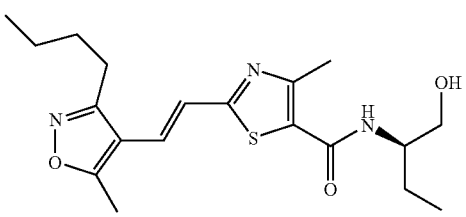

As described for example 104, 2-[(E)-2-(3-butyl-5-methyl-isoxazol-4-yl)-vinyl]-4-methyl-thiazole-5-carboxylic acid (153 mg, 0.5 mmol) was converted, using (R)-2-amino-1-butanol instead of rac-2-amino-1-butanol, to the title compound (151 mg, 80%) which was obtained as a light yellow solid after purification by chromatography (silica, 50 to 100% ethyl acetate in heptane) and recrystallization from ethyl acetate/heptane. MS: m/e=378.3 [M+H]⁺.

Example 106

2-[(E)-2-(3-Butyl-5-methyl-isoxazol-4-yl)-vinyl]-4-methyl-thiazole-5-carboxylic acid ((S)-1-hydroxymethyl-propyl)-amide

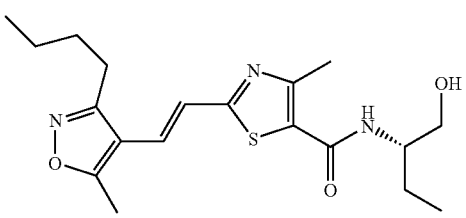

As described for example 105, 2-[(E)-2-(3-butyl-5-methyl-isoxazol-4-yl)-vinyl]-4-methyl-thiazole-5-carboxylic acid (153 mg, 0.5 mmol) was converted, using (S)-2-amino-1-butanol instead of (R)-2-amino-1-butanol, to the title compound (150 mg, 79%) which was obtained as a light yellow solid after purification by chromatography (silica, 50 to 100% ethyl acetate in heptane) and recrystallization from ethyl acetate/heptane. MS: m/e=378.4 [M+H]⁺.

Example 107

2-[(E)-2-(3-Butyl-5-methyl-isoxazol-4-yl)-vinyl]-4-methyl-thiazole-5-carboxylic acid ((R)-2,2,2-trifluoro-1-methyl-ethyl)-amide

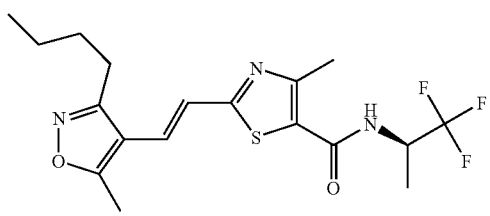

As described for example 104, 2-[(E)-2-(3-butyl-5-methyl-isoxazol-4-yl)-vinyl]-4-methyl-thiazole-5-carboxylic acid (153 mg, 0.5 mmol) was converted, using L-2,2,2,-trifluoro-1-(methyl)ethylamine instead of rac-2-amino-1-butanol, to the title compound (92 mg, 46%) which was obtained as a white solid after purification by chromatography (silica, 50 to 100% ethyl acetate in heptane and recrystallization from ethyl acetate/heptane. MS: m/e=402.3 [M+H]⁺.

Example 108

{2-[(E)-2-(3-Butyl-5-methyl-isoxazol-4-yl)-vinyl]-4-methyl-thiazol-5-yl}-(3,3-difluoro-azetidin-1-yl)-methanone

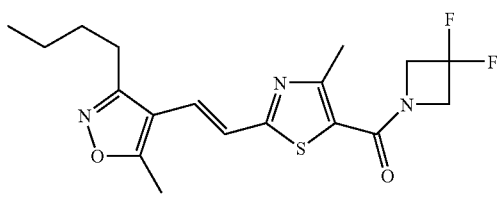

To a stirred solution of 2-[(E)-2-(3-butyl-5-methyl-isoxazol-4-yl)-vinyl]-4-methyl-thiazole-5-carboxylic acid (200 mg, 0.65 mmol), 3,3-difluoroazetidine hydrochloride (93 mg, 0.72 mmol) and N-hydroxysuccinimide (86 mg, 0.74 mmol) in DMF (1 mL) was added 1-(3-dimethylaminopropyl)-3-ethylcarboiimide (144 mg, 0.75 mmol) and DMF (1 mL) followed by triethylamine (0.29 mL, 2.1 mmol) and DMF (2 mL). The resulting mixture was stirred under argon for 20 h and then water added and the mixture extracted with ethyl acetate. The combined organic extracts were dried, filtered and concentrated. Purification by chromatography (silica, 40% ethyl acetate in heptane) gave the title compound (73 mg, 29%) as pale yellow oil. MS: m/e=382.1 [M+H]⁺.

Example 109

{2-[(E)-2-(3-Butyl-5-methyl-isoxazol-4-yl)-vinyl]-4-methyl-thiazol-5-yl}-(3-methoxy-azetidin-1-yl)-methanone

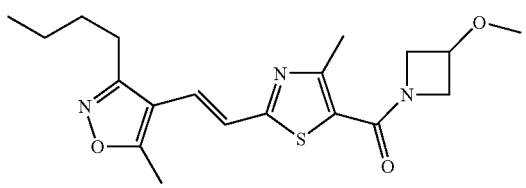

As described for example 108, 2-[(E)-2-(3-butyl-5-methyl-isoxazol-4-yl)-vinyl]-4-methyl-thiazole-5-carboxylic acid (200 mg, 0.65 mmol) was converted, using 3-methoxy-azetidine hydrochloride instead of 3,3-difluoroazetidine hydrochloride, to the title compound (58 mg, 24%) which was obtained as a light yellow oil. MS: m/e=376.3 [M+H]$^+$.

Example 110

Azetidin-1-yl-{2-[(E)-2-(3-butyl-5-methyl-isoxazol-4-yl)-vinyl]-4-methyl-thiazol-5-yl}-methanone

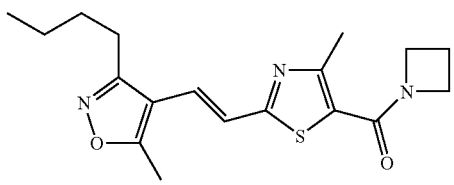

As described for example 108, 2-[(E)-2-(3-butyl-5-methyl-isoxazol-4-yl)-vinyl]-4-methyl-thiazole-5-carboxylic acid (200 mg, 0.65 mmol) was converted, using trimethylene imine instead of 3,3-difluoroazetidine hydrochloride, to the title compound (16 mg, 7%) which was obtained as a light yellow oil. MS: m/e=346.2 [M+H]$^+$.

Example 111

2-[(E)-2-(3-Butyl-5-methyl-isoxazol-4-yl)-vinyl]-4-methyl-thiazole-5-carboxylic acid ((1S,2S)-2-hydroxy-cyclopentyl)-amide

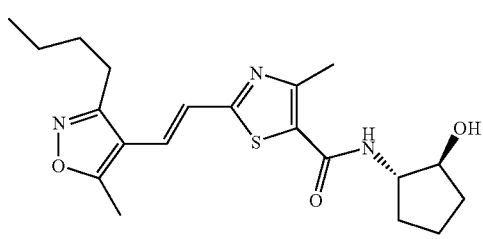

As described for example 104, 2-[(E)-2-(3-butyl-5-methyl-isoxazol-4-yl)-vinyl]-4-methyl-thiazole-5-carboxylic acid (153 mg, 0.5 mmol) was converted, using trans-(1S,2S)-2-aminocyclopentanol hydrochloride instead of rac-2-amino-1-butanol, to the title compound (127 mg, 65%) which was obtained as an off white solid after purification by chromatography (silica, 50 to 100% ethyl acetate in heptane) and recrystallization from ethyl acetate/heptane. MS: m/e=390.3 [M+H]$^+$.

Example 112

2-[(E)-2-(3-Butyl-5-methyl-isoxazol-4-yl)-vinyl]-4-methyl-thiazole-5-carboxylic acid (1-methyl-1-pyrazol-4-yl)-amide

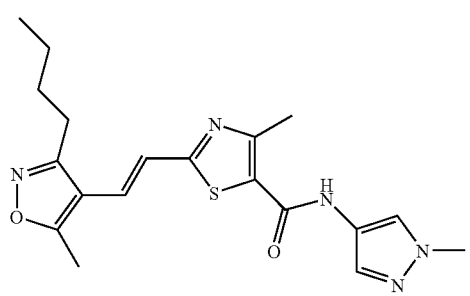

As described for example 104, 2-[(E)-2-(3-butyl-5-methyl-isoxazol-4-yl)-vinyl]-4-methyl-thiazole-5-carboxylic acid (306 mg, 1.0 mmol) was converted, using 1-methyl-1H-pyrazol-ylamine dihydrochloride instead of rac-2-amino-1-butanol, to the title compound (166 mg, 43%) which was obtained as a light yellow solid after purification by chromatography (silica, 50 to 100% ethyl acetate in heptane) and recrystallization from ethyl acetate/heptane. MS: m/e=386.2 [M+H]$^+$.

Example 113

2-[(E)-2-(3-Butyl-5-methyl-isoxazol-4-yl)-vinyl]-4-methyl-thiazole-5-carboxylic acid cyclopropylamide

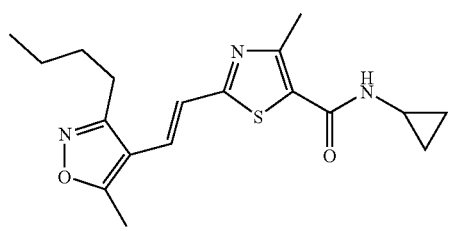

As described for example 104, 2-[(E)-2-(3-butyl-5-methyl-isoxazol-4-yl)-vinyl]-4-methyl-thiazole-5-carboxylic acid (153 mg, 0.5 mmol) was converted, using cyclopropylamine instead of rac-2-amino-1-butanol, to the title compound (76 mg, 44%) which was obtained as a light yellow solid after purification by chromatography (silica, 50 to 100% ethyl acetate in heptane). MS: m/e=346.2 [M+H]$^+$.

Example 114

2-[(E)-2-(3-Butyl-5-methyl-isoxazol-4-yl)-vinyl]-4-methyl-thiazole-5-carboxylic acid ((1R,2R)-2-hydroxy-cyclopentyl)-amide

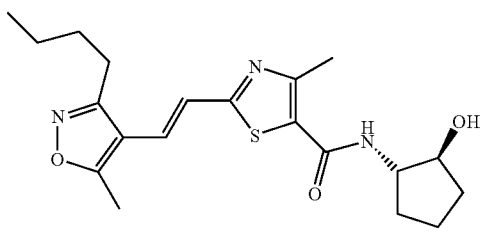

As described for example 104, 2-[(E)-2-(3-butyl-5-methyl-isoxazol-4-yl)-vinyl]-4-methyl-thiazole-5-carboxylic acid (153 mg, 0.5 mmol) was converted, using trans-(−)-2-aminocyclopentanol hydrochloride instead of rac-2-amino-1-butanol, to the title compound (146 mg, 75%) which was obtained as an off white solid after purification by chromatography (silica, 50 to 100% ethyl acetate in heptane) and recrystallization from ethyl acetate/heptane. MS: m/e=390.3 $[M+H]^+$.

Example 115

2-[(E)-2-(3-Butyl-5-methyl-isoxazol-4-yl)-vinyl]-4-methyl-thiazole-5-carboxylic acid cyclobutylamide

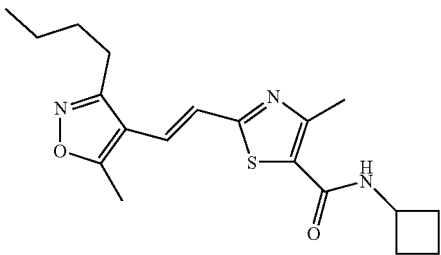

As described for example 108, 2-[(E)-2-(3-butyl-5-methyl-isoxazol-4-yl)-vinyl]-4-methyl-thiazole-5-carboxylic acid (400 mg, 1.3 mmol) was converted, using cyclobutylamine instead of 3,3-difluoroazetidine hydrochloride, to the title compound (68 mg, 15%) which was obtained as a white solid. MS: m/e=360.2 $[M+H]^+$.

Example 116

2-[(E)-2-(3-Butyl-5-methyl-isoxazol-4-yl)-vinyl]-4-methyl-thiazole-5-carboxylic acid cyclopropylmethyl-amide

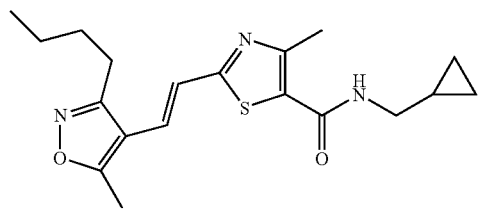

As described for example 104, 2-[(E)-2-(3-butyl-5-methyl-isoxazol-4-yl)-vinyl]-4-methyl-thiazole-5-carboxylic acid (153 mg, 0.5 mmol) was converted, using aminomethylcyclopropane instead of rac-2-amino-1-butanol, to the title compound (93 mg, 52%) which was obtained as a white solid after purification by chromatography (silica, 50 to 100% ethyl acetate in heptane) and recrystallization from ethyl acetate/heptane. MS: m/e=360.2 $[M+H]^+$.

Example 117

2-[(E)-2-(3-Butyl-5-methyl-isoxazol-4-yl)-vinyl]-4-methyl-thiazole-5-carboxylic acid (2-hydroxy-1,1-dimethyl-ethyl)-amide

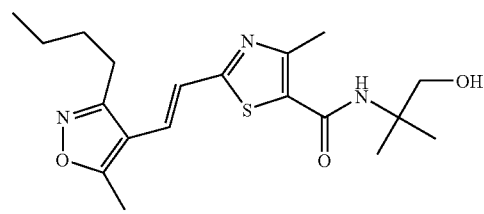

As described for example 104, 2-[(E)-2-(3-butyl-5-methyl-isoxazol-4-yl)-vinyl]-4-methyl-thiazole-5-carboxylic acid (153 mg, 0.5 mmol) was converted, using 2-amino-2-methyl-1-propanol instead of rac-2-amino-1-butanol, to the title compound (87 mg, 46%) which was obtained as a colourless gum after purification by chromatography (silica, 0 to 100% ethyl acetate in heptane). MS: m/e=378.3 $[M+H]^+$.

Example 118

2-[(E)-2-(3-Butyl-5-methyl-isoxazol-4-yl)-vinyl]-4-methyl-thiazole-5-carboxylic acid (1,1-dioxo-tetrahydrothiophen-3-yl)-amide

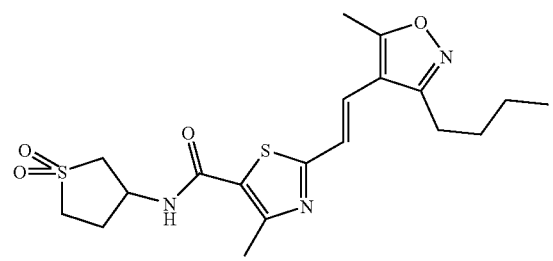

As described for example 104, 2-[(E)-2-(3-butyl-5-methyl-isoxazol-4-yl)-vinyl]-4-methyl-thiazole-5-carboxylic acid (153 mg, 0.5 mmol) was converted, using 1,1-dioxidotetrahydrothien-3-ylamine instead of rac-2-amino-1-butanol, to the title compound (174 mg, 82%) which was obtained as a white solid after purification by chromatography (silica, 50 to 100% ethyl acetate in heptane) and recrystallization from ethyl acetate/heptane. MS: m/e=424.2 $[M+H]^+$.

Example 119

2-[(E)-2-(3-Butyl-5-methyl-isoxazol-4-yl)-vinyl]-4-methyl-thiazole-5-carboxylic acid (2,2,2-trifluoro-ethyl)-amide

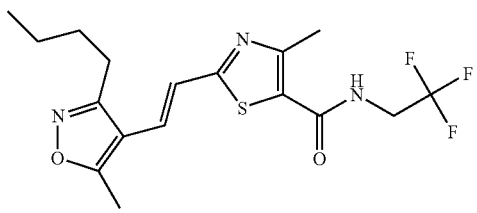

As described for example 104, 2-[(E)-2-(3-butyl-5-methyl-isoxazol-4-yl)-vinyl]-4-methyl-thiazole-5-carboxylic acid (153 mg, 0.5 mmol) was converted, using 2,2,2-trifluoroethylamine instead of rac-2-amino-1-butanol, to the title compound (131 mg, 68%) which was obtained as a white solid after purification by chromatography (silica, 50 to 100% ethyl acetate in heptane) and recrystallization from ethyl acetate/heptane. MS: m/e=388.2 [M+H]$^+$.

Example 120

{2-[(E)-2-(3-Butyl-5-methyl-isoxazol-4-yl)-vinyl]-4-methyl-thiazol-5-yl}-morpholin-4-yl-methanone

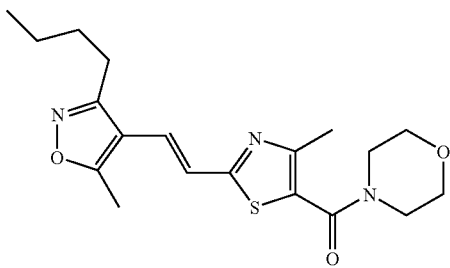

As described for example 104, 2-[(E)-2-(3-butyl-5-methyl-isoxazol-4-yl)-vinyl]-4-methyl-thiazole-5-carboxylic acid (153 mg, 0.5 mmol) was converted, using morpholine instead of rac-2-amino-1-butanol, to the title compound (98 mg, 52%) which was obtained as a colourless gum after purification by chromatography (silica, 0 to 100% ethyl acetate in heptane). MS: m/e=376.3 [M+H]$^+$.

Example 121

2-[(E)-2-(3-Butyl-5-methyl-isoxazol-4-yl)-vinyl]-4-methyl-thiazole-5-carboxylic acid ethylamide

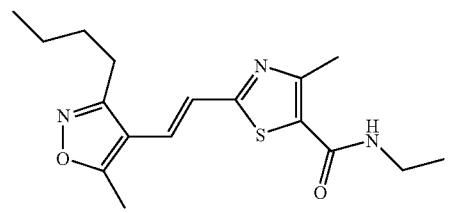

As described for example 104, 2-[(E)-2-(3-butyl-5-methyl-isoxazol-4-yl)-vinyl]-4-methyl-thiazole-5-carboxylic acid (153 mg, 0.5 mmol) was converted, using ethylamine (2M solution in THF) instead of rac-2-amino-1-butanol, to the title compound (91 mg, 55%) which was obtained as a light yellow solid after purification by chromatography (silica, 0 to 100% ethyl acetate in heptane). MS: m/e=334.2 [M+H]$^+$.

Example 122

2-[(E)-2-(3-Butyl-5-methyl-isoxazol-4-yl)-vinyl]-4-methyl-thiazole-5-carboxylic acid methylamide

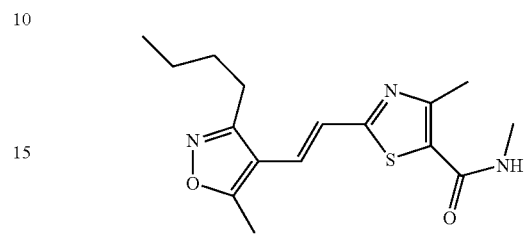

As described for example 104, 2-[(E)-2-(3-butyl-5-methyl-isoxazol-4-yl)-vinyl]-4-methyl-thiazole-5-carboxylic acid (153 mg, 0.5 mmol) was converted, using methylamine (2M solution in THF) instead of rac-2-amino-1-butanol, to the title compound (89 mg, 56%) which was obtained as a white solid after purification by chromatography (silica, 0 to 100% ethyl acetate in heptane) and recrystallization from ethyl acetate/heptane. MS: m/e=320.1 [M+H]$^+$.

Example 123

{2-[(E)-2-(3-Butyl-5-methyl-isoxazol-4-yl)-vinyl]-4-methyl-thiazol-5-yl}-(2-oxa-6-aza-spiro[3.3]hept-6-yl)-methanone

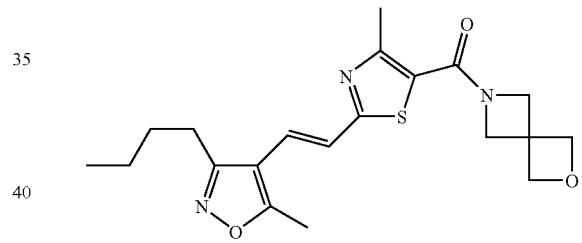

As described for example 108, 2-[(E)-2-(3-butyl-5-methyl-isoxazol-4-yl)-vinyl]-4-methyl-thiazole-5-carboxylic acid (50 mg, 0.16 mmol) was converted, using 2-oxa-6-azonia-spiro[3.3]heptane oxalate salt instead of 3,3-difluoroazetidine hydrochloride, to the title compound (32 mg, 51%) which was obtained as a white solid after purification by chromatography (silica, 3 to 5% methanol in dichloromethane). MS: m/e=388.2 [M+H]$^+$.

Example 124

2-[(E)-2-(3-Butyl-5-methyl-isoxazol-4-yl)-vinyl]-thiazole-5-carboxylic acid isoprop-ylamide

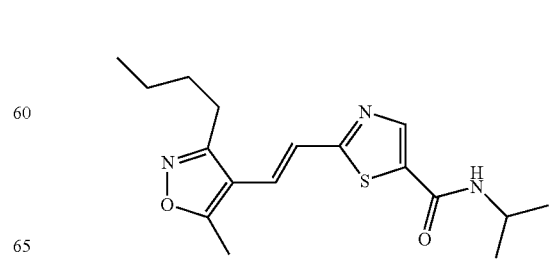

a) 2-[2-(3-Butyl-5-methyl-isoxazol-4-yl)-2-hydroxy-ethyl]-thiazole-5-carboxylic acid methyl ester To a stirred solution of 2-methyl-thiazole-5-carboxylic acid (215 mg, 1.50 mmol) in THF (10 mL) at −78° C. and under argon was added n-butyllithium (1.88 mL of a 1.60M solution in hexane, 3.0 mmol) dropwise. After 1 h, a solution of 3-butyl-5-methyl-isoxazole-4-carbaldehyde (251 mg, 1.50 mmol) in THF (10 mL) was added dropwise. After 2 h the reaction mixture was quenched with 10% aqueous citric acid (10 mL) then warmed to room temperature. The reaction mixture was extracted with ethyl acetate then the combined extracts were dried, filtered and concentrated. The resultant oil was redissolved in methanol (15 mL) and ether (7 mL) then (trimethylsilyl)diazomethane (2.25 mL of a 2M solution in ether, 4.5 mmol) was added dropwise. After 30 min, further (trimethylsilyl)diazomethane (2.25 mL of a 2M solution in ether, 4.5 mmol) was added. After 30 min, the reaction mixture was quenched with acetic acid (3 drops) then was concentrated and the residue redissolved in ethyl acetate and washed with NaOH (2 N). The organic phase was dried, filtered and concentrated then purified by chromatography (silica, 0 to 4% methanol in dichloromethane) to give the title compound (49 mg, 10%) as a brown oil. MS: m/e=307.3 [M+H]$^+$.

b) 2-[(E)-2-(3-Butyl-5-methyl-isoxazol-4-yl)-vinyl]-thiazole-5-carboxylic acid isoprop-ylamide 2-[2-(3-Butyl-5-methyl-isoxazol-4-yl)-2-hydroxy-ethyl]-thiazole-5-carboxylic acid methyl ester (30 mg, 0.092 mmol) was stirred with concentrated sulfuric acid (0.1 mL) for 30 min, then the reaction mixture quenched with saturated sodium bicarbonate solution and extracted with ethyl acetate. The combined organic phases were dried, filtered and concentrated, then dissolved in toluene (0.5 mL) and isopropylamine (22 mg, 0.37 mmol) and TBD (13 mg, 0.092 mmol) added. The reaction mixture was then heated at 90° C. for 15 h and then the reaction mixture was concentrated then purified by chromatography (silica, 0 to 3% methanol in dichloromethane) to give the title compound (10 mg, 34%) as a pale yellow oil. MS: m/e=334.3 [M+H]$^+$.

Example 125

2-[(E)-2-(3-Butyl-5-methyl-isoxazol-4-yl)-vinyl]-thiazole-5-carboxylic acid (2-hydroxy-ethyl)-amide

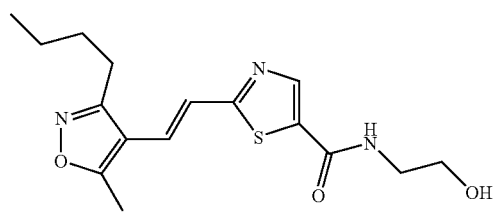

As described for example 124b, 2-[2-(3-butyl-5-methyl-isoxazol-4-yl)-2-hydroxy-ethyl]-thiazole-5-carboxylic acid methyl ester (90 mg, 0.29 mmol) was converted, using ethanolamine instead of isopropylamine, to the title compound (35 mg, 35%) which was obtained as a light yellow solid after purification by chromatography (silica, 0 to 10% methanol in dichloromethane). MS: m/e=336.3 [M+H]$^+$.

Example 126

2-(5-Methyl-3-phenyl-isoxazol-4-ylmethoxy)-thiazole-5-carboxylic acid ethyl ester

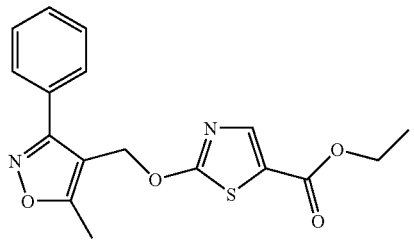

To a stirred suspension of sodium hydride (304 mg, 6.98 mmol, 60% dispersion in mineral oil) in tetrahydrofuran (30 mL) at 0° C. under argon was added (5-methyl-3-phenyl-isoxazol-4-yl)-methanol (1.0 g, 5.28 mmol) The mixture was warmed to room temperature and after 1 h the reaction mixture was cooled to 0° C. then a solution of 2-chloro-thiazole-5-carboxylic acid ethyl ester (1.01 g, 5.28 mmol) in THF (15 mL) added. The reaction mixture was warmed to room temperature and after 15 h, water (20 mL) was added and the resulting mixture extracted with ethyl acetate. The combined organic extracts were dried, filtered and concentrated. Purification by chromatography (silica, 20% ethyl acetate in heptane) gave the title compound (940 mg, 52% yield) as an off-white solid. MS: m/e=345.0 [M+H]$^+$.

Example 127

2-(5-Methyl-3-phenyl-isoxazol-4-ylmethoxy)-thiazole-5-carboxylic acid isoprop-ylamide

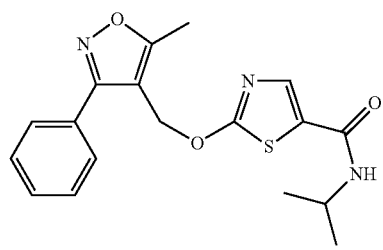

To a stirred solution of isopropylamine (66 mg, 1.12 mmol) in dioxane (5 mL) under argon and at room temperature was added trimethylaluminium (0.60 mL of a 2M solution in toluene, 1.20 mmol). After 1 h, a solution of 2-(5-methyl-3-phenyl-isoxazol-4-ylmethoxy)-thiazole-5-carboxylic acid ethyl ester (100 mg, 0.28 mmol) in dioxane (5 mL) was added and the reaction mixture warmed to 90° C. After 3 h, the reaction mixture was cooled, quenched with Seignettes's salt solution and water, then extracted with dichloromethane. The combined organic extracts were dried, filtered and concentrated. Purification by chromatography (silica, 0 to 3% methanol in dichloromethane) gave the title compound (68 mg, 69%) as a white solid. MS: m/e=358.1 [M+H]$^+$.

Example 128

2-(5-Methyl-3-phenyl-isoxazol-4-ylmethoxy)-thiazole-5-carboxylic acid (tetrahydro-pyran-4-yl)-amide

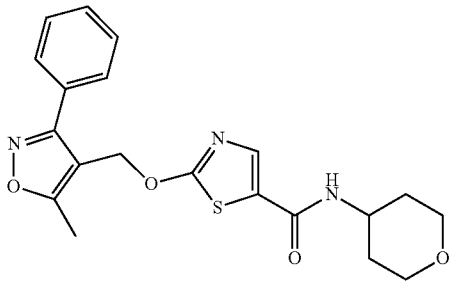

As described for example 127, 2-(5-methyl-3-phenyl-isoxazol-4-ylmethoxy)-thiazole-5-carboxylic acid ethyl ester (100 mg, 0.28 mmol) was converted, using 4-aminotetrahydropyran instead of isopropylamine, to the title compound (65 mg, 56%) which was obtained as a white solid after purification by chromatography (silica, 0 to 3% methanol in dichloromethane). MS: m/e=398.0 [M+H]$^+$.

Example 129

2-(5-Methyl-3-phenyl-isoxazol-4-ylmethoxy)-thiazole-5-carboxylic acid (2-hydroxy-1-methyl-ethyl)-amide

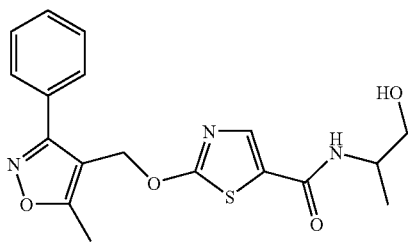

As described for example 127, 2-(5-methyl-3-phenyl-isoxazol-4-ylmethoxy)-thiazole-5-carboxylic acid ethyl ester (200 mg, 0.56 mmol) was converted, using rac-2-amino-1-propanol instead of isopropylamine, to the title compound (94 mg, 43%) which was obtained as a colourless gum after purification by chromatography (silica, 0 to 3% methanol in dichloromethane). MS: m/e=374.0 [M+H]$^+$.

Example 130

2-(5-Methyl-3-phenyl-isoxazol-4-ylmethoxy)-thiazole-5-carboxylic acid (2-hydroxy-ethyl)-amide

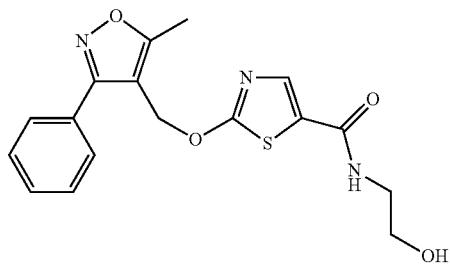

As described for example 127, 2-(5-methyl-3-phenyl-isoxazol-4-ylmethoxy)-thiazole-5-carboxylic acid ethyl ester (100 mg, 0.28 mmol) was converted, using ethanolamine instead of isopropylamine, to the title compound (62 mg, 59%) which was obtained as a colourless gum after purification by chromatography (silica, 0 to 3% methanol in dichloromethane). MS: m/e=360.3 [M+H]$^+$.

Example 131

2-(5-Methyl-3-phenyl-isoxazol-4-ylmethoxy)-thiazole-5-carboxylic acid (2-hydroxy-1,1-dimethyl-ethyl)-amide

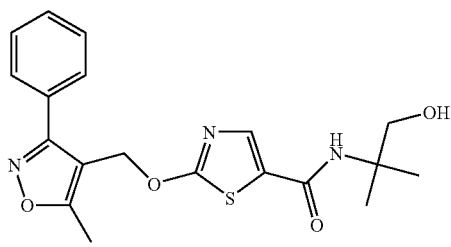

As described for example 127, 2-(5-methyl-3-phenyl-isoxazol-4-ylmethoxy)-thiazole-5-carboxylic acid ethyl ester (95 mg, 0.28 mmol) was converted, using 2-amino-2-methyl-1-propanol instead of isopropylamine, to the title compound (25 mg, 23%) which was obtained as a colourless gum after purification by chromatography (silica, 0 to 3% methanol in dichloromethane). MS: m/e=388.3 [M+H]$^+$.

Example 132

2-(3-Butyl-5-methyl-isoxazol-4-ylmethoxy)-thiazole-5-carboxylic acid isopropylamide

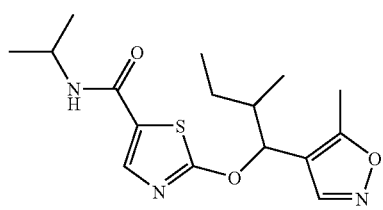

a) 2-Chloro-thiazole-5-carboxylic acid isopropylamide

To a stirred solution of isopropylamine (123 mg, 2.08 mmol) in dioxane (5 mL) under argon and at room temperature was added trimethylaluminium (1.04 mL of a 2M solution in toluene, 2.08 mmol). After 1 h, a solution of 2-chloro-thiazole-5-carboxylic acid ethyl ester (100 mg, 0.522 mmol) in dioxane (5 mL) was added and the reaction mixture warmed to 90° C. After 6 h, the reaction mixture was cooled, quenched with Seignettes's salt solution and water, then extracted with dichloromethane. The combined organic extracts were dried, filtered and concentrated. Purification by chromatography (silica, 0 to 30% ethyl acetate in heptane) gave the title compound (100 mg, 94%) as a white solid. MS: m/e=203.4 [M+H]$^+$.

b) 2-(3-Butyl-5-methyl-isoxazol-4-ylmethoxy)-thiazole-5-carboxylic acid isopropylamide To a suspension of NaH (55%, 58 mg, 2.4 mmol) in THF (3 mL) at 0° C., was added a solution of (3-butyl-5-methyl-isoxazol-4-yl)-methanol (169 mg, 1.0 mmol) in THF (3 mL) dropwise. The resulting mixture was stirred for 1 h and then cooled to 0° C. and then a solution of 2-chloro-thiazole-5-carboxylic acid isopropylamide (205 mg, 1.0 mmol) in THF (3 mL) added dropwise and the resulting mixture stirred at room temperature overnight. Water was then added and the resulting mixture extracted with ethyl acetate. The combined organic extracts were dried, filtered and concentrated. Purification by chromatography (silica, 0 to 30% methanol in dichloromethane, then 0 to 60% ethyl acetate in heptane) gave the title compound (145 mg, 43%) as a white solid. MS: m/e=338.4 [M+H]$^+$.

Example 133

Rac-2-(3-Butyl-5-methyl-isoxazol-4-ylmethoxy)-thiazole-5-carboxylic acid (2-hydroxy-1-methyl-ethyl)-amide

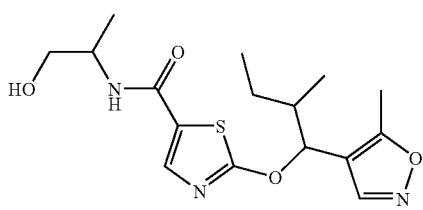

a) 2-(3-Butyl-5-methyl-isoxazol-4-ylmethoxy)-thiazole-5-carboxylic acid ester To a suspension of NaH (55%, 340 mg, 7.8 mmol) in THF (25 mL) at 0° C., was added a solution of (3-butyl-5-methyl-isoxazol-4-yl)-methanol (1.0 g, 5.9 mmol) in THF (5 mL) dropwise. The resulting mixture was stirred for 1 h and then cooled to 0° C. and then a solution of 2-chloro-thiazole-5-carboxylic acid ester (1.13 g, 5.9 mmol) in THF (15 mL) added dropwise and the resulting mixture stirred at room temperature overnight. Water was then added and the resulting mixture extracted with ethyl acetate. The combined organic extracts were dried, filtered and concentrated. Purification by chromatography (silica, 0 to 30% ethyl acetate in heptane) gave the title compound (980 mg, 51%) as a light yellow oil and used directly in the next reaction step.

b) Rac-2-(3-Butyl-5-methyl-isoxazol-4-ylmethoxy)-thiazole-5-carboxylic acid (2-hydroxy-1-methyl-ethyl)-amide To a stirred solution of 2-(3-butyl-5-methyl-isoxazol-4-ylmethoxy)-thiazole-5-carboxylic acid ester (150 mg, 0.46 mmol) in toluene (0.3 mL) was added rac-2-amino-1-propanol (42 mg, 0.56 mmol) and TBD (19 mg, 0.13 mmol). After 15 h the reaction mixture was concentrated in vacuo then purified by chromatography (silica, 0 to 25% methanol in dichloromethane) to give the title compound (120 mg, 73%) as a colourless oil. MS: m/e=354.1 [M+H]$^+$.

Example 134

2-(3-Butyl-5-methyl-isoxazol-4-ylmethoxy)-thiazole-5-carboxylic acid (2-hydroxy-ethyl)-amide

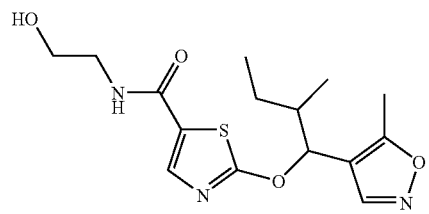

As described for example 134b, 2-(3-butyl-5-methyl-isoxazol-4-ylmethoxy)-thiazole-5-carboxylic acid ester (150 mg, 0.46 mmol) was converted, using ethanolamine instead of rac-2-amino-1-propanol, to the title compound (90 mg, 57%) which was obtained as a colourless oil after purification by chromatography (silica, 0 to 25% methanol in dichloromethane). MS: m/e=340.3 [M+H]$^+$.

Example 135

2-[(5-Methyl-3-phenyl-isoxazol-4-ylmethyl)-amino]-thiazole-5-carboxylic acid isoprop-ylamide

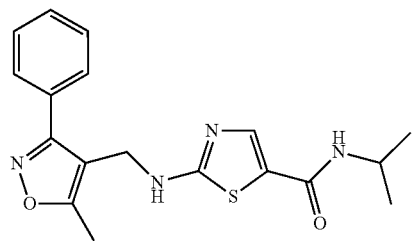

A stirred solution of (5-methyl-3-phenyl-4-isoxazolyl)methylamine (100 mg, 0.53 mmol) and 2-chloro-thiazole-5-carboxylic acid isopropylamide (100 mg, 0.49 mmol) in DMF (5 mL) was heated at 100° C. for 7 days, then at 150° C. under microwave irradiation for 15 min. The reaction mixture was cooled and concentrated in vacuo, then diluted with water and extracted with ethyl acetate. The combined organic extracts were dried, filtered and concentrated, then purified by chromatography (silica, 0 to 3% methanol in dichloromethane) to give the title compound (23 mg, 12%) as a white solid. MS: m/e=357.3 [M+H]$^+$.

Example 136

2-[(5-Methyl-3-phenyl-isoxazol-4-ylmethyl)-amino]-thiazole-5-carboxylic acid (tetra-hydro-pyran-4-yl)-amide

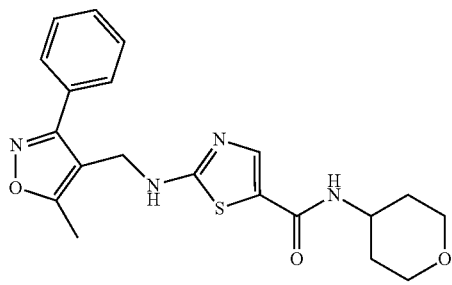

a) 2-Chloro-thiazole-5-carboxylic acid (tetrahydro-pyran-4-yl)-amide

As described for example 135a, 2-chloro-thiazole-5-carboxylic acid ethyl ester (500 mg, 2.6 mmol) was converted, using 4-aminotetrahydropyran instead of isopropylamine, to the title compound (471 mg, 73%) which was obtained as a white solid after purification by chromatography (silica, 0 to 3% methanol in dichloromethane). MS: m/e=247.3 [M+H]$^+$.

b) 2-[(5-Methyl-3-phenyl-isoxazol-4-ylmethyl)-amino]-thiazole-5-carboxylic acid (tetra-hydro-pyran-4-yl)-amide A stirred solution of (5-methyl-3-phenyl-4-isoxazolyl)methylamine (100 mg, 0.53 mmol) and 2-chloro-thiazole-5-carboxylic acid (tetrahydro-pyran-4-yl)-amide (131 mg, 0.53 mmol) in DMF (3 mL) was heated at 150° C. under microwave irradiation for 1 h. The reaction mixture was cooled and concentrated in vacuo, then purified by chromatography (silica, 0 to 3% methanol in dichloromethane) to give the title compound (12 mg, 6%) as a white solid. MS: m/e=399.1 [M+H]$^+$.

The invention claimed is:
1. A compound of formula I,

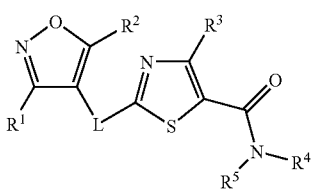

wherein
$R^1$ is selected from the group consisting of
  i) lower alkyl,
  ii) lower alkyl substituted by 1-5 halogen atoms,
  iii) aryl,
  iv) aryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl, H)N—, N(lower alkyl, lower alkyl)-lower alkyl, N(lower alkyl, H)-lower alkyl, nitro, lower alkyl-S(O)$_2$—, carboxy, carboxy-lower alkyl, lower alkyl-COO-lower alkyl, COO-lower alkyl, CO—N(lower alkyl, H)-lower alkyl, CO—N(lower alkyl, lower alkyl)-lower alkyl, CO—NH$_2$-lower alkyl and lower alkyl-CO—,
  v) heteroaryl, and
  vi) heteroaryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl, H)N—, N(lower alkyl, lower alkyl)-lower alkyl, N(lower alkyl, H)-lower alkyl, nitro, lower alkyl-S(O)$_2$—, carboxy, carboxy-lower alkyl, lower alkyl-COO-lower alkyl, lower alkyl-COO—, CO—N(lower alkyl, H)-lower alkyl, CO—N(lower alkyl, lower alkyl)-lower alkyl, CO—NH$_2$-lower alkyl and lower alkyl-CO—,
$R^2$ is H, lower alkyl or lower alkyl substituted by 1-5 substituents individually selected from halogen and hydroxy;
$R^3$ is H, lower alkyl or lower alkyl substituted by 1-5 halogen atoms;
$R^4$ is selected from the group consisting of
  i) H,
  ii) lower alkyl,
  iii) lower alkyl substituted by 1-5 substituents individually selected from acetamidyl, acetyl, acetylamino, amido, amino, carboxy, cyano, cycloalkyl, halogen, halogen-lower alkoxy, heterocyclyl, hydroxy, lower alkoxy, (lower alkyl, lower alkyl)N—, (lower alkyl, H)N—, nitro and lower alkyl-S(O)$_2$—,
  iv) aryl,
  v) heteroaryl,
  vi) heteroaryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl, H)N—, N(lower alkyl, lower alkyl)-lower alkyl, N(lower alkyl, H)-lower alkyl, nitro, lower alkyl-S(O)$_2$—, carboxy, carboxy-lower alkyl, lower alkyl-COO-lower alkyl, lower alkyl-COO—, CO—N(lower alkyl, H)-lower alkyl, CO—N(lower alkyl, lower alkyl)-lower alkyl, CO—NH$_2$-lower alkyl, and lower alkyl-CO—,
  vii) cycloalkyl,
  viii) cycloalkyl substituted by 1-4 substituents individually selected from halogen and hydroxy,
  ix) heterocyclyl, and
  x) —NR$^6$R$^7$;
$R^5$ is H, lower alkyl or lower alkyl substituted by 1-5 halogen atoms;
or $R^4$ and $R^5$ together with the nitrogen to which they are attached form a heterocyclyl or a heterocyclyl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl, H)N—, N(lower alkyl, lower alkyl)-lower alkyl, N(lower alkyl, H)-lower alkyl, nitro, lower alkyl-S(O)$_2$—, carboxy, carboxy-lower alkyl, lower alkyl-COO-lower alkyl, lower alkyl-COO—, CO—N (lower alkyl, H)-lower alkyl, CO—N(lower alkyl, lower alkyl)-lower alkyl, CO—NH$_2$-lower alkyl and lower alkyl-CO—;

R$^6$ is H or lower alkyl;

R$^7$ is H or lower alkyl; and

L is —CH$_2$—CH$_2$—, —CH$_2$—O—, —CH$_2$—NH— or —CH=CH—, or a pharmaceutically acceptable salt or ester thereof.

2. The compound of claim 1, wherein L is —CH$_2$—CH$_2$—.

3. The compound of claim 1, wherein L is —CH$_2$—O—.

4. The compound of claim 1, wherein L is —CH=CH—.

5. The compound of claim 1, wherein L is —CH$_2$—NH—.

6. The compound of claim 1, wherein R$^2$ is H or lower alkyl.

7. The compound of claim 6, wherein R$^2$ is lower alkyl.

8. The compound of claim 7, wherein R$^2$ is methyl.

9. The compound of claim 1, wherein R$^3$ is H or lower alkyl.

10. The compound of claim 9, wherein R$^3$ is H or methyl.

11. The compound of claim 1, wherein R$^4$ is selected from the group consisting of
   i) H,
   ii) lower alkyl,
   iii) lower alkyl substituted by 1-2 substituents individually selected from cycloalkyl, halogen and hydroxy,
   iv) heteroaryl substituted by 1-2 lower alkyl groups,
   v) cycloalkyl,
   vi) cycloalkyl substituted by 1-2 hydroxy groups,
   vii) heterocyclyl, and
   viii) —NR$^6$R$^7$, wherein R$^6$ and R$^7$ are each individually selected from lower alkyl.

12. The compound of claim 11, wherein R$^4$ is selected from the group consisting of
   i) lower alkyl,
   ii) lower alkyl substituted by 1-2 substituents individually selected from cycloalkyl and hydroxy,
   iii) cycloalkyl, and
   iv) heterocyclyl.

13. The compound of claim 1, wherein R$^4$ is isopropyl, 2-hydroxy-ethyl, 2-hydroxy-1-hydroxymethyl-ethyl, 2-hydroxy-1-methyl-ethyl, 2-hydroxy-ethyl, cyclopropyl-methyl, cyclobutyl or 1,1-dioxo-tetrahydrothiophenyl.

14. The compound of claim 1, wherein R$^5$ is H.

15. The compound of claim 1, wherein R$^4$ and R$^5$ together with the nitrogen to which they are attached form a heterocyclyl or a heterocyclyl substituted by 1-4 substituents individually selected from halogen and lower alkoxy.

16. The compound of claim 1 selected from the group consisting of
   (1,1-Dioxothiomorpholin-4-yl)-(2-{(E)-2-[3-(5-fluoro-pyridin-2-yl)-5-methyl-isoxazol-4-yl]-vinyl}-thiazol-5-yl)-methanone,
   (2-{(E)-2-[3-(5-Fluoro-pyridin-2-yl)-5-methyl-isoxazol-4-yl]-vinyl}-thiazol-5-yl)-morpholin-4-yl-methanone,
   (2-{(E)-2-[3-(5-Fluoro-pyridin-2-yl)-5-methyl-isoxazol-4-yl]-vinyl}-thiazol-5-yl)-thiomorpholin-4-yl-methanone,
   (2-{2-[3-(5-Fluoro-pyridin-2-yl)-5-methyl-isoxazol-4-yl]-ethyl}-4-methyl-thiazol-5-yl)-thiomorpholin-4-yl-methanone,
   {2-[(E)-2-(3-Butyl-5-methyl-isoxazol-4-yl)-vinyl]-4-methyl-thiazol-5-yl}-(3,3-difluoro-azetidin-1-yl)-methanone,
   {2-[(E)-2-(3-Butyl-5-methyl-isoxazol-4-yl)-vinyl]-4-methyl-thiazol-5-yl}-(3-methoxy-azetidin-1-yl)-methanone,
   {2-[(E)-2-(3-Butyl-5-methyl-isoxazol-4-yl)-vinyl]-4-methyl-thiazol-5-yl}-morpholin-4-yl-methanone,
   {2-[(E)-2-(3-Butyl-5-methyl-isoxazol-4-yl)-vinyl]-4-methyl-thiazol-5-yl}-(2-oxa-6-aza-spiro[3.3]hept-6-yl)-methanone,
   {4-Methyl-2-[2-(5-methyl-3-pyridin-2-yl-isoxazol-4-yl)-ethyl]-thiazol-5-yl}-thiomorpholin-4-yl-methanone, and
   2-(3-Butyl-5-methyl-isoxazol-4-ylmethoxy)-thiazole-5-carboxylic acid isopropylamide
   or a pharmaceutically acceptable salt or ester thereof.

17. The compound of claim 1 selected from the group consisting of
   2-(3-Butyl-5-methyl-isoxazol-4-ylmethoxy)-thiazole-5-carboxylic acid (2-hydroxy-1-methyl-ethyl)-amide,
   2-(3-Butyl-5-methyl-isoxazol-4-ylmethoxy)-thiazole-5-carboxylic acid (2-hydroxy-ethyl)-amide,
   2-(5-Methyl-3-phenyl-isoxazol-4-ylmethoxy)-thiazole-5-carboxylic acid isopropylamide,
   2-(5-Methyl-3-phenyl-isoxazol-4-ylmethoxy)-thiazole-5-carboxylic acid (tetrahydro-pyran-4-yl)-amide,
   2-(5-Methyl-3-phenyl-isoxazol-4-ylmethoxy)-thiazole-5-carboxylic acid (2-hydroxy-1-methyl-ethyl)-amide,
   2-(5-Methyl-3-phenyl-isoxazol-4-ylmethoxy)-thiazole-5-carboxylic acid (2-hydroxy-ethyl)-amide,
   2-(5-Methyl-3-phenyl-isoxazol-4-ylmethoxy)-thiazole-5-carboxylic acid (2-hydroxy-1,1-dimethyl-ethyl)-amide,
   2-[(5-Methyl-3-phenyl-isoxazol-4-ylmethyl)-amino]-thiazole-5-carboxylic acid isopropylamide,
   2-[(5-Methyl-3-phenyl-isoxazol-4-ylmethyl)-amino]-thiazole-5-carboxylic acid (tetrahydro-pyran-4-yl)-amide, and
   2-[(E)-2-(3-Butyl-5-methyl-isoxazol-4-yl)-vinyl]-4-methyl-thiazole-5-carboxylic acid isopropylamide or a pharmaceutically acceptable salt or ester thereof.

18. The compound of claim 1 selected from the group consisting of
   2-[(E)-2-(3-Butyl-5-methyl-isoxazol-4-yl)-vinyl]-4-methyl-thiazole-5-carboxylic acid (tetrahydro-furan-3-yl)-amide,
   2-[(E)-2-(3-Butyl-5-methyl-isoxazol-4-yl)-vinyl]-4-methyl-thiazole-5-carboxylic acid (2-hydroxy-ethyl)-amide,
   2-[(E)-2-(3-Butyl-5-methyl-isoxazol-4-yl)-vinyl]-4-methyl-thiazole-5-carboxylic acid (tetrahydro-pyran-4-yl)-amide,
   2-[(E)-2-(3-Butyl-5-methyl-isoxazol-4-yl)-vinyl]-4-methyl-thiazole-5-carboxylic acid (2-hydroxy-1-methyl-ethyl)-amide,
   2-[(E)-2-(3-Butyl-5-methyl-isoxazol-4-yl)-vinyl]-4-methyl-thiazole-5-carboxylic acid (2-hydroxy-1-hydroxymethyl-ethyl)-amide,
   2-[(E)-2-(3-Butyl-5-methyl-isoxazol-4-yl)-vinyl]-4-methyl-thiazole-5-carboxylic acid amide,
   2-[(E)-2-(3-Butyl-5-methyl-isoxazol-4-yl)-vinyl]-4-methyl-thiazole-5-carboxylic acid N',N'-dimethyl-hydrazide,
   2-[(E)-2-(3-Butyl-5-methyl-isoxazol-4-yl)-vinyl]-4-methyl-thiazole-5-carboxylic acid morpholin-4-ylamide,
   2-[(E)-2-(3-Butyl-5-methyl-isoxazol-4-yl)-vinyl]-4-methyl-thiazole-5-carboxylic acid (1-hydroxymethyl-propyl)-amide, and 2-[(E)-2-(3-Butyl-5-methyl-isoxazol-4-yl)-vinyl]-4-methyl-thiazole-5-carboxylic acid ((R)-1-hydroxymethyl-propyl)-amide or a pharmaceutically acceptable salt or ester thereof.

19. The compound of claim 1 selected from the group consisting of

2-[(E)-2-(3-Butyl-5-methyl-isoxazol-4-yl)-vinyl]-4-methyl-thiazole-5-carboxylic acid ((S)-1-hydroxymethyl-propyl)-amide, 2-[(E)-2-(3-Butyl-5-methyl-isoxazol-4-yl)-vinyl]-4-methyl-thiazole-5-carboxylic acid ((R)-2,2,2-trifluoro-1-methyl-ethyl)-amide, 2-[(E)-2-(3-Butyl-5-methyl-isoxazol-4-yl)-vinyl]-4-methyl-thiazole-5-carboxylic acid ((1S,2S)-2-hydroxy-cyclopentyl)-amide, 2-[(E)-2-(3-Butyl-5-methyl-isoxazol-4-yl)-vinyl]-4-methyl-thiazole-5-carboxylic acid (1-methyl-1-pyrazol-4-yl)-amide, 2-[(E)-2-(3-Butyl-5-methyl-isoxazol-4-yl)-vinyl]-4-methyl-thiazole-5-carboxylic acid cyclopropylamide, 2-[(E)-2-(3-Butyl-5-methyl-isoxazol-4-yl)-vinyl]-4-methyl-thiazole-5-carboxylic acid ((1SR,2SR)-2-hydroxy-cyclopentyl)-amide, 2-[(E)-2-(3-Butyl-5-methyl-isoxazol-4-yl)-vinyl]-4-methyl-thiazole-5-carboxylic acid cyclobutylamide, 2-[(E)-2-(3-Butyl-5-methyl-isoxazol-4-yl)-vinyl]-4-methyl-thiazole-5-carboxylic acid cyclopropylmethyl-amide, 2-[(E)-2-(3-Butyl-5-methyl-isoxazol-4-yl)-vinyl]-4-methyl-thiazole-5-carboxylic acid (2-hydroxy-1,1-dimethyl-ethyl)-amide, and 2-[(E)-2-(3-Butyl-5-methyl-isoxazol-4-yl)-vinyl]-4-methyl-thiazole-5-carboxylic acid (1,1-dioxo-tetrahydrothiophen-3-yl)-amide or a pharmaceutically acceptable salt or ester thereof.

20. The compound of claim 1 selected from the group consisting of

2-[(E)-2-(3-Butyl-5-methyl-isoxazol-4-yl)-vinyl]-4-methyl-thiazole-5-carboxylic acid (2,2,2-trifluoro-ethyl)-amide, 2-[(E)-2-(3-Butyl-5-methyl-isoxazol-4-yl)-vinyl]-4-methyl-thiazole-5-carboxylic acid ethylamide, 2-[(E)-2-(3-Butyl-5-methyl-isoxazol-4-yl)-vinyl]-4-methyl-thiazole-5-carboxylic acid methylamide, 2-[(E)-2-(3-Butyl-5-methyl-isoxazol-4-yl)-vinyl]-thiazole-5-carboxylic acid isopropylamide, 2-[(E)-2-(3-Butyl-5-methyl-isoxazol-4-yl)-vinyl]-thiazole-5-carboxylic acid (2-hydroxy-ethyl)-amide, 2-[(E)-2-(5-Methyl-3-phenyl-isoxazol-4-yl)-vinyl]-thiazole-5-carboxylic acid (tetrahydro-pyran-4-yl)-amide, 2-[(E)-2-(5-Methyl-3-phenyl-isoxazol-4-yl)-vinyl]-thiazole-5-carboxylic acid ((R)-tetrahydro-furan-3-yl)-amide, 2-[(E)-2-(5-Methyl-3-phenyl-isoxazol-4-yl)-vinyl]-thiazole-5-carboxylic acid ((S)-tetrahydro-furan-3-yl)-amide, 2-[(E)-2-(5-Methyl-3-phenyl-isoxazol-4-yl)-vinyl]-thiazole-5-carboxylic acid isopropylamide, 2-[(E)-2-(5-Methyl-3-phenyl-isoxazol-4-yl)-vinyl]-thiazole-5-carboxylic acid (2-hydroxy-1-methyl-ethyl)-amide, and 2-[(E)-2-(5-Methyl-3-phenyl-isoxazol-4-yl)-vinyl]-thiazole-5-carboxylic acid (2-hydroxy-ethyl)-amide or a pharmaceutically acceptable salt or ester thereof.

21. The compound of claim 1 selected from the group consisting of

2-[(Z)-2-(3-Butyl-5-methyl-isoxazol-4-yl)-vinyl]-4-methyl-thiazole-5-carboxylic acid (2-hydroxy-ethyl)-amide, 2-[2-(3-Butyl-5-methyl-isoxazol-4-yl)-ethyl]-4-methyl-thiazole-5-carboxylic acid isopropylamide, 2-[2-(3-Butyl-5-methyl-isoxazol-4-yl)-ethyl]-4-methyl-thiazole-5-carboxylic acid (2-hydroxy-2-methyl-propyl)-amide, 2-[2-(3-Butyl-5-methyl-isoxazol-4-yl)-ethyl]-4-methyl-thiazole-5-carboxylic acid (2-hydroxy-1-methyl-ethyl)-amide, 2-[2-(3-Butyl-5-methyl-isoxazol-4-yl)-ethyl]-4-methyl-thiazole-5-carboxylic acid (tetrahydro-pyran-4-yl)-amide, 2-[2-(3-Butyl-5-methyl-isoxazol-4-yl)-ethyl]-4-methyl-thiazole-5-carboxylic acid (tetrahydro-furan-3-yl)-amide, 2-[2-(3-Butyl-5-methyl-isoxazol-4-yl)-ethyl]-4-methyl-thiazole-5-carboxylic acid (2-hydroxy-1-hydroxymethyl-ethyl)-amide, 2-[2-(3-Butyl-5-methyl-isoxazol-4-yl)-ethyl]-4-methyl-thiazole-5-carboxylic acid (S-2-hydroxy-1-methyl-ethyl)-amide, 2-[2-(3-Butyl-5-methyl-isoxazol-4-yl)-ethyl]-4-methyl-thiazole-5-carboxylic acid ((R)-2-hydroxy-1-methyl-ethyl)-amide, and 2-[2-(3-Butyl-5-methyl-isoxazol-4-yl)-ethyl]-4-methyl-thiazole-5-carboxylic acid (2-hydroxy-propyl)-amide or a pharmaceutically acceptable salt or ester thereof.

22. The compound of claim 1 selected from the group consisting of

2-[2-(3-Butyl-5-methyl-isoxazol-4-yl)-ethyl]-thiazole-5-carboxylic acid isopropylamide, 2-[2-(3-Butyl-5-methyl-isoxazol-4-yl)-ethyl]-thiazole-5-carboxylic acid (2-hydroxy-1-methyl-ethyl)-amide, 2-[2-(3-Butyl-5-methyl-isoxazol-4-yl)-ethyl]-thiazole-5-carboxylic acid (tetrahydro-pyran-4-yl)-amide, 2-[2-(3-Butyl-5-methyl-isoxazol-4-yl)-ethyl]-thiazole-5-carboxylic acid (tetrahydro-furan-3-yl)-amide, 2-[2-(3-Butyl-5-methyl-isoxazol-4-yl)-ethyl]-thiazole-5-carboxylic acid ((S)-2-hydroxy-1-methyl-ethyl)-amide, 2-[2-(3-Butyl-5-methyl-isoxazol-4-yl)-ethyl]-thiazole-5-carboxylic acid (2-hydroxy-propyl)-amide, 4-Methyl-2-[2-(5-methyl-3-phenyl-isoxazol-4-yl)-ethyl]-thiazole-5-carboxylic acid isopropylamide, 2-[2-(5-Methyl-3-phenyl-isoxazol-4-yl)-ethyl]-thiazole-5-carboxylic acid isopropylamide, 2-[2-(5-Methyl-3-pyridin-2-yl-isoxazol-4-yl)-ethyl]-thiazole-5-carboxylic acid isopropylamide, 2-[2-(5-Methyl-3-pyridin-2-yl-isoxazol-4-yl)-ethyl]-thiazole-5-carboxylic acid cyclopropylamide, and 2-[2-(5-Methyl-3-pyridin-2-yl-isoxazol-4-yl)-ethyl]-thiazole-5-carboxylic acid (tetrahydro-pyran-4-yl)-amide or a pharmaceutically acceptable salt or ester thereof.

23. The compound of claim 1 selected from the group consisting of

2-[2-(5-Methyl-3-pyridin-2-yl-isoxazol-4-yl)-ethyl]-thiazole-5-carboxylic acid amide, 2-[2-(5-Methyl-3-pyridin-2-yl-isoxazol-4-yl)-ethyl]-thiazole-5-carboxylic acid cyclopropylmethyl-amide, 2-[2-(5-Methyl-3-pyridin-2-yl-isoxazol-4-yl)-ethyl]-thiazole-5-carboxylic acid (1,1-dioxo-tetrahydrothiophen-3-yl)-amide, 2-[2-(5-Methyl-3-pyridin-2-yl-isoxazol-4-yl)-ethyl]-thiazole-5-carboxylic acid (2,2,2-trifluoro-ethyl)-amide, 2-[2-(5-Methyl-3-pyridin-2-yl-isoxazol-4-yl)-ethyl]-thiazole-5-carboxylic acid (2-hydroxy-ethyl)-amide,
2-{(E)-2-[3-(5-Fluoro-pyridin-2-yl)-5-methyl-isoxazol-4-yl]-vinyl}-4-methyl-thiazole-5-carboxylic acid isopropylamide,
2-{(E)-2-[3-(5-Fluoro-pyridin-2-yl)-5-methyl-isoxazol-4-yl]-vinyl}-4-methyl-thiazole-5-carboxylic acid (tetrahydro-pyran-4-yl)-amide,
2-{(E)-2-[3-(5-Fluoro-pyridin-2-yl)-5-methyl-isoxazol-4-yl]-vinyl}-4-methyl-thiazole-5-carboxylic acid cyclopropylamide,
2-{(E)-2-[3-(5-Fluoro-pyridin-2-yl)-5-methyl-isoxazol-4-yl]-vinyl}-4-methyl-thiazole-5-carboxylic acid (2-hydroxy-1,1-dimethyl-ethyl)-amide, and
2-{(E)-2-[3-(5-Fluoro-pyridin-2-yl)-5-methyl-isoxazol-4-yl]-vinyl}-4-methyl-thiazole-5-carboxylic acid cyclopropylmethyl-amide or a pharmaceutically acceptable salt or ester thereof.

24. The compound of claim 1 selected from the group consisting of
2-{(E)-2-[3-(5-Fluoro-pyridin-2-yl)-5-methyl-isoxazol-4-yl]-vinyl}-4-methyl-thiazole-5-carboxylic acid amide,
2-{(E)-2-[3-(5-Fluoro-pyridin-2-yl)-5-methyl-isoxazol-4-yl]-vinyl}-thiazole-5-carboxylic acid (tetrahydro-pyran-4-yl)-amide,
2-{(E)-2-[3-(5-Fluoro-pyridin-2-yl)-5-methyl-isoxazol-4-yl]-vinyl}-thiazole-5-carboxylic acid isopropylamide,
2-{(E)-2-[3-(5-Fluoro-pyridin-2-yl)-5-methyl-isoxazol-4-yl]-vinyl}-thiazole-5-carboxylic acid cyclopropylamide,
2-{(E)-2-[3-(5-Fluoro-pyridin-2-yl)-5-methyl-isoxazol-4-yl]-vinyl}-thiazole-5-carboxylic acid (2-hydroxy-1,1-dimethyl-ethyl)-amide,
2-{(E)-2-[3-(5-Fluoro-pyridin-2-yl)-5-methyl-isoxazol-4-yl]-vinyl}-thiazole-5-carboxylic acid amide,
2-{(E)-2-[3-(5-Fluoro-pyridin-2-yl)-5-methyl-isoxazol-4-yl]-vinyl}-thiazole-5-carboxylic acid cyclopropylmethyl-amide,
2-{(E)-2-[3-(5-Fluoro-pyridin-2-yl)-5-methyl-isoxazol-4-yl]-vinyl}-thiazole-5-carboxylic acid (2,2,2-trifluoro-ethyl)-amide,
2-{(E)-2-[3-(5-Fluoro-pyridin-2-yl)-5-methyl-isoxazol-4-yl]-vinyl}-thiazole-5-carboxylic acid (2-hydroxy-ethyl)-amide, and
2-{(E)-2-[3-(5-Fluoro-pyridin-2-yl)-5-methyl-isoxazol-4-yl]-vinyl}-thiazole-5-carboxylic acid ethylamide or a pharmaceutically acceptable salt or ester thereof.

25. The compound of claim 1 selected from the group consisting of
2-{(E)-2-[3-(5-Fluoro-pyridin-2-yl)-5-methyl-isoxazol-4-yl]-vinyl}-thiazole-5-carboxylic acid methylamide,
2-{(E)-2-[3-(5-Fluoro-pyridin-2-yl)-isoxazol-4-yl]-vinyl}-4-methyl-thiazole-5-carboxylic acid (tetrahydro-pyran-4-yl)-amide,
2-{(E)-2-[3-(5-Fluoro-pyridin-2-yl)-isoxazol-4-yl]-vinyl}-4-methyl-thiazole-5-carboxylic acid cyclopropylamide,
2-{(E)-2-[3-(5-Fluoro-pyridin-2-yl)-isoxazol-4-yl]-vinyl}-4-methyl-thiazole-5-carboxylic acid cyclopropylmethyl-amide,
2-{2-[3-(5-Fluoro-pyridin-2-yl)-5-methyl-isoxazol-4-yl]-ethyl}-4-methyl-thiazole-5-carboxylic acid (tetrahydro-pyran-4-yl)-amide,
2-{2-[3-(5-Fluoro-pyridin-2-yl)-5-methyl-isoxazol-4-yl]-ethyl}-4-methyl-thiazole-5-carboxylic acid isopropylamide,
2-{2-[3-(5-Fluoro-pyridin-2-yl)-5-methyl-isoxazol-4-yl]-ethyl}-4-methyl-thiazole-5-carboxylic acid cyclopropylamide,
2-{2-[3-(5-Fluoro-pyridin-2-yl)-5-methyl-isoxazol-4-yl]-ethyl}-4-methyl-thiazole-5-carboxylic acid cyclopropylmethyl-amide,
2-{2-[3-(5-Fluoro-pyridin-2-yl)-5-methyl-isoxazol-4-yl]-ethyl}-4-methyl-thiazole-5-carboxylic acid (2,2,2-trifluoro-ethyl)-amide, and
2-{2-[3-(5-Fluoro-pyridin-2-yl)-5-methyl-isoxazol-4-yl]-ethyl}-4-methyl-thiazole-5-carboxylic acid (2-hydroxy-ethyl)-amide or a pharmaceutically acceptable salt or ester thereof.

26. The compound of claim 1 selected from the group consisting of
2-{2-[3-(5-Fluoro-pyridin-2-yl)-5-methyl-isoxazol-4-yl]-ethyl}-4-methyl-thiazole-5-carboxylic acid ethylamide,
2-{2-[3-(5-Fluoro-pyridin-2-yl)-5-methyl-isoxazol-4-yl]-ethyl}-4-methyl-thiazole-5-carboxylic acid methylamide,
2-{2-[3-(5-Fluoro-pyridin-2-yl)-5-methyl-isoxazol-4-yl]-ethyl}-thiazole-5-carboxylic acid (tetrahydro-pyran-4-yl)-amide,
2-{2-[3-(5-Fluoro-pyridin-2-yl)-5-methyl-isoxazol-4-yl]-ethyl}-thiazole-5-carboxylic acid isopropylamide,
2-{2-[3-(5-Fluoro-pyridin-2-yl)-5-methyl-isoxazol-4-yl]-ethyl}-thiazole-5-carboxylic acid cyclopropylamide,
2-{2-[3-(5-Fluoro-pyridin-2-yl)-5-methyl-isoxazol-4-yl]-ethyl}-thiazole-5-carboxylic acid cyclopropylmethyl-amide,
2-{2-[3-(5-Fluoro-pyridin-2-yl)-5-methyl-isoxazol-4-yl]-ethyl}-thiazole-5-carboxylic acid (2,2,2-trifluoro-ethyl)-amide,
2-{2-[3-(5-Fluoro-pyridin-2-yl)-5-methyl-isoxazol-4-yl]-ethyl}-thiazole-5-carboxylic acid (2-hydroxy-ethyl)-amide,
2-{2-[3-(5-Fluoro-pyridin-2-yl)-5-methyl-isoxazol-4-yl]-ethyl}-thiazole-5-carboxylic acid ethylamide, and
2-{2-[3-(5-Fluoro-pyridin-2-yl)-5-methyl-isoxazol-4-yl]-ethyl}-thiazole-5-carboxylic acid methylamide or a pharmaceutically acceptable salt or ester thereof.

27. The compound of claim 1 selected from the group consisting of
4-Methyl-2-[(E)-2-(5-methyl-3-phenyl-isoxazol-4-yl)-vinyl]-thiazole-5-carboxylic acid isopropylamide,
4-Methyl-2-[(E)-2-(5-methyl-3-phenyl-isoxazol-4-yl)-vinyl]-thiazole-5-carboxylic acid (tetrahydro-furan-3-yl)-amide,
4-Methyl-2-[(E)-2-(5-methyl-3-phenyl-isoxazol-4-yl)-vinyl]-thiazole-5-carboxylic acid (2-hydroxy-ethyl)-amide,
4-Methyl-2-[2-(3-pyridin-2-yl-isoxazol-4-yl)-ethyl]-thiazole-5-carboxylic acid (tetrahydro-pyran-4-yl)-amide,
4-Methyl-2-[2-(3-pyridin-2-yl-isoxazol-4-yl)-ethyl]-thiazole-5-carboxylic acid (2,2,2-trifluoro-ethyl)-amide,
4-Methyl-2-[2-(5-methyl-3-phenyl-isoxazol-4-yl)-ethyl]-thiazole-5-carboxylic acid (tetrahydro-furan-3(R)-yl)-amide,
4-Methyl-2-[2-(5-methyl-3-phenyl-isoxazol-4-yl)-ethyl]-thiazole-5-carboxylic acid (tetrahydro-furan-3(S)-yl)-amide,
4-Methyl-2-[2-(5-methyl-3-phenyl-isoxazol-4-yl)-ethyl]-thiazole-5-carboxylic acid (2-hydroxy-1-methyl-ethyl)-amide, 4-Methyl-2-[2-(5-methyl-3-phenyl-isoxazol-4-yl)-ethyl]-thiazole-5-carboxylic acid (2-hydroxy-2-methyl-propyl)-amide, and 4-Methyl-2-[2-(5-methyl-3-phenyl-isoxazol-4-yl)-ethyl]-thiazole-5-carboxylic acid (tetrahydro-pyran-4-yl)-amide or a pharmaceutically acceptable salt or ester thereof.

28. The compound of claim 1 selected from the group consisting of

4-Methyl-2-[2-(5-methyl-3-phenyl-isoxazol-4-yl)-ethyl]-thiazole-5-carboxylic acid amide, 4-Methyl-2-[2-(5-methyl-3-pyridin-2-yl-isoxazol-4-yl)-ethyl]-thiazole-5-carboxylic acid (tetrahydro-pyran-4-yl)-amide, 4-Methyl-2-[2-(5-methyl-3-pyridin-2-yl-isoxazol-4-yl)-ethyl]-thiazole-5-carboxylic acid isopropylamide, 4-Methyl-2-[2-(5-methyl-3-pyridin-2-yl-isoxazol-4-yl)-ethyl]-thiazole-5-carboxylic acid cyclopropylamide, 4-Methyl-2-[2-(5-methyl-3-pyridin-2-yl-isoxazol-4-yl)-ethyl]-thiazole-5-carboxylic acid cyclopropylmethyl-amide, 4-Methyl-2-[2-(5-methyl-3-pyridin-2-yl-isoxazol-4-yl)-ethyl]-thiazole-5-carboxylic acid (2,2,2-trifluoro-ethyl)-amide, 4-Methyl-2-[2-(5-methyl-3-pyridin-2-yl-isoxazol-4-yl)-ethyl]-thiazole-5-carboxylic acid (2-hydroxy-ethyl)-amide, 4-Methyl-2-[2-(5-methyl-3-pyridin-2-yl-isoxazol-4-yl)-ethyl]-thiazole-5-carboxylic acid ethylamide, 4-Methyl-2-[2-(5-methyl-3-pyridin-2-yl-isoxazol-4-yl)-ethyl]-thiazole-5-carboxylic acid methylamide, 4-Methyl-2-[2-(5-methyl-3-pyridin-2-yl-isoxazol-4-yl)-ethyl]-thiazole-5-carboxylic acid amide, and Azetidin-1-yl-{2-[(E)-2-(3-butyl-5-methyl-isoxazol-4-yl)-vinyl]-4-methyl-thiazol-5-yl}-methanone, or a pharmaceutically acceptable salt or ester thereof.

29. The compound of claim 1 selected from the group consisting of

2-[(E)-2-(3-Butyl-5-methyl-isoxazol-4-yl)-vinyl]-4-methyl-thiazole-5-carboxylic acid (2-hydroxy-ethyl)-amide, 2-[(E)-2-(3-Butyl-5-methyl-isoxazol-4-yl)-vinyl]-4-methyl-thiazole-5-carboxylic acid cyclobutylamide, 2-[(E)-2-(3-Butyl-5-methyl-isoxazol-4-yl)-vinyl]-4-methyl-thiazole-5-carboxylic acid cyclopropylmethyl-amide, 2-[(E)-2-(3-Butyl-5-methyl-isoxazol-4-yl)-vinyl]-4-methyl-thiazole-5-carboxylic acid (1,1-dioxo-tetrahydrothiophen-3-yl)-amide, 2-[(E)-2-(5-Methyl-3-phenyl-isoxazol-4-yl)-vinyl]-thiazole-5-carboxylic acid (2-hydroxy-1-methyl-ethyl)-amide, 2-[2-(3-Butyl-5-methyl-isoxazol-4-yl)-ethyl]-4-methyl-thiazole-5-carboxylic acid (2-hydroxy-1-hydroxymethyl-ethyl)-amide, 4-Methyl-2-[2-(5-methyl-3-phenyl-isoxazol-4-yl)-ethyl]-thiazole-5-carboxylic acid isopropylamide, 2-[2-(5-Methyl-3-phenyl-isoxazol-4-yl)-ethyl]-thiazole-5-carboxylic acid isopropylamide, 2-{(E)-2-[3-(5-Fluoro-pyridin-2-yl)-5-methyl-isoxazol-4-yl]-vinyl}-4-methyl-thiazole-5-carboxylic acid isopropylamide, 2-{(E)-2-[3-(5-Fluoro-pyridin-2-yl)-5-methyl-isoxazol-4-yl]-vinyl}-thiazole-5-carboxylic acid isopropylamide, 4-Methyl-2-[2-(5-methyl-3-pyridin-2-yl-isoxazol-4-yl)-ethyl]-thiazole-5-carboxylic acid isopropylamide, and 4-Methyl-2-[2-(5-methyl-3-pyridin-2-yl-isoxazol-4-yl)-ethyl]-thiazole-5-carboxylic acid (2-hydroxy-ethyl)-amide, or a pharmaceutically acceptable salt or ester thereof.

30. The compound of claim 29, which is 2-[(E)-2-(3-Butyl-5-methyl-isoxazol-4-yl)-vinyl]-4-methyl-thiazole-5-carboxylic acid (2-hydroxy-ethyl)-amide, or a pharmaceutically acceptable salt or ester thereof.

31. The compound of claim 1 having formula II,

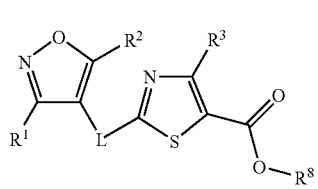

wherein $R^1$, $R^2$, $R^3$ and L are as defined in claim 1 and
$R^8$ is selected from the group consisting of
  i) H,
  ii) lower alkyl, and
  iii) lower alkyl substituted by 1-5 substituents individually selected from acetamidyl, acetyl, acetylamino, amido, amino, carboxy, cyano, cycloalkyl, halogen, halogen-lower alkoxy, heterocyclyl, hydroxy, lower alkoxy, (lower alkyl, lower alkyl)N—, (lower alkyl, H)N—, nitro and lower alkyl-S(O)$_2$—,
or a pharmaceutically acceptable salt or ester thereof.

32. A pharmaceutical composition comprising a therapeutically effective amount of a compound of formula I

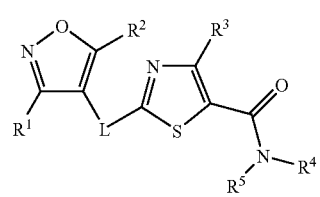

wherein
$R^1$ is selected from the group consisting of
  i) lower alkyl,
  ii) lower alkyl substituted by 1-5 halogen atoms,
  iii) aryl,
  iv) aryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl, H)N—, N(lower alkyl, lower alkyl)-lower alkyl, N(lower alkyl, H)-lower alkyl, nitro, lower alkyl-S(O)$_2$—, carboxy, carboxy-lower alkyl, lower alkyl-COO-lower alkyl, COO-lower alkyl, CO—N(lower alkyl, H)-lower alkyl, CO—N(lower alkyl, lower alkyl)-lower alkyl, CO—NH$_2$-lower alkyl and lower alkyl-CO—,
  v) heteroaryl, and
  vi) heteroaryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl, H)N—, N(lower alkyl, lower alkyl)-lower alkyl, N(lower alkyl, H)-lower alkyl, nitro, lower alkyl-S(O)$_2$—, carboxy, carboxy-lower alkyl, lower alkyl-COO-lower alkyl, lower alkyl-COO—, CO—N(lower alkyl, H)-lower alkyl, CO—N(lower alkyl, lower alkyl)-lower alkyl, CO—NH$_2$-lower alkyl and lower alkyl-CO—, $R^2$ is H, lower alkyl or lower alkyl substituted by 1-5 substituents individually selected from halogen and hydroxy;

$R^3$ is H, lower alkyl or lower alkyl substituted by 1-5 halogen atoms;

$R^4$ is selected from the group consisting of
  i) H,
  ii) lower alkyl,
  iii) lower alkyl substituted by 1-5 substituents individually selected from acetamidyl, acetyl, acetylamino, amido, amino, carboxy, cyano, cycloalkyl, halogen, halogen-lower alkoxy, heterocyclyl, hydroxy, lower alkoxy, (lower alkyl, lower alkyl)N—, (lower alkyl, H)N—, nitro and lower alkyl-S(O)$_2$—,
  iv) aryl,
  v) heteroaryl,
  vi) heteroaryl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl, H)N—, N(lower alkyl, lower alkyl)-lower alkyl, N(lower alkyl, H)-lower alkyl, nitro, lower alkyl-S(O)$_2$—, carboxy, carboxy-lower alkyl, lower alkyl-COO-lower alkyl, lower alkyl-COO—, CO—N(lower alkyl, H)-lower alkyl, CO—N(lower alkyl, lower alkyl)-lower alkyl, CO—NH$_2$-lower alkyl, and lower alkyl-CO—,
  vii) cycloalkyl,
  viii) cycloalkyl substituted by 1-4 substituents individually selected from halogen and hydroxy,
  ix) heterocyclyl, and
  x) —NR$^6$R$^7$;

$R^5$ is H, lower alkyl or lower alkyl substituted by 1-5 halogen atoms;

or $R^4$ and $R^5$ together with the nitrogen to which they are attached form a heterocyclyl or a heterocyclyl substituted by 1-4 substituents individually selected from amino, amino-lower alkyl, cyano, cyano-lower alkyl, halogen, halogen-lower alkyl, hydroxy, hydroxy-lower alkyl, lower alkoxy-lower alkyl, lower alkyl, lower alkoxy, halogen-lower alkoxy, (lower alkyl, lower alkyl)N—, (lower alkyl, H)N—, N(lower alkyl, lower alkyl)-lower alkyl, N(lower alkyl, H)-lower alkyl, nitro, lower alkyl-S(O)$_2$—, carboxy, carboxy-lower alkyl, lower alkyl-COO-lower alkyl, lower alkyl-COO—, CO—N(lower alkyl, H)-lower alkyl, CO—N(lower alkyl, lower alkyl)-lower alkyl, CO—NH$_2$-lower alkyl and lower alkyl-CO—;

$R^6$ is H or lower alkyl;
$R^7$ is H or lower alkyl; and
L is —CH$_2$—CH$_2$—, —CH$_2$—O—, —CH$_2$—NH— or —CH=CH—, or a pharmaceutically acceptable salt or ester thereof and a pharmaceutically acceptable carrier.

33. The pharmaceutical composition of claim 32 wherein the compound of formula I is a compound of formula II

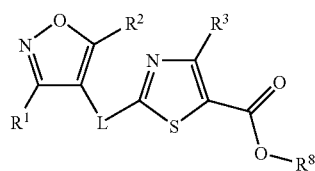

wherein
$R^8$ is selected from the group consisting of
  i) H,
  ii) lower alkyl, and
  iii) lower alkyl substituted by 1-5 substituents individually selected from acetamidyl, acetyl, acetylamino, amido, amino, carboxy, cyano, cycloalkyl, halogen, halogen-lower alkoxy, heterocyclyl, hydroxy, lower alkoxy, (lower alkyl, lower alkyl)N—, (lower alkyl, H)N—, nitro and lower alkyl-S(O)$_2$—, or a pharmaceutically acceptable salt or ester thereof.

* * * * *